(12) United States Patent
Yokoyama

(10) Patent No.: US 10,053,679 B2
(45) Date of Patent: Aug. 21, 2018

(54) CELLULASE GENE

(75) Inventor: Fumikazu Yokoyama, Kanagawa (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 511 days.

(21) Appl. No.: 13/638,538

(22) PCT Filed: Mar. 31, 2010

(86) PCT No.: PCT/JP2010/055897
§ 371 (c)(1),
(2), (4) Date: Sep. 28, 2012

(87) PCT Pub. No.: WO2011/121768
PCT Pub. Date: Oct. 6, 2011

(65) Prior Publication Data
US 2013/0023014 A1   Jan. 24, 2013

(51) Int. Cl.
| | |
|---|---|
| C12N 9/24 | (2006.01) |
| C12N 9/42 | (2006.01) |
| C12P 19/02 | (2006.01) |
| C12P 19/14 | (2006.01) |
| D06M 16/00 | (2006.01) |
| D21C 5/00 | (2006.01) |
| D21C 5/02 | (2006.01) |
| D21H 21/10 | (2006.01) |
| A23K 20/189 | (2016.01) |
| A23K 10/14 | (2016.01) |

(52) U.S. Cl.
CPC ............ *C12N 9/2437* (2013.01); *A23K 10/14* (2016.05); *A23K 20/189* (2016.05); *C12N 9/2445* (2013.01); *C12P 19/02* (2013.01); *C12P 19/14* (2013.01); *C12Y 302/01004* (2013.01); *C12Y 302/01021* (2013.01); *D06M 16/003* (2013.01); *D21C 5/005* (2013.01); *D21C 5/025* (2013.01); *D21H 21/10* (2013.01); *C12P 2203/00* (2013.01); *Y02E 50/16* (2013.01); *Y02W 30/648* (2015.05)

(58) Field of Classification Search
None
See application file for complete search history.

(56) References Cited

U.S. PATENT DOCUMENTS

| | | |
|---|---|---|
| 6,127,160 A | 10/2000 | Yamanobe et al. |
| 6,921,655 B1 | 7/2005 | Nakamura et al. |
| 2004/0091469 A1 | 5/2004 | Fukasawa et al. |
| 2005/0143275 A1 | 6/2005 | Murashima et al. |
| 2006/0005279 A1 | 1/2006 | Dotson |
| 2006/0179511 A1 | 8/2006 | Chomet et al. |
| 2008/0299613 A1 | 12/2008 | Merino |
| 2010/0098807 A1 | 4/2010 | Moriya et al. |
| 2010/0143971 A1 | 6/2010 | Spodsberg |

FOREIGN PATENT DOCUMENTS

| | | |
|---|---|---|
| CN | 1965078 A | 5/2007 |
| CN | 102300986 A | 12/2011 |
| EP | 0 674 843 A1 | 10/1995 |
| JP | 07-236431 A | 9/1995 |
| JP | 07-264994 A | 10/1995 |
| JP | 2531595 B2 | 9/1996 |
| JP | 10-066569 A | 3/1998 |
| JP | 2000-069978 A | 3/2000 |
| JP | 2000-298262 A | 10/2000 |
| JP | 2001-017180 A | 1/2001 |
| JP | 2002-101876 A | 4/2002 |
| JP | 2003135052 A | 5/2003 |
| JP | 2003-164284 A | 6/2003 |
| JP | 2004-313022 A | 11/2004 |
| WO | 97/33982 A1 | 9/1997 |
| WO | 99/11767 A1 | 3/1999 |
| WO | 00/24879 A1 | 5/2000 |
| WO | 01/90375 A1 | 11/2001 |
| WO | 2007/044043 A2 | 4/2007 |
| WO | 2008/111613 A1 | 9/2008 |
| WO | 2008/140749 A2 | 11/2008 |
| WO | 2011/005867 A1 | 1/2011 |

(Continued)

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
Fedorova et al. (Unipro database Accession: B8M2G3 TALSN, Mar. 3, 2009).*
Database UniProt [Online]; Dec. 16, 2008 (Dec. 16, 2008), "SubName: Full=Endoglucanase, putative;", XP002704020, retrieved from EBI accession No. UniProt: B6Q8F1; Database accession No. B6Q8F1 *the whole document*.
Database UniProt [Online]; Mar. 3, 2009, "SubName: Full=Endoglucanase, putative;", XP002704021, retrieved from EBI accession No. UniProt: B*M2G3 Database accession No. B8M2G3 the whole document.
"Talaromyces emersonii endo beta 1,4 glucanase (egl) gene, partial cds.", NCBI Sequence Revision History [online]; Accession:AF440013, http://www.ncbi.nlm.nih.gov/sviewer/viewer.fcgi?val=21264636&sat=NCBI&satkey=39386869, May 30, 2002, 2 pages.

(Continued)

Primary Examiner — Richard G Hutson
(74) Attorney, Agent, or Firm — Sughrue Mion, PLLC

(57) ABSTRACT

An object is to identify endoglucanase and β-glucosidase genes by isolating genomic DNA containing cellulase genes, which are classified into endoglucanases or β-glucosidases, from *Acremonium cellulolyticus*, and sequencing the nucleotide sequences thereof. The inventors intensively compared the amino acid sequences of known endoglucanases and β-glucosidases with each other to find conserved region of amino acid sequences in *Acremonium cellulolyticus*, and various primers were designed based on the information. PCR was carried out using the various primers thus designed and genomic DNA or cDNA as a template. As a result, gene fragments of endoglucanases and β-glucosidases were obtained. Primers were designed based on the gene fragments, and PCR was carried out to amplify nine genes of endoglucanases and β-glucosidases. The nucleotide sequences thereof were sequenced, and the present invention was completed.

2 Claims, 5 Drawing Sheets

(56) References Cited

FOREIGN PATENT DOCUMENTS

| WO | 2011/057140 A1 | 5/2011 |
|---|---|---|
| WO | 2011/059740 A1 | 5/2011 |
| WO | 2011/123505 A1 | 10/2011 |

OTHER PUBLICATIONS

E. Vlasenko, et al., "Substrate specificity of family 5,6,7,9,12, and 45 endoglucanases", Bioresource Technology, 2010, pp. 2405-2411.

Pengjun Shi, et al., "Cloning, characterization, and antifungal activity of an endo-1,3-β-D-glucanase from *Streptomyces* sp. S27", Appl. Microbiol Biotechnol, 2010, pp. 1483-1490, vol. 85.

Paul O. Sheppard, et al., "The use of conserved cellulase family-specific sequences to clone cellulase homologue cDNAs from *Fusarium oxysporum*", Gene, 1994, pp. 163-167, vol. 150, No. 1.

Takashi Yamanobe, et al., "Isolation of a Cellulolytic Enzyme Producing Microorganism, Culture Conditions and Some Properties of the Enzymes", Agric. Biol. Chem., 1987, pp. 65-74, vol. 51, No. 1.

GenBank: XP_002478590; endoglucanase, putative [Talaromyces stipitatus ATCC 10500].

"Penicillium marneffei ATCC 18224 endoglucanase, putative, mRNA", NCBI Reference Sequence: XM_002152933.1, GI:212545630, 2 pages total.

Accession No. B6QKD0, UniProtKB [online], Dec. 16, 2008, retrieved from http://www.uniprot.org/uniprot/B6QKD0 (6 pages total).

Schulein, M. et al., "Characterization of fungal cellulases for fiber modification," Book of Abstracts, 213th ACS National Meeting, San Francisco, Apr. 13-17, 1997, Chemical Abstracts [online], Accession No. 1997:159095 (1 page total).

\* cited by examiner

CELLULASE GENE

CROSS REFERENCE TO RELATED APPLICATIONS

This application is a National Stage of International Application No. PCT/JP2010/055897 filed Mar. 31, 2010, the contents of which are incorporated herein by reference in their entirety.

TECHNICAL FIELD

The present invention relates to cellulases, more particularly, cellulases derived from *Acremonium cellulolyticus*, polynucleotides encoding the cellulases, a process of producing the cellulases using the polynucleotides, and a use of the cellulases. The term "polynucleotide" as used herein includes DNA and RNA, and modifications and chimeras thereof, preferably DNA.

BACKGROUND ART

Cellulase is a generic term for enzymes which decompose cellulose. Cellulase produced by microorganisms is generally composed of many types of cellulase components. The cellulase components are classified by their substrate specificity into three types: cellobiohydrolase, endoglucanase, and β-glucosidase. It is considered that *Aspergillus niger*, a filamentous fungus which produces cellulase, produces four types of cellobiohydrolase, fifteen types of endoglucanases, and fifteen types of β-glucosidases at the maximum. Therefore, when cellulase produced by a microorganism is industrially utilized, it is used as a mixture of various cellulase components produced by the microorganism.

A filamentous fungus *Acremonium cellulolyticus* is characterized by producing cellulase having high saccharification ability (non-patent literature 1), and it is reported that it has high usefulness for feed use or silage use (patent literatures 1-3). The cellulase components contained (patent literatures 4-10) have been studied in detail, and it is clarified that many kinds of cellulase components are secreted similarly to other filamentous fungi.

It is considered that several types of specific enzyme components in many types of cellulase components are important for a certain limited use. Therefore, if the cellulase component composition of cellulase produced by a microorganism can be optimized according to the use, it is expected that cellulase having higher activity can be obtained. The best way to accomplish this is to overexpress a specific enzyme by the introduction of its specific enzyme gene, or to disrupt a specific enzyme gene, using gene recombination techniques.

However, only two types of cellobiohydrolases (patent literatures 4 and 5) and a type of β-glucosidase (patent literature 10) were isolated in *Acremonium cellulolyticus*, and thus, enhanced expression by gene introduction or suppressed expression by gene disruption could not be carried out with respect to the other cellulases.

Under these circumstances, the isolation of genes for polysaccharide-degrading enzymes such as endoglucanase and β-glucosidase has been desired to optimize the composition of cellulase components produced by *Acremonium cellulolyticus*, using gene recombination techniques.

CITATION LIST

Non-Patent Literature

[Non-patent literature 1] Agricultural and Biological Chemistry, Japan, 1987, Vol. 51, p. 65

Patent Literature

[Patent literature 1] Japanese Unexamined Patent Publication (Kokai) No. 7-264994
[Patent literature 2] Japanese Patent No. 2531595
[Patent literature 3] Japanese Unexamined Patent Publication (Kokai) No. 7-236431
[Patent literature 4] Japanese Unexamined Patent Publication (Kokai) No. 2001-17180
[Patent literature 5] WO97/33982
[Patent literature 6] WO99/011767
[Patent literature 7] Japanese Unexamined Patent Publication (Kokai) No. 2000-69978
[Patent literature 8] Japanese Unexamined Patent Publication (Kokai) No. 10-066569
[Patent literature 9] Japanese Unexamined Patent Publication (Kokai) No. 2002-101876
[Patent literature 10] Japanese Unexamined Patent Publication (Kokai) No. 2000-298262

SUMMARY OF INVENTION

Technical Problem

An object of the present invention is to identify endoglucanase and β-glucosidase genes by isolating genomic DNA containing cellulase genes, which are classified into endoglucanases or β-glucosidases, from *Acremonium cellulolyticus*, and sequencing the nucleotide sequences thereof.

Solution to Problem

To solve the problem, the inventors intensively compared the amino acid sequences of known endoglucanases and β-glucosidases with each other to find conserved region of amino acid sequences in *Acremonium cellulolyticus*, and various primers were designed based on the information. PCR was carried out using the various primers thus designed and genomic DNA or cDNA as a template. As a result, gene fragments of endoglucanases and β-glucosidases were obtained. Primers were designed based on the gene fragments, and PCR was carried out to amplify nine genes of endoglucanases and β-glucosidases. The nucleotide sequences thereof were sequenced, and the present invention was completed.

The present invention relates to:
[1] a protein selected from:
(i) a protein comprising amino acids 1-306 of SEQ ID NO: 2;
(ii) an endoglucanase comprising an amino acid sequence in which one or plural amino acids are deleted, substituted, and/or added in amino acids 1-306 of SEQ ID NO: 2; or
(iii) an endoglucanase comprising an amino acid sequence having a 70% identity or more with amino acids 1-306 of SEQ ID NO: 2,

[2] a protein selected from:
(i) a protein comprising amino acids 1-475 of SEQ ID NO: 4;
(ii) an endoglucanase comprising an amino acid sequence in which one or plural amino acids are deleted, substituted, and/or added in amino acids 1-475 of SEQ ID NO: 4; or
(iii) an endoglucanase comprising an amino acid sequence having a 70% identity or more with amino acids 1-475 of SEQ ID NO: 4,
[3] a protein selected from:
(i) a protein comprising amino acids 1-391 of SEQ ID NO: 6;
(ii) an endoglucanase comprising an amino acid sequence in which one or plural amino acids are deleted, substituted, and/or added in amino acids 1-391 of SEQ ID NO: 6; or
(iii) an endoglucanase comprising an amino acid sequence having a 70% identity or more with amino acids 1-391 of SEQ ID NO: 6,
[4] a protein selected from:
(i) a protein comprising amino acids 1-376 of SEQ ID NO: 8;
(ii) an endoglucanase comprising an amino acid sequence in which one or plural amino acids are deleted, substituted, and/or added in amino acids 1-376 of SEQ ID NO: 8; or
(iii) an endoglucanase comprising an amino acid sequence having a 70% identity or more with amino acids 1-376 of SEQ ID NO: 8,
[5] a protein selected from:
(i) a protein comprising amino acids 1-221 of SEQ ID NO: 10;
(ii) an endoglucanase comprising an amino acid sequence in which one or plural amino acids are deleted, substituted, and/or added in amino acids 1-221 of SEQ ID NO: 10; or
(iii) an endoglucanase comprising an amino acid sequence having a 70% identity or more with amino acids 1-221 of SEQ ID NO: 10,
[6] a protein selected from:
(i) a protein comprising amino acids 1-319 of SEQ ID NO: 12;
(ii) an endoglucanase comprising an amino acid sequence in which one or plural amino acids are deleted, substituted, and/or added in amino acids 1-319 of SEQ ID NO: 12; or
(iii) an endoglucanase comprising an amino acid sequence having a 70% identity or more with amino acids 1-319 of SEQ ID NO: 12,
[7] a protein selected from:
(i) a protein comprising amino acids 1-301 of SEQ ID NO: 14;
(ii) an endoglucanase comprising an amino acid sequence in which one or plural amino acids are deleted, substituted, and/or added in amino acids 1-301 of SEQ ID NO: 14; or
(iii) an endoglucanase comprising an amino acid sequence having a 70% identity or more with amino acids 1-301 of SEQ ID NO: 14,
[8] a protein selected from:
(i) a protein comprising amino acids 1-458 of SEQ ID NO: 16;
(ii) a β-glucosidase comprising an amino acid sequence in which one or plural amino acids are deleted, substituted, and/or added in amino acids 1-458 of SEQ ID NO: 16; or
(iii) a β-glucosidase comprising an amino acid sequence having a 70% identity or more with amino acids 1-458 of SEQ ID NO: 16,
[9] a protein selected from:
(i) a protein comprising amino acids 1-457 of SEQ ID NO: 18;
(ii) a β-glucosidase comprising an amino acid sequence in which one or plural amino acids are deleted, substituted, and/or added in amino acids 1-457 of SEQ ID NO: 18; or
(iii) a β-glucosidase comprising an amino acid sequence having a 70% identity or more with amino acids 1-457 of SEQ ID NO: 18,
[10] the protein of any one of [1] to [9], wherein the protein is derived from a filamentous fungus,
[11] the protein of [10], wherein the filamentous fungus is *Acremonium cellulolyticus*,
[12] a polynucleotide comprising a nucleotide sequence encoding the protein of any one of [1] to [9],
[13] a DNA comprising the nucleotide sequence of SEQ ID NO: 1, or a modified sequence thereof,
[14] a DNA selected from:
(i) a DNA encoding the protein of [1];
(ii) a DNA comprising nucleotides 136-1437 of SEQ ID NO: 1; or
(iii) a DNA hybridizing under stringent conditions to a DNA consisting nucleotides 136-1437 of SEQ ID NO: 1, and encoding a protein having endoglucanase activity,
[15] the DNA wherein an intron sequence is removed from the DNA of [14],
[16] the DNA of [15], wherein the intron sequence comprises one or more sequences selected from nucleotides 233-291, 351-425, 579-631, 697-754, or 853-907 of SEQ ID NO: 1,
[17] the DNA wherein a nucleotide sequence encoding a signal sequence is removed from the DNA of any one of [13] to [16],
[18] the DNA of [17], wherein the nucleotide sequence encoding a signal sequence is nucleotides 136-216 of SEQ ID NO: 1,
[19] a DNA comprising the nucleotide sequence of SEQ ID NO: 3, or a modified sequence thereof,
[20] a DNA selected from:
(i) a DNA encoding the protein of [2];
(ii) a DNA comprising nucleotides 128-1615 of SEQ ID NO: 3; or
(iii) a DNA hybridizing under stringent conditions to a DNA consisting nucleotides 128-1615 of SEQ ID NO: 3, and encoding a protein having endoglucanase activity,
[21] the DNA wherein a nucleotide sequence encoding a signal sequence is removed from the DNA of any one of [19] to [20],
[22] the DNA of [21], wherein the nucleotide sequence encoding a signal sequence is nucleotides 128-187 of SEQ ID NO: 3,
[23] a DNA comprising the nucleotide sequence of SEQ ID NO: 5, or a modified sequence thereof,
[24] a DNA selected from:
(i) a DNA encoding the protein of [3];
(ii) a DNA comprising nucleotides 169-1598 of SEQ ID NO: 5; or
(iii) a DNA hybridizing under stringent conditions to a DNA consisting nucleotides 169-1598 of SEQ ID NO: 5, and encoding a protein having endoglucanase activity,
[25] the DNA wherein an intron sequence is removed from the DNA of [24],
[26] the DNA of [25], wherein the intron sequence comprises one or more sequences selected from nucleotides 254-309, 406-461, or 1372-1450 of SEQ ID NO: 5,
[27] the DNA wherein a nucleotide sequence encoding a signal sequence is removed from the DNA of any one of [23] to [26],

[28] the DNA of [27], wherein the nucleotide sequence encoding a signal sequence is nucleotides 169-231 of SEQ ID NO: 5,
[29] a DNA comprising the nucleotide sequence of SEQ ID NO: 7, or a modified sequence thereof,
[30] a DNA selected from:
(i) a DNA encoding the protein of [4];
(ii) a DNA comprising nucleotides 70-1376 of SEQ ID NO: 7; or
(iii) a DNA hybridizing under stringent conditions to a DNA consisting nucleotides 70-1376 of SEQ ID NO: 7, and encoding a protein having endoglucanase activity,
[31] the DNA wherein an intron sequence is removed from the DNA of [30],
[32] the DNA of [31], wherein the intron sequence comprises one or more sequences selected from nucleotides 451-500 or 765-830 of SEQ ID NO: 7,
[33] the DNA wherein a nucleotide sequence encoding a signal sequence is removed from the DNA of any one of [29] to [32],
[34] the DNA of [33], wherein the nucleotide sequence encoding a signal sequence is nucleotides 70-129 of SEQ ID NO: 7,
[35] a DNA comprising the nucleotide sequence of SEQ ID NO: 9, or a modified sequence thereof,
[36] a DNA selected from:
(i) a DNA encoding the protein of [5];
(ii) a DNA comprising nucleotides 141-974 of SEQ ID NO: 9; or
(iii) a DNA hybridizing under stringent conditions to a DNA consisting nucleotides 141-974 of SEQ ID NO: 9, and encoding a protein having endoglucanase activity,
[37] the DNA wherein an intron sequence is removed from the DNA of [36],
[38] the DNA of [37], wherein the intron sequence comprises one or more sequences selected from nucleotides 551-609 or 831-894 of SEQ ID NO: 9,
[39] the DNA wherein a nucleotide sequence encoding a signal sequence is removed from the DNA of any one of [35] to [38],
[40] the DNA of [39], wherein the nucleotide sequence encoding a signal sequence is nucleotides 141-185 of SEQ ID NO: 9,
[41] a DNA comprising the nucleotide sequence of SEQ ID NO: 11, or a modified sequence thereof,
[42] a DNA selected from:
(i) a DNA encoding the protein of [6];
(ii) a DNA comprising nucleotides 114-1230 of SEQ ID NO: 11; or
(iii) a DNA hybridizing under stringent conditions to a DNA consisting nucleotides 114-1230 of SEQ ID NO: 11, and encoding a protein having endoglucanase activity,
[43] the DNA wherein an intron sequence is removed from the DNA of [42],
[44] the DNA of [43], wherein the intron sequence comprises one or more sequences selected from nucleotides 183-232 or 299-357 of SEQ ID NO: 11,
[45] the DNA wherein a nucleotide sequence encoding a signal sequence is removed from the DNA of any one of [41] to [44],
[46] the DNA of [45], wherein the nucleotide sequence encoding a signal sequence is nucleotides 114-161 of SEQ ID NO: 11,
[47] a DNA comprising the nucleotide sequence of SEQ ID NO: 13, or a modified sequence thereof,
[48] a DNA selected from:
(i) a DNA encoding the protein of [7]
(ii) a DNA comprising nucleotides 124-1143 of SEQ ID NO: 13; or
(iii) a DNA hybridizing under stringent conditions to a DNA consisting nucleotides 124-1143 of SEQ ID NO: 13, and encoding a protein having endoglucanase activity,
[49] the DNA wherein an intron sequence is removed from the DNA of [48],
[50] the DNA of [49], wherein the intron sequence comprises one or more sequences selected from nucleotides 225-275 of SEQ ID NO: 13,
[51] the DNA wherein a nucleotide sequence encoding a signal sequence is removed from the DNA of any one of [47] to [50],
[52] the DNA of [51], wherein the nucleotide sequence encoding a signal sequence is nucleotides 124-186 of SEQ ID NO: 13,
[53] a DNA comprising the nucleotide sequence of SEQ ID NO: 15, or a modified sequence thereof,
[54] a DNA selected from:
(i) a DNA encoding the protein of [8];
(ii) a DNA comprising nucleotides 238-1887 of SEQ ID NO: 15; or
(iii) a DNA hybridizing under stringent conditions to a DNA consisting nucleotides 238-1887 of SEQ ID NO: 15, and encoding a protein having β-glucosidase activity,
[55] the DNA wherein an intron sequence is removed from the DNA of [54],
[56] the DNA of [55], wherein the intron sequence comprises one or more sequences selected from nucleotides 784-850, 1138-1205, or 1703-1756 of SEQ ID NO: 15,
[57] the DNA wherein a nucleotide sequence encoding a signal sequence is removed from the DNA of any one of [53] to [56],
[58] the DNA of [57], wherein the nucleotide sequence encoding a signal sequence is nucleotides 238-321 of SEQ ID NO: 15,
[59] a DNA comprising the nucleotide sequence of SEQ ID NO: 17, or a modified sequence thereof,
[60 a DNA selected from:
(i) a DNA encoding the protein of [9];
(ii) a DNA comprising nucleotides 66-1765 of SEQ ID NO: 17; or
(iii) a DNA hybridizing under stringent conditions to a DNA consisting nucleotides 66-1765 of SEQ ID NO: 17, and encoding a protein having β-glucosidase activity,
[61] the DNA wherein an intron sequence is removed from the DNA of [60],
[62] the DNA of [61], wherein the intron sequence comprises one or more sequences selected from nucleotides 149-211, 404-460, 934-988, or 1575-1626 of SEQ ID NO: 17,
[63] the DNA wherein a nucleotide sequence encoding a signal sequence is removed from the DNA of any one of [59] to [62],
[64] the DNA of [63], wherein the nucleotide sequence encoding a signal sequence is nucleotides 66-227 of SEQ ID NO: 17,
[65] an expression vector, comprising the DNA of any one of [12] to [64],
[66] a host cell transformed with the expression vector of [65],
[67] the host cell of [66], wherein the host cell is a yeast or a filamentous fungus,
[68] the host cell of [67], wherein the yeast is a microorganism belonging to genus *Saccharomyces*, *Hansenula*, or *Pichia*,

[69] the host cell of [68], wherein the yeast is *Saccharomyces cerevisiae*,
[70] the host cell of [67], wherein the filamentous fungus is a microorganism belonging to genus *Humicola, Aspergillus, Trichoderma, Fusarium*, or *Acremonium*,
[71] the host cell of [70], wherein the filamentous fungus is *Acremonium cellulolyticus, Humicola insolens, Aspergillus niger, Aspergillus oryzae, Trichoderma viride*, or *Fusarium oxysporum*,
[72] a filamentous fungus belonging to genus *Acremonium*, which is deficient in a gene corresponding to the DNA of any one of [12] to [64] by homologous recombination,
[73] the filamentous fungus of [72], wherein the filamentous fungus is *Acremonium cellulolyticus*,
[74] a process of producing the protein of any one of [1] to [9], comprising:
cultivating the host cells of any one of [66] to [73]; and
collecting the protein from the host cells and/or its culture,
[75] a protein produced by the process of [74],
[76] a cellulase preparation comprising the protein of any one of [1] to [9] and [75],
[77] a method of saccharifying biomass, comprising:
bringing cellulose-containing biomass into contact with the protein of any one of [1] to [9] and [75] or the cellulase preparation of [76],
[78] a method of treating a cellulose-containing fabric, comprising:
bringing the cellulose-containing fabric into contact with the protein of any one of [1] to [9] and [75] or the cellulase preparation of [76],
[79] a method of deinking waste paper, characterized by using the protein of any one of [1] to [9] and [75] or the cellulase preparation of [76], in the process of treating the waste paper together with a deinking agent,
[80] a method of improving a water freeness of paper pulp, comprising:
treating the paper pulp with the protein of any one of [1] to [9] and [75] or the cellulase preparation of [76], and
[81] a method of improving a digestibility of animal feed, comprising:
treating the animal feed with the protein of any one of [1] to [9] and [75] or the cellulase preparation of [76].

Advantageous Effects of Invention

According to the present invention, it is possible to obtain DNAs which are needed to efficiently produce specific endoglucanases and β-glucosidases derived from *Acremonium cellulolyticus* as recombinant proteins, and to obtain recombinant microorganisms which can efficiently express these cellulase components. Further, specific endoglucanases and β-glucosidases can be efficiently produced at low cost.

According to the present invention, specific endoglucanase and β-glucosidase genes can be disrupted from the genome of *Acremonium cellulolyticus*, and as a result, it is possible to obtain recombinant *Acremonium cellulolyticus* which produces cellulase not containing the endoglucanase and β-glucosidase, and to produce the cellulase not containing the specific endoglucanase and β-glucosidase.

A cellulose-based substrate can be efficiently degraded at low cost by selecting an optimum cellulase group from various cellulases obtained in the present invention, and treating the cellulose-based substrate with the cellulase group.

DESCRIPTION OF EMBODIMENTS

Endoglucanase and β-Glucosidase

Figure 1:
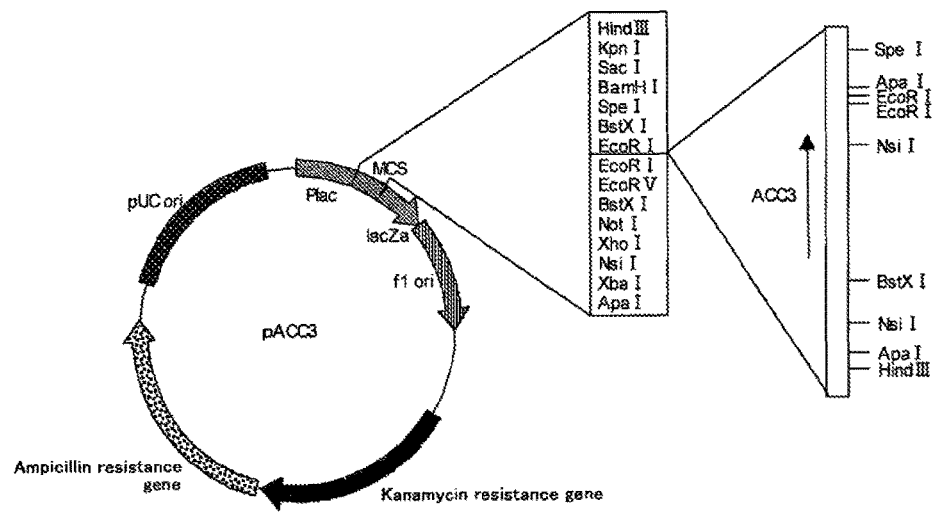
FIG. 1 is a restriction map of plasmid pACC3.
Figure 2:
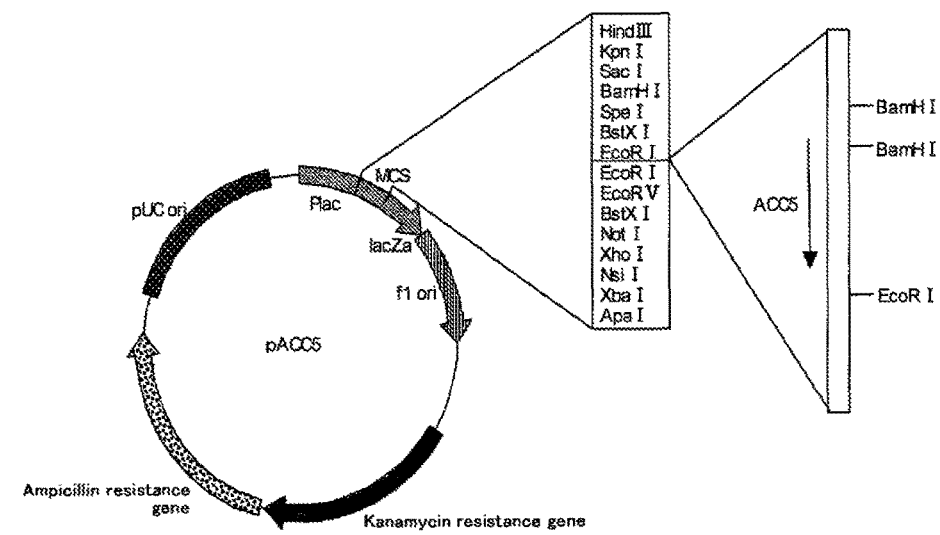
FIG. 2 is a restriction map of plasmid pACC5.
Figure 3:
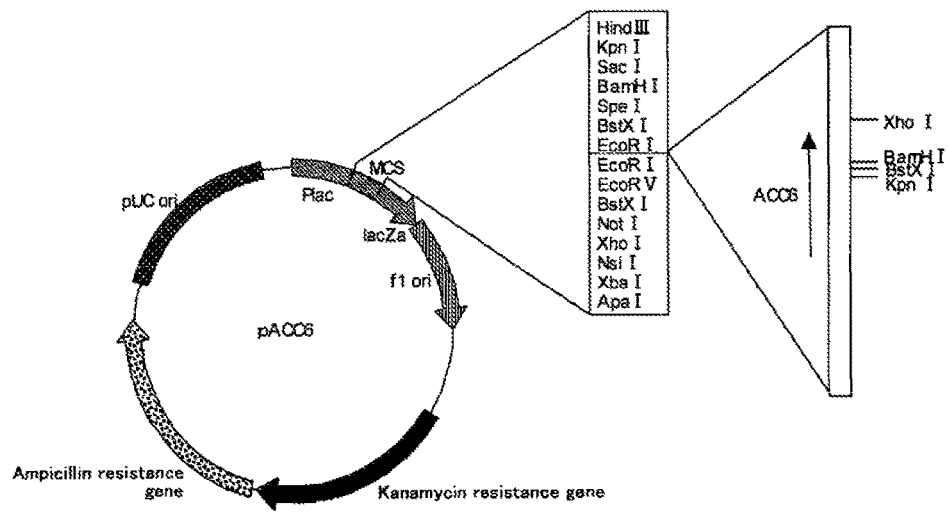
FIG. 3 is a restriction map of plasmid pACC6.
Figure 4:
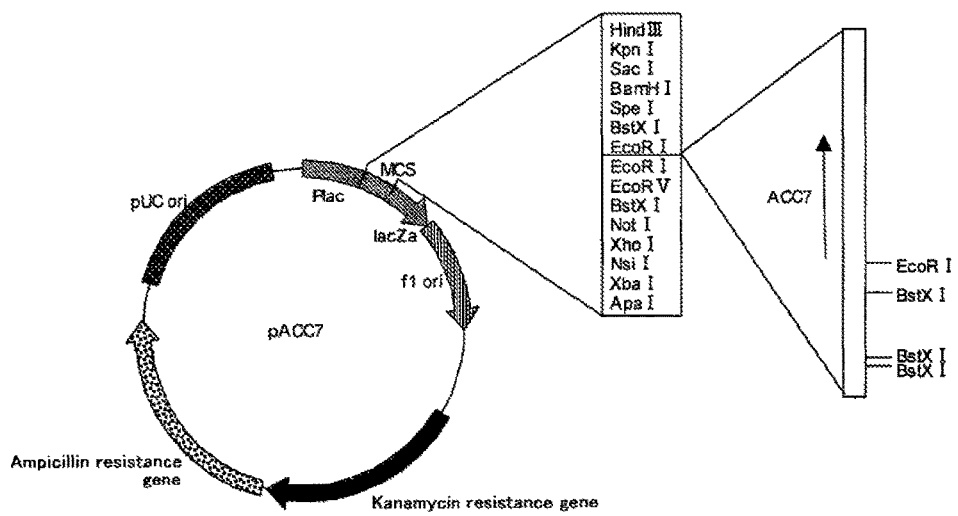
FIG. 4 is a restriction map of plasmid pACC7.
Figure 5:
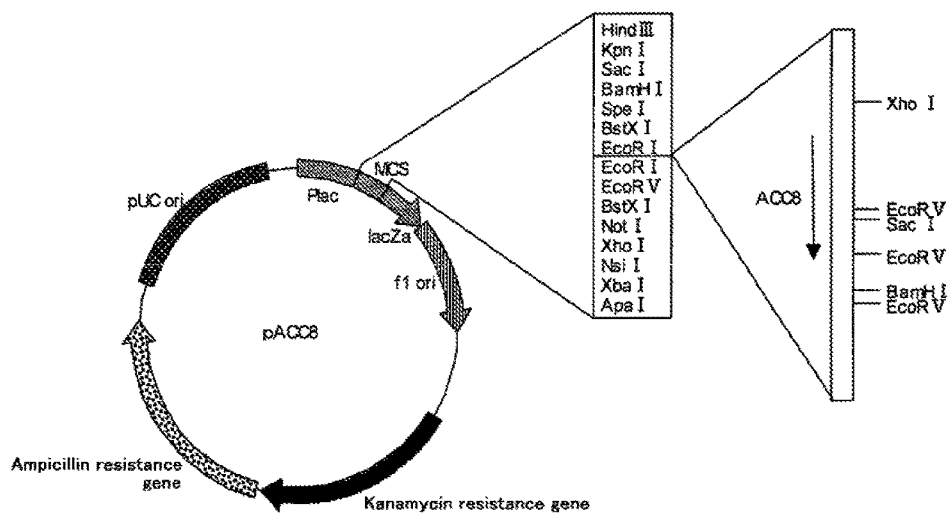
FIG. 5 is a restriction map of plasmid pACC8.
Figure 6:
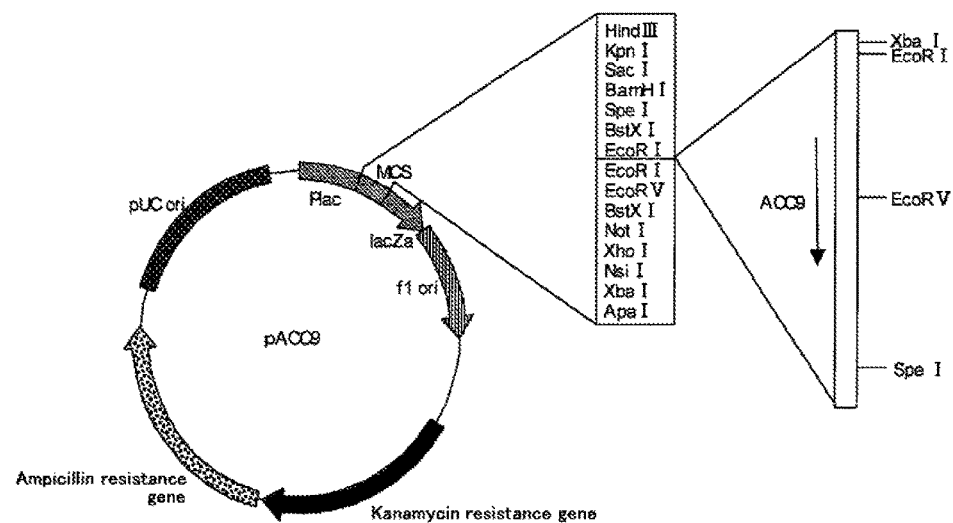
FIG. 6 is a restriction map of plasmid pACC9.
Figure 7:
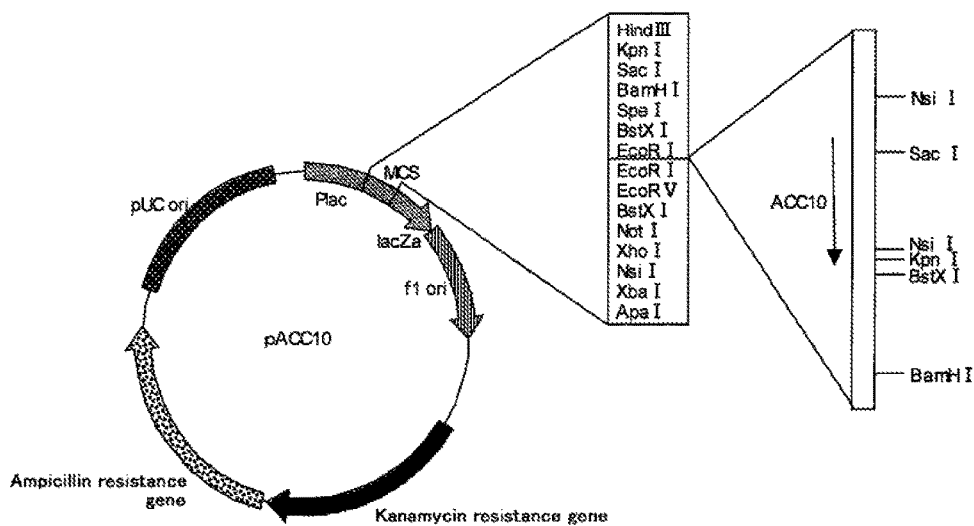
FIG. 7 is a restriction map of plasmid pACC10.
Figure 8:
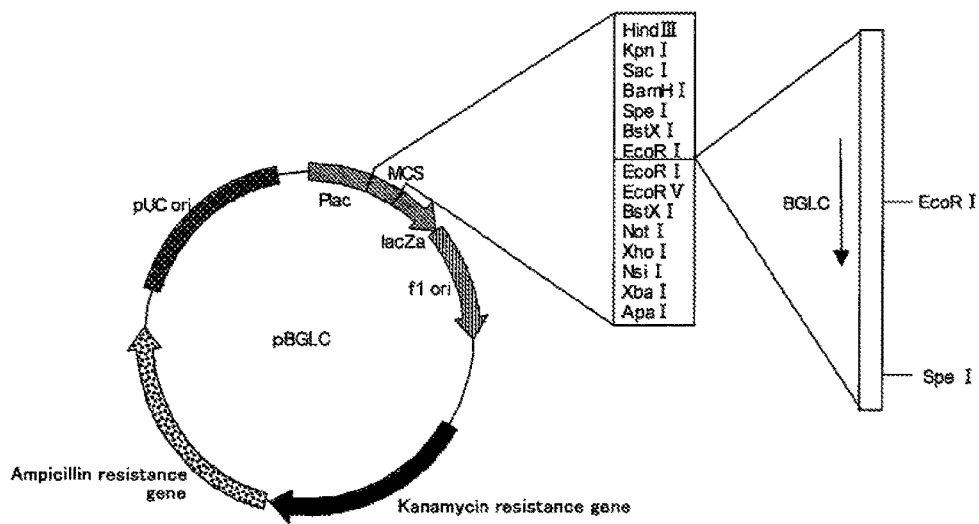
FIG. 8 is a restriction map of plasmid pBGLC.
Figure 9:
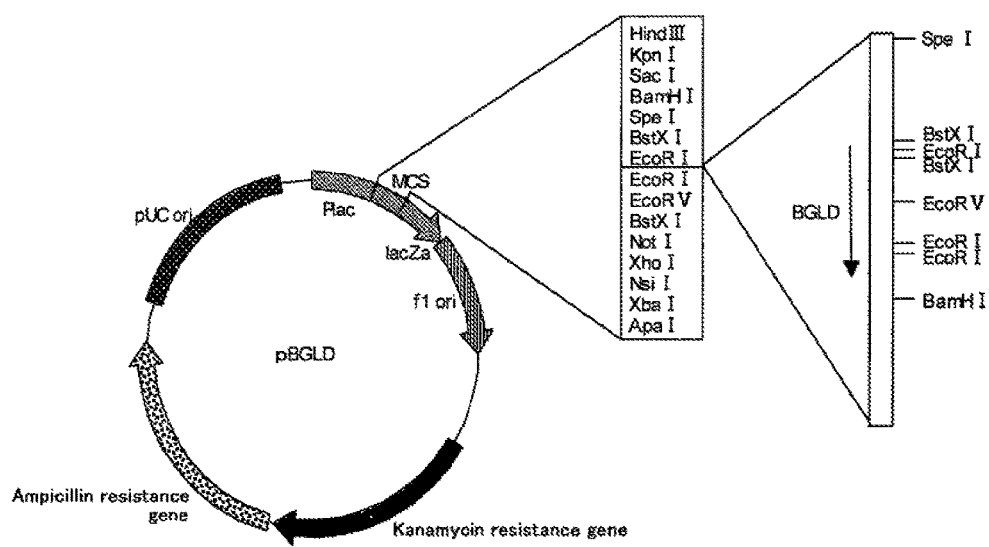
FIG. 9 is a restriction map of plasmid pBGLD.

The protein of the present invention, endoglucanases and β-glucosidases, may comprise a sequence corresponding to the mature protein portion of an amino acid sequence selected from SEQ ID NOS: 2, 4, 6, 8, 10, 12, 14, 16, and 18, or an amino acid sequence substantially equivalent to the amino acid sequence.

The term "amino acid sequence substantially equivalent" as used herein means, for example, an amino acid sequence in which there is a modification by the substitution, deletion, and/or addition of one or plural (preferably several) amino acids but the polypeptide activity is not affected, or an amino acid sequence in which it has a 70% identity or more but the polypeptide activity is not affected.

The number of amino acid residues modified is preferably 1 to 40, more preferably 1 to several, still more preferably 1 to 8, and most preferably 1 to 4. Examples of "modification which does not affect the activity" as used herein include conservative substitution. The term "conservative substitution" means one or plural amino acid residues are replaced with different amino acids having similar chemical properties without substantial change in the activity of a polypeptide. Examples of the conservative substitution include a substitution of a hydrophobic residue for another hydrophobic residue, and a substitution of a polar residue for another polar residue having the same charge. Amino acids which have similar chemical properties and can be conservatively substituted with each other are known to those skilled in the art. More particularly, examples of nonpolar (hydrophobic) amino acids include alanine, valine, isoleucine, leucine, proline, tryptophan, phenylalanine, and methionine. Examples of polar (neutral) amino acids include glycine, serine, threonine, tyrosine, glutamine, asparagine, and cysteine. Examples of basic amino acids having a positive charge include arginine, histidine, and lysine. Examples of acidic amino acids having a negative charge include aspartic acid and glutamic acid.

The term "identity" as used herein means a value calculated by FASTA3 [Science, 227, 1435-1441 (1985); Proc. Natl. Acad. Sci. USA, 85, 2444-2448 (1988); http://www.ddbj.nig.ac.jp/E-mail/homology-j.html], a homology search program known to those skilled in the art, using default parameters. It may be an identity of, preferably 80% or more, more preferably 90% or more, still more preferably 95% or more, still more preferably 98% or more, and most preferably 99% or more.

In the protein of the present invention, a polypeptide sequence which does not affect the enzymatic activity of the protein may be added to the N-terminus and/or the C-terminus of the amino acid corresponding to its mature portion or an amino acid substantially equivalent thereto. Examples of the polypeptide sequence include a signal sequence, a detection marker (for example, a FLAG tag), and a polypeptide for purification [for example, glutathione S-transferase (GST)].

Endoglucanase and β-Glucosidase Genes

The polynucleotide of the present invention, endoglucanase and β-glucosidase genes, may comprise a nucleotide sequence encoding the protein of the present invention; a nucleotide sequence selected from the sequences of nucleotides 136-1437 of SEQ ID NO: 1, nucleotides 128-1615 of SEQ ID NO: 3, nucleotides 169-1598 of SEQ ID NO: 5, nucleotides 70-1376 of SEQ ID NO: 7, nucleotides 141-974 of SEQ ID NO: 9, nucleotides 114-1230 of SEQ ID NO: 11, nucleotides 124-1143 of SEQ ID NO: 13, nucleotides 238-1887 of SEQ ID NO: 15, and nucleotides 66-1765 of SEQ ID NO: 17; or a nucleotide sequence which can hybridize to these nucleotides under stringent conditions.

The term "under stringent conditions" as used herein means that a membrane after hybridization is washed at a high temperature in a solution of low salt concentration, for example, at 60° C. for 20 minutes in a solution of 2×SSC (1×SSC: 15 mmol/L trisodium citrate and 150 mmol/L sodium chloride) containing 0.5% SDS.

Cloning of Endoglucanase and β-Glucosidase Genes

The endoglucanase and β-glucosidase genes of the present invention may be isolated from *Acremonium cellulolyticus* or its mutant strain, for example, by the following method. Since the nucleotide sequences are disclosed in the present specification, they may be chemically-synthesized artificially.

Genomic DNA is extracted from *Acremonium cellulolyticus* mycelia by a conventional method. The genomic DNA is digested with an appropriate restriction enzyme, and ligated with an appropriate vector to prepare a genomic DNA library of *Acremonium cellulolyticus*. Various vectors, for example, a plasmid vector, a phage vector, a cosmid vector, or a BAC vector, may be used as the vector.

Next, appropriate probes may be prepared based on the nucleotide sequences of the endoglucanase and β-glucosidase genes disclosed in the present specification, and DNA fragments containing desired endoglucanase and β-glucosidase genes may be isolated from the genomic DNA library by hybridization. Alternatively, a desired gene may be isolated by preparing primers capable of amplifying the desired gene, based on the nucleotide sequences of the endoglucanase and β-glucosidase genes disclosed in the present specification, performing PCR using the genomic DNA of *Acremonium cellulolyticus* as a template, and ligating the amplified DNA fragment with an appropriate vector. Since the endoglucanase and β-glucosidase genes of the present invention are contained in plasmids pACC3, pACC5, pACC6, pACC7, pACC8, pACC9, pACC10, pBGLC, and pBGLD, these plasmids may be used as a template DNA for PCR. Further, desired DNA fragments may be prepared by digesting the plasmids with appropriate restriction enzymes.

Deposit of Microorganisms

*Escherichia coli* transformed with pACC3 (*Escherichia coli* TOP10/pACC3) was internationally deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Oct. 9, 2008. The international deposit number is FERM BP-11029.

*Escherichia coli* transformed with pACC5 (*Escherichia coli* TOP10/pACC5) was internationally deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Oct. 9, 2008. The international deposit number is FERM BP-11030.

*Escherichia coli* transformed with pACC6 (*Escherichia coli* TOP10/pACC6) was internationally deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Oct. 9, 2008. The international deposit number is FERM BP-11031.

*Escherichia coli* transformed with pACC7 (*Escherichia coli* TOP10/pACC7) was internationally deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Oct. 9, 2008. The international deposit number is FERM BP-11032.

*Escherichia coli* transformed with pACC8 (*Escherichia coli* TOP10/pACC8) was internationally deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Oct. 9, 2008. The international deposit number is FERM BP-11033.

*Escherichia coli* transformed with pACC9 (*Escherichia coli* TOP10/pACC9) was internationally deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Oct. 9, 2008. The international deposit number is FERM BP-11034.

*Escherichia coli* transformed with pACC10 (*Escherichia coli* TOP10/pACC10) was internationally deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Oct. 9, 2008. The international deposit number is FERM BP-11035.

*Escherichia coli* transformed with pBGLC (*Escherichia coli* TOP10/pBGLC) was internationally deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Oct. 9, 2008. The international deposit number is FERM BP-11036.

*Escherichia coli* transformed with pBGLD (*Escherichia coli* TOP10/pBGLD) was internationally deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Oct. 9, 2008. The international deposit number is FERM BP-11037.

Expression Vector and Transformed Microorganism

According to the present invention, an expression vector comprising a DNA comprising a nucleotide sequence encoding the amino acid sequence of SEQ ID NO: 2, 4, 6, 8, 10, 12, 14, 16, or 18, or its modified amino acid sequence (hereinafter simply referred to the DNA sequence of the present invention), in which the DNA can be replicated in a host microorganism and a protein encoded by the DNA can be expressed, is provided. The expression vector may be constructed based on a self-replicating vector such as plasmid, which exists as an extra-chromosomal independent body and does not depend on the replication of the chromosome. The expression vector may be one which may be incorporated into the genome of a host microorganism, when it is transformed with the expression vector, and which may be replicated together with the replication of the chromosome. The expression vector of the present invention may be constructed in accordance with procedures and methods widely used in the field of genetic engineering.

The expression vector of the present invention preferably includes not only the DNA of the present invention, but also a DNA sequence capable of regulating the expression of the DNA, a genetic marker to select a transformant, or the like, to express a protein having a desired activity by incorporating the expression vector into a host microorganism. Examples of the DNA sequence capable of regulating the expression include a promoter, a terminator, and a DNA sequence encoding a signal peptide. The promoter is not limited, so long as it shows a transcriptional activity in a host microorganism, and may be obtained as a DNA sequence which regulates the expression of a gene encoding a protein from a species the same as or different from the microorganism. The signal peptide is not limited, so long as it contributes to the secretion of a protein in a host microorganism, and may be obtained as a DNA sequence which is derived from a gene encoding a protein from a species the same as or different from the microorganism. The genetic marker in the present invention may be appropriately selected in accordance with a method for selecting transformants, and examples thereof include a gene encoding a drug resistance, and a gene which complements auxotrophy.

According to the present invention, a microorganism transformed with the expression vector is provided. The host-vector system is not limited, and for example, a system using *Escherichia coli*, actinomycetes, yeast, filamentous fungi, or the like, or a system using the same to express a protein fused with other protein, may be used.

Transformation of a microorganism with the expression vector may be carried out in accordance with techniques widely used in this field.

Further, the protein of the present invention may be obtained by cultivating the resulting transformant in an appropriate medium, and isolating it from the culture. Therefore, according to another embodiment of the present invention, a process of producing the novel protein of the present invention is provided. The cultivation of the transformant and its conditions may be essentially the same as those of the microorganism used. After the cultivation of the transformant, the protein of interest can be recovered by a method widely used in this field.

According to a preferred embodiment of the present invention, a yeast cell capable of expressing endoglucanase or β-glucosidase enzyme encoded by the DNA sequence of the present invention is provided. Examples of the yeast cell in the present invention include a microorganism belonging to genus *Saccharomyces, Hansenula*, or *Pichia*, such as *Saccharomyces cerevisiae*.

The host filamentous fungus in the present invention may be a microorganism belonging to genus *Humicola, Aspergillus, Trichoderma, Fusarium*, or *Acremonium*. Preferred examples thereof include *Humicola insolens, Aspergillus niger, Aspergillus oryzae, Trichoderma viride, Fusarium oxysporum*, or *Acremonium cellulolyticus*.

Expression of specific endoglucanase or β-glucosidase may be suppressed by incorporating the gene of the present invention, which ligates with an appropriate vector, into *Acremonium cellulolyticus* to suppress the expression, or by disrupting the gene using homologous recombination to disrupt its function. The gene disruption utilizing homologous recombination may be carried out in accordance with a widely used method, and the construction of vector for gene disruption and the incorporation thereof into a host are obvious to those skilled in the art.

Preparation of Cellulase

The protein of the present invention may be obtained by cultivating the resulting transformant in an appropriate medium, and isolating it from the culture. The cultivation of the transformant and its conditions may be appropriately selected in accordance with the microorganism used. The collection and purification of the protein of interest from the culture may be carried out in accordance with a conventional method.

Cellulase Preparation

According to another embodiment of the present invention, a cellulase preparation containing the protein (cellulase) of the present invention is provided. The cellulase preparation of the present invention may be produced by mixing the cellulase of the present invention with a generally-contained component, for example, an excipient (for example, lactose, sodium chloride, or sorbitol), a surfactant, or a preservative. The cellulase preparation of the present invention may be prepared in an appropriate form, such as powder or liquid.

Use of Cellulase

According to the present invention, it is considered that biomass saccharification may be efficiently improved by treating biomass with the cellulase enzyme (group) or cellulase preparation of the present invention. According to the present invention, a method of improving biomass saccharification, comprising the step of treating biomass with the cellulase enzyme (group) or cellulase preparation of the present invention, is provided. Examples of the biomass which may be treated with the present invention include rice straw, bagasse, corn stover, pomace of fruit such as coconut, and wood waste, and materials obtained by appropriately pretreating the same.

According to the present invention, a method of clearing color of a colored cellulose-containing fabric, comprising the step of treating the colored cellulose-containing fabric with the cellulase enzyme (group) or cellulase preparation, and a method of providing a localized variation in color of a colored cellulose-containing fabric, i.e., a method of giving a stone wash appearance to the colored cellulose-containing fabric. This method comprises the step of treating the colored cellulose-containing fabric with the cellulase enzyme (group) or cellulase preparation of the present invention.

According to the present invention, it is considered that a water freeness of paper pulp may be efficiently improved by treating the paper pulp with the endoglucanase enzyme of the present invention without remarkable reduction in strength. Therefore, according to the present invention, a method of improving a water freeness of paper pulp, comprising the step of treating the paper pulp with the endoglucanase enzyme or cellulase preparation of the present invention, is provided. Examples of the pulp which may be treated with the present invention include waste paper pulp, recycled board pulp, kraft pulp, sulfite pulp, and thermomechanical treatment and other high yield pulp.

Further, the digestibility of glucan in animal feed may be improved by using the endoglucanase of the present invention in animal feed. Therefore, according to the present invention, a method of improving a digestibility of animal feed, comprising the step of treating the animal feed with the endoglucanase enzyme or cellulase preparation of the present invention, is provided.

EXAMPLES

The present invention now will be further illustrated by, but is by no means limited to, the following Example.

Example 1: Cloning of ACC3 Gene (1-1) Isolation of Genomic DNA

*Acremonium cellulolyticus* ACCP-5-1 was cultivated in an (s) medium (2% bouillon, 0.5% yeast extract, and 2% glucose) at 32° C. for 2 days, and centrifuged to collect mycelia. Genomic DNA was isolated from the obtained mycelia in accordance with the method of Horiuchi et al. (H. Horiuchi et al., J. Bacteriol., 170, 272-278, (1988)).

(1-2) Cloning of ACC3 Gene Fragment

The following primers were prepared based on the sequences of known endoglucanases which were classified into Glycoside Hydrolase family 5.

```
ACC3-F:   GGGCGTCTGTRTTYGARTGT (SEQ ID NO: 19)

ACC3-R:   AAAATGTAGTCTCCCCACCA (SEQ ID NO: 20)
```

PCR was carried out using ACC3-F and ACC3-R as primers and genomic DNA as a template, and using LA Taq polymerase (Takara Bio). The PCR was carried out by repeating a cycle consisting of a reaction at 94° C. for 30 seconds, annealing for 30 seconds, and a reaction at 72° C. for 1 minute 40 times. The annealing temperature was lowered stepwisely from 63° C. to 53° C. in the first 20 cycles, and maintained at 53° C. in the subsequent 20 cycles. The amplified DNA fragment of 1 kbp was inserted into a pCR2.1-TOPO plasmid vector using a TOPO TA cloning kit (Invitrogen) in accordance with a protocol attached to the kit to obtain plasmid TOPO-pACC3-partial.

The inserted DNA fragment cloned into plasmid TOPO-pACC3-partial was sequenced using a BigDye Terminator v3.1 Cycle Sequencing Kit (Applied Biosystems) and an ABI PRISM genetic analyzer (Applied Biosystems) in accordance with protocols attached thereto. The obtained nucleotide sequence was translated into the amino acid sequence, and a homology search was carried out using the amino acid sequence. The sequence showed a 74% identity with that of endoglucanase EG1 (Q8WZD7) derived from *Talaromyces emersonii*, and thus, it was judged that the DNA fragment was part of an endoglucanase (Glycoside Hydrolase family 5) gene.

(1-3) Cloning of Full-Length of ACC3 Gene by Inverse PCR

Inverse PCR was carried out in accordance with the method of Triglia et al. (T Triglia et al., Nucleic Acids Research, 16, 8186, (1988)). Genomic DNA from *Acremonium cellulolyticus* was digested with SalI overnight, and circular DNA was prepared using Mighty Mix (Takara Bio). PCR was carried out using the circular DNA as a template and the following sequences contained in the ACC3 gene fragment as primers to obtain the 5' upstream region and the 3' downstream region of the ACC3 gene.

```
ACC3-inv-F:   ACTTCCAGACTTTCTGGTCC (SEQ ID NO: 21)

ACC3-inv-R:   AGGCCGAGAGTAAGTATCTC (SEQ ID NO: 22)
```

The 5' upstream region and the 3' downstream region were sequenced in accordance with the method described in Example 1-2 to determine the complete nucleotide sequence of the ACC3 gene.

The following primers were prepared based on the nucleotide sequence obtained by the inverse PCR, and PCR was carried out using genomic DNA as a template to amplify the ACC3 gene.

```
pACC3-F:   GAAGGATGGTAGATTGTCCG (SEQ ID NO: 23)

pACC3-R:   ACCGAGAAGGATTTCTCGCA (SEQ ID NO: 24)
```

The amplified DNA was inserted into a pCR2.1-TOPO plasmid vector using a TOPO TA cloning kit (Invitrogen) to obtain plasmid pACC3. *Escherichia coli* TOP10 (Invitrogen) was transformed with the obtained plasmid pACC3 to obtain *Escherichia coli* TOP10/pACC3.

(1-4) Preparation of cDNA and Intron Analysis of ACC3 Gene

*Acremonium cellulolyticus* ACCP-5-1 was cultivated in a cellulase induction medium at 32° C. for 2 days, and centrifuged to collect mycelia. The obtained mycelia were frozen in liquid nitrogen, and ground with a mortar and pestle. Total RNA was isolated from the ground mycelia using ISOGEN (Nippon Gene) in accordance with a protocol attached thereto. Further, mRNA was purified from the total RNA using a mRNA Purification kit (Pharmacia) in accordance with a protocol attached thereto.

cDNA was synthesized from the obtained mRNA using a TimeSaver cDNA Synthesis kit (Pharmacia) in accordance with a protocol attached thereto. The following primers containing the initiation codon and the stop codon were prepared based on the ACC3 gene sequence, and PCR was carried out using the cDNA as a template to amplify the ACC3 cDNA gene.

```
                                       (SEQ ID NO: 25)
ACC3-N:  ATGAAGACCAGCATCATTTCTATC (SEQ ID NO: 26)
ACC3-C:  TCATGGGAAATAACTCTCCAGAAT
```

The ACC3 cDNA gene was sequenced in accordance with the method described in Example 1-2, and compared with the pACC3 gene to determine the location of introns.

(1-5) Deduction of Amino Acid Sequence of ACC3

The endoglucanase ACC3 gene isolated from *Acremonium cellulolyticus* by the method described above consisted of 1302 bp nucleotides corresponding to nucleotides 136-1437 of SEQ ID NO: 1. It was found that the ACC3 gene contained five introns at positions 233-291, 351-425, 579-631, 697-754, and 853-907 of SEQ ID NO: 1. The amino acid sequence of ACC3 deduced from the open reading frame (ORF) was that of SEQ ID NO: 2. It was assumed using a signal sequence prediction software SignalP 3.0 that the amino acid sequence at position −27 to −1 of ACC3 was a signal sequence.

Example 2: Cloning of ACC5 Gene (2-1) Isolation of Genomic DNA and mRNA and Preparation of cDNA Genomic DNA of *Acremonium cellulolyticus* ACCP-5-1 was isolated in accordance with the method described in Example 1-1. cDNA of *Acremonium cellulolyticus* ACCP-5-1 was prepared in accordance with the method described in Example 1-4

(2-2) Cloning of ACC5 Gene Fragment

The following primers were prepared based on the N-terminal amino acid sequences of known endoglucanases which were classified into Glycoside Hydrolase family 7 and the poly A nucleotide sequence.

```
                                            (SEQ ID NO: 27)
ACC5-F:  CAGCAGGCCCCCACCCCNGAYAAYYTNGC (SEQ ID NO: 28)
ACC5-R:  AATTCGCGGCCGCTAAAAAAAAA
```

PCR was carried out using ACC5-F and ACC5-R as primers and cDNA as a template, and using LA Taq polymerase (Takara Bio). The PCR was carried out by repeating a cycle consisting of a reaction at 94° C. for 30 seconds, annealing for 30 seconds, and a reaction at 72° C. for 1 minute 40 times. The annealing temperature was lowered stepwise from 63° C. to 53° C. in the first 20 cycles, and maintained at 53° C. in the subsequent 20 cycles. The amplified DNA fragment of 1.5 kbp was inserted into a pCR2.1-TOPO plasmid vector using a TOPO TA cloning kit (Invitrogen) in accordance with a protocol attached to the kit to obtain plasmid TOPO-pACC5-partial.

The inserted DNA fragment cloned into plasmid TOPO-pACC5-partial was sequenced, and the obtained nucleotide sequence was translated into the amino acid sequence, and a homology search was carried out using the amino acid sequence. The sequence showed a 60% identity with that of endoglucanase (Q4WCM9) derived from *Aspergillus fumigatus*, and thus, it was judged that the DNA fragment was part of an endoglucanase (Glycoside Hydrolase family 7) gene.

(2-3) Cloning of Full-Length of ACC5 Gene by Inverse PCR

In accordance with the method described in Example 1-3, PCR was carried out using circular DNA (obtained by digestion with HindIII) as a template and the following sequences contained in the ACC5 gene fragment as primers to obtain the 5' upstream region and the 3' downstream region of the ACC5 gene.

```
                                            (SEQ ID NO: 29)
ACC5-inv-F:  ATCTCACCTGCAACCTACGA (SEQ ID NO: 30)
ACC5-inv-R:  CCTCTTCCGTTCCACATAAA
```

The 5' upstream region and the 3' downstream region were sequenced to determine the complete nucleotide sequence of the ACC5 gene.

The following primers were prepared based on the nucleotide sequence obtained by the inverse PCR, and PCR was carried out using genomic DNA as a template to amplify the ACC5 gene.

```
                                            (SEQ ID NO: 31)
pACC5-F:  ATTGCTCCGCATAGGTTCAA (SEQ ID NO: 32)
pACC5-R:  TTCAGAGTTAGTGCCTCCAG
```

The amplified DNA was inserted into a pCR2.1-TOPO plasmid vector using a TOPO TA cloning kit (Invitrogen) to obtain plasmid pACC5. *Escherichia coli* TOP10 (Invitrogen) was transformed with the obtained plasmid pACC5 to obtain *Escherichia coli* TOP10/pACC5.

(2-4) Intron Analysis of ACC5 Gene

The following primers containing the initiation codon and the stop codon were prepared based on the ACC5 gene sequence, and PCR was carried out using cDNA as a template to amplify the ACC5 cDNA gene.

```
                                            (SEQ ID NO: 33)
ACC5-N:  ATGGCGACTAGACCATTGGCTTTTG (SEQ ID NO: 34)
ACC5-C:  CTAAAGGCACTGTGAATAGTACGGA
```

The nucleotide sequence of the ACC5 cDNA gene was sequenced, and compared with the pACC5 gene to determine the location of introns.

(2-5) Deduction of Amino Acid Sequence of ACC5

The endoglucanase ACC5 gene isolated from *Acremonium cellulolyticus* by the method described above consisted of 1488 bp nucleotides corresponding to nucleotides 128-1615 of SEQ ID NO: 3. The amino acid sequence of ACC5 deduced from the open reading frame (ORF) was that of SEQ ID NO: 4. It was assumed using a signal sequence prediction software SignalP 3.0 that the amino acid sequence at position −20 to −1 of ACC5 was a signal sequence.

Example 3: Cloning of ACC6 Gene (3-1) Isolation of Genomic DNA and Preparation of Genomic Library Genomic DNA of *Acremonium cellulolyticus* ACCP-5-1 was isolated in accordance with the method described in Example 1-1. The isolated genomic DNA was partially digested with Sau3AI. The resulting product was ligated with BamHI arms of a phage vector dMBL3 cloning kit (Stratagene) using a ligation kit Ver. 2 (Takara Shuzo). The ligation mixture was subjected to ethanol precipitation, and the resulting precipitate was dissolved in a TE buffer. Phage particles were formed using the ligation mixture solution and a MaxPlax λ packaging kit (Epicenter Technologies), and *Escherichia coli* XL1-blue MRA(P2) was infected with the phage particles. A genomic DNA library of $1.1 \times 10^4$ phages was obtained by this method.

(3-2) Cloning of ACC6 Gene Fragment

The following primers were prepared based on the sequences of known endoglucanases which were classified into Glycoside Hydrolase family 5.

```
                                            (SEQ ID NO: 35)
ACC6-F:  GTGAACATCGCCGGCTTYGAYTTYGG (SEQ ID NO: 36)
ACC6-R:  CCGTTCCACCGGGCRTARTTRTG
```

PCR was carried out using ACC6-F and ACC6-R as primers and genomic DNA as a template, and using LA Taq polymerase (Takara Bio). The PCR was carried out by repeating a cycle consisting of a reaction at 94° C. for 30 seconds, annealing for 30 seconds, and a reaction at 72° C. for 1 minute 40 times. The annealing temperature was lowered stepwise from 63° C. to 53° C. in the first 20 cycles, and maintained at 53° C. in the subsequent 20 cycles. The amplified DNA fragment of 300 bp was inserted into a pCR2.1-TOPO plasmid vector using a TOPO TA cloning kit (Invitrogen) in accordance with a protocol attached to the kit to obtain plasmid TOPO-pACC6-partial.

The inserted DNA fragment cloned into plasmid TOPO-pACC6-partial was sequenced, and the obtained nucleotide sequence was translated into the amino acid sequence, and a homology search was carried out using the amino acid sequence. The sequence showed a 61% identity with that of endoglucanase EG3 (Q7Z7x2) derived from *Trichoderma viride*, and thus, it was judged that the DNA fragment was part of an endoglucanase (Glycoside Hydrolase family 5) gene. This DNA fragment was amplified by PCR using plasmid TOPO-pACC6-partial as a template in a similar fashion, and the obtained PCR product was labeled using an ECL Direct System (Amersham Pharmacia Biotech) to obtain a probe.

(3-3) Screening by Plaque Hybridization

The phage plaques prepared in Example 3-1 were transferred to a Hybond N+ nylon transfer membrane (Amersham). The membrane was subjected to alkaline denaturation, washed with 5×SSC(SSC: 15 mmol/L trisodium citrate and 150 mmol/L sodium chloride), and dried to immobilize the DNA on the membrane. After prehybridization (42° C.) for 1 hour, the HRP-labeled probe was added, and hybridization (42° C.) was carried out for 4 hours. The probe was removed by washing with 0.5×SSC supplemented with 6 M urea and 0.4% SDS twice, and with 2×SSC twice.

The nylon membrane after washing the probe was immersed in a detection solution for 1 minute, and exposed to Hyperfilm ECL (the same manufacturer) to obtain a positive clone. DNA was prepared from the positive clone in accordance with the method of Maniatis et al. (J. Sambrook, E. F. Fritsch and T. Maniatls, "Molecular Cloning", Cold Spring Harbor Laboratory Press. 1989) using LE392 as host *Escherichia coli*. LE392 was cultivated in an LB-MM medium (1% peptone, 0.5% yeast extract, 0.5% sodium chloride, 10 mmol/L magnesium sulfate, and 0.2% maltose) overnight. LE392 was infected with a phage solution derived from the single plaque, and cultivated in the LB-MM medium overnight. Sodium chloride and chloroform were added to the culture to final concentrations of 1 M and 0.8%, respectively, to promote the lysis of *Escherichia coli*. The culture was centrifuged to remove the bacterial residue, and phage particles were collected from a precipitate generated by 10% PEG 6000. The phage particles were digested with proteinase K in the presence of SDS, and subjected to phenol treatment followed by ethanol precipitation to collect phage DNA.

The obtained DNA was analyzed by Southern blotting using an ECL Direct System. As a result of hybridization using the PCR-amplified fragment of Example 3-2 as a probe, an XbaI fragment of 2.9 kbp showed hybridization patterns common to chromosomal DNA. This XbaI fragment was cloned into pUC118 to obtain plasmid pUC-ACC6, and the nucleotide sequence of the plasmid was sequenced.

(3-4) Cloning of Full-Length of ACC6 Gene

The following primers were prepared based on the nucleotide sequence obtained from pUC-ACC6, and PCR was carried out using genomic DNA as a template to amplify the ACC6 gene.

```
                                    (SEQ ID NO: 37)
pACC6-F: CTCTGCATTGAATCCCGAGA (SEQ ID NO: 38)
pACC6-R: GCAACGCTAAAGTGCTCATC
```

The amplified DNA was inserted into a pCR2.1-TOPO plasmid vector using a TOPO TA cloning kit (Invitrogen) to obtain plasmid pACC6. *Escherichia coli* TOP10 (Invitrogen) was transformed with the obtained plasmid pACC6 to obtain *Escherichia coli* TOP10/pACC6.

(3-5) Preparation of cDNA and Intron Analysis of ACC6 Gene cDNA of *Acremonium cellulolyticus* ACCP-5-1 was prepared in accordance with the method described in Example 1-4. The following primers containing the initiation codon and the stop codon were prepared based on the ACC6 gene sequence, and PCR was carried out using the cDNA as a template to amplify the ACC6 cDNA gene.

```
                                    (SEQ ID NO: 39)
ACC6-N: ATGACAATCATCTCAAAATTCGGT (SEQ ID NO: 40)
ACC6-C: TCAGGATTTCCACTTTGGAACGAA
```

The nucleotide sequence of the ACC6 cDNA gene was sequenced, and compared with the pACC6 gene to determine the location of introns.

(3-6) Deduction of Amino Acid Sequence of ACC6

The endoglucanase ACC6 gene isolated from *Acremonium cellulolyticus by the method described above consisted of* 1430 bp nucleotides corresponding to nucleotides 169-1598 of SEQ ID NO: 5. It was found that the ACC6 gene contained three introns at positions 254-309, 406-461, and 1372-1450 of SEQ ID NO: 5. The amino acid sequence of ACC6 deduced from the open reading frame (ORF) was that of SEQ ID NO: 6. It was assumed using a signal sequence prediction software SignalP 3.0 that the amino acid sequence at position −21 to −1 of ACC6 was a signal sequence.

Example 4: Cloning of ACC7 Gene (4-1) Isolation of Genomic DNA and Preparation of Genomic Library A genomic DNA library of *Acremonium cellulolyticus* ACCP-5-1 was prepared in accordance with the method described in Example 3-1.

(4-2) Cloning of ACC7 Gene Fragment

The following primers were prepared based on the sequences of known endoglucanases which were classified into Glycoside Hydrolase family 5.

```
                                    (SEQ ID NO: 41)
ACC7-F: CACGCCATGATCGACCCNCAYAAYTAYG (SEQ ID NO: 42)
ACC7-R: ACCAGGGGCCGGCNGYCCACCA
```

PCR was carried out using ACC7-F and ACC7-R as primers and genomic DNA as a template, and using LA Taq polymerase (Takara Bio). The PCR was carried out by repeating a cycle consisting of a reaction at 94° C. for 30 seconds, annealing for 30 seconds, and a reaction at 72° C. for 1 minute 40 times. The annealing temperature was lowered stepwisely from 63° C. to 53° C. in the first 20 cycles, and maintained at 53° C. in the subsequent 20 cycles. The amplified DNA fragment of 670 bp was inserted into a pCR2.1-TOPO plasmid vector using a TOPO TA cloning kit (Invitrogen) in accordance with a protocol attached to the kit to obtain plasmid TOPO-pACC7-partial.

The inserted DNA fragment cloned into plasmid TOPO-pACC7-partial was sequenced, and the obtained nucleotide sequence was translated into the amino acid sequence, and a homology search was carried out using the amino acid sequence. The sequence showed a 63% identity with that of endoglucanase (Q4WM09) derived from *Aspergillus fumigatus*, and thus, it was judged that the DNA fragment was part of an endoglucanase (Glycoside Hydrolase family 5) gene. This DNA fragment was amplified by PCR using plasmid TOPO-pACC7-partial as a template in a similar fashion, and the obtained PCR product was labeled using an ECL Direct System (Amersham Pharmacia Biotech) to obtain a probe.

(4-3) Screening by Plaque Hybridization

The genomic DNA library was screened in accordance with the method described in Example 3-3 to obtain a positive clone. The obtained positive clone was analyzed by Southern blotting, and an XbaI fragment of 3.7 kbp showed hybridization patterns common to chromosomal DNA. This XbaI fragment was cloned into pUC118 to obtain plasmid pUC-ACC7, and the nucleotide sequence of the plasmid was sequenced.

(4-4) Cloning of Full-Length of ACC7 Gene

The following primers were prepared based on the nucleotide sequence obtained from pUC-ACC7, and PCR was carried out using genomic DNA as a template to amplify the ACC7 gene.

```
                                          (SEQ ID NO: 43)
pACC7-F: CAGTCAGTTGTGTAGACACG (SEQ ID NO: 44)
pACC7-R: ACTCAGCTGGGTCTTCATAG
```

The amplified DNA was inserted into a pCR2.1-TOPO plasmid vector using a TOPO TA cloning kit (Invitrogen) to obtain plasmid pACC7. *Escherichia coli* TOP10 (Invitrogen) was transformed with the obtained plasmid pACC7 to obtain *Escherichia coli* TOP10/pACC7.

(4-5) Preparation of cDNA and Intron Analysis of ACC7 Gene cDNA of *Acremonium cellulolyticus* ACCP-5-1 was prepared in accordance with the method described in Example 1-4. The following primers containing the initiation codon and the stop codon were prepared based on the ACC7 gene sequence, and PCR was carried out using the cDNA as a template to amplify the ACC7 cDNA gene.

```
                                          (SEQ ID NO: 45)
ACC7-N: ATGAGGTCTACATCAACATTTGTA (SEQ ID NO: 46)
ACC7-C: CTAAGGGGTGTAGGCCTGCAGGAT
```

The nucleotide sequence of the ACC7 cDNA gene was sequenced, and compared with the pACC7 gene to determine the location of introns.

(4-6) Deduction of Amino Acid Sequence of ACC7

The endoglucanase ACC7 gene isolated from *Acremonium cellulolyticus by the method described above consisted of* 1307 bp nucleotides corresponding to nucleotides 70-1376 of SEQ ID NO: 7. It was found that the ACC7 gene contained two introns at positions 451-500 and 765-830 of SEQ ID NO: 7. The amino acid sequence of ACC7 deduced from the open reading frame (ORF) was that of SEQ ID NO: 8. It was assumed using a signal sequence prediction software SignalP 3.0 that the amino acid sequence at position −20 to −1 of ACC7 was a signal sequence.

Example 5: Cloning of ACC8 Gene (5-1) Isolation of Genomic DNA and Preparation of Genomic Library A genomic DNA library of *Acremonium cellulolyticus* ACCP-5-1 was prepared in accordance with the method described in Example 3-1.

(5-2) Cloning of ACC8 Gene Fragment

The following primers were prepared based on the DNA sequences corresponding to the N-terminal and c-terminal amino acid sequences of endoglucanase III derived from *Penicillium verruculosum*.

```
                                          (SEQ ID NO: 47)
MSW-N: CAACAGAGTCTATGCGCTCAATACTCGAGCTACACCAGT (SEQ ID NO: 48)
MSW-C: CTAATTGACAGCTGCAGACCAA
```

PCR was carried out using MSW-N and MSW-C as primers and genomic DNA as a template, and using LA Taq polymerase (Takara Bio). The PCR was carried out by repeating a cycle consisting of a reaction at 94° C. for 30 seconds, annealing for 30 seconds, and a reaction at 72° C. for 1 minute 40 times. The annealing temperature was lowered stepwisely from 63° C. to 53° C. in the first 20 cycles, and maintained at 53° C. in the subsequent 20 cycles. The amplified DNA fragment of 800 bp was inserted into a pCR2.1-TOPO plasmid vector using a TOPO TA cloning kit (Invitrogen) in accordance with a protocol attached to the kit to obtain plasmid TOPO-pACC8-partial.

The inserted DNA fragment cloned into plasmid TOPO-pACC8-partial was sequenced, and the obtained nucleotide sequence was translated into the amino acid sequence, and a homology search was carried out using the amino acid sequence. The sequence showed a 60% identity with that of endoglucanase Cel12A (Q8NJY4) derived from *Trichoderma viride*, and thus, it was judged that the DNA fragment was part of an endoglucanase (Glycoside Hydrolase family 12) gene. This DNA fragment was amplified by PCR using plasmid TOPO-pACC8-partial as a template in a similar fashion, and the obtained PCR product was labeled using an ECL Direct System (Amersham Pharmacia Biotech) to obtain a probe.

(5-3) Screening by Plaque Hybridization

The genomic DNA library was screened in accordance with the method described in Example 3-3 to obtain a positive clone. The obtained positive clone was analyzed by Southern blotting, and a SalI fragment of about 5 kbp showed hybridization patterns common to chromosomal DNA. This SalI fragment was cloned into pUC118 to obtain plasmid pUC-ACC8, and the nucleotide sequence of the plasmid was sequenced.

(5-4) Cloning of Full-Length of ACC8 Gene

The following primers were prepared based on the nucleotide sequence obtained from pUC-ACC8, and PCR was carried out using genomic DNA as a template to amplify the ACC8 gene.

```
                                          (SEQ ID NO: 49)
pACC8-F: AAAGACCGCGTGTTAGGATC (SEQ ID NO: 50)
pACC8-R: CGCGTAGGAAATAAGACACC
```

The amplified DNA was inserted into a pCR2.1-TOPO plasmid vector using a TOPO TA cloning kit (Invitrogen) to obtain plasmid pACC8. *Escherichia coli* TOP10 (Invitrogen) was transformed with the obtained plasmid pACC8 to obtain *Escherichia coli* TOP10/pACC8.

(5-5) Preparation of cDNA and Intron Analysis of ACC8 gene cDNA of *Acremonium cellulolyticus* ACCP-5-1 was prepared in accordance with the method described in Example 1-4. The following primers containing the initiation codon and the stop codon were prepared based on the ACC8 gene sequence, and PCR was carried out using the cDNA as a template to amplify the ACC8 cDNA gene.

```
                                                (SEQ ID NO: 51)
ACC8-N:  ATGAAGCTAACTTTTCTCCTGAAC (SEQ ID NO: 52)
ACC8-C:  CTAATTGACAGATGCAGACCAATG
```

The nucleotide sequence of the ACC8 cDNA gene was sequenced, and compared with the pACC8 gene to determine the location of introns.

(5-6) Deduction of Amino Acid Sequence of ACC8

The endoglucanase ACC8 gene isolated from *Acremonium cellulolyticus* by the method described above consisted of 834 bp nucleotides corresponding to nucleotides 141-974 of SEQ ID NO: 9. It was found that the ACC8 gene contained two introns at positions 551-609 and 831-894 of SEQ ID NO: 9. The amino acid sequence of ACC8 deduced from the open reading frame (ORF) was that of SEQ ID NO: 10. It was assumed using a signal sequence prediction software SignalP 3.0 that the amino acid sequence at position −15 to −1 of ACC8 was a signal sequence.

Example 6: Cloning of ACC9 Gene (6-1) Isolation of Genomic DNA and mRNA and Preparation of cDNA Genomic DNA of *Acremonium cellulolyticus* ACCP-5-1 was isolated in accordance with the method described in Example 1-1. cDNA of *Acremonium cellulolyticus* ACCP-5-1 was prepared in accordance with the method described in Example 1-4.

(6-2) Cloning of ACC9 Gene Fragment

The following primers were prepared based on the sequences of known endoglucanases which were classified into Glycoside Hydrolase family 45.

```
                                                (SEQ ID NO: 53)
ACC9-F:  CCGGCTGCGGCAARTGYTAYMA (SEQ ID NO: 54)
ACC9-R:  AGTACCACTGGTTCTGCACCTTRCANGTNSC
```

PCR was carried out using ACC9-F and ACC9-R as primers and genomic as a template, and using LA Taq polymerase (Takara Bio). The PCR was carried out by repeating a cycle consisting of a reaction at 94° C. for 30 seconds, annealing for 30 seconds, and a reaction at 72° C. for 1 minute 40 times. The annealing temperature was lowered stepwise from 63° C. to 53° C. in the first 20 cycles, and maintained at 53° C. in the subsequent 20 cycles. The amplified DNA fragment of 800 bp was inserted into a pCR2.1-TOPO plasmid vector using a TOPO TA cloning kit (Invitrogen) in accordance with a protocol attached to the kit to obtain plasmid TOPO-pACC9-partial.

The inserted DNA fragment cloned into plasmid TOPO-pACC9-partial was sequenced, and the obtained nucleotide sequence was translated into the amino acid sequence, and a homology search was carried out using the amino acid sequence. The sequence showed a 79% identity with that of endoglucanase EGV (Q7Z7X0) derived from *Trichoderma viride*, and thus, it was judged that the DNA fragment was part of an endoglucanase (Glycoside Hydrolase family 45) gene.

(6-3) Cloning of Full-Length of ACC9 Gene by Inverse PCR

In accordance with the method described in Example 1-3, PCR was carried out using circular DNA (obtained by digestion with SalI or XbaI) as a template and the following sequences contained in the ACC9 gene fragment as primers to obtain the 5' upstream region and the 3' downstream region of the ACC9 gene.

```
                                                (SEQ ID NO: 55)
ACC9-inv-F:  CGAAGTGTTTGGTGACAACG (SEQ ID NO: 56)
ACC9-inv-R:  GTGGTAGCTGTATCCGTAGT
```

The 5' upstream region and the 3' downstream region were sequenced to determine the complete nucleotide sequence of the ACC9 gene.

The following primers were prepared based on the nucleotide sequence obtained by the inverse PCR, and PCR was carried out using genomic DNA as a template to amplify the ACC9 gene.

```
                                                (SEQ ID NO: 57)
pACC9-F:  TACATTCCGAAGGCACAGTT (SEQ ID NO: 58)
pACC9-R:  CTGAGCTGATTATCCTGACC
```

The amplified DNA was inserted into a pCR2.1-TOPO plasmid vector using a TOPO TA cloning kit (Invitrogen) to obtain plasmid pACC9. *Escherichia coli* TOP10 (Invitrogen) was transformed with the obtained plasmid pACC9 to obtain *Escherichia coli* TOP10/pACC9.

(6-4) Intron Analysis of ACC9 Gene

The following primers containing the initiation codon and the stop codon were prepared based on the ACC9 gene sequence, and PCR was carried out using cDNA as a template to amplify the ACC9 cDNA gene.

```
                                                (SEQ ID NO: 59)
ACC9-N:  ATGAAGGCTTTCTATCTTTCTCTC (SEQ ID NO: 60)
ACC9-C:  TTAGGACGAGCTGACGCACTGGTA
```

The nucleotide sequence of the ACC9 cDNA gene was sequenced, and compared with the pACC9 gene to determine the location of introns.

(6-5) Deduction of Amino Acid Sequence of ACC9

The endoglucanase ACC9 gene isolated from *Acremonium cellulolyticus* by the method described above consisted of 1117 bp nucleotides corresponding to nucleotides 114-1230 of SEQ ID NO: 11. It was found that the ACC9 gene contained two introns at positions 183-232 and 299-357 of SEQ ID NO: 11. The amino acid sequence of ACC9 deduced from the open reading frame (ORF) was that of SEQ ID NO: 12. It was assumed using a signal sequence prediction software SignalP 3.0 that the amino acid sequence at position −16 to −1 of ACC5 was a signal sequence.

Example 7: Cloning of ACC10 Gene (7-1) Isolation of Genomic DNA and mRNA and Preparation of cDNA Genomic DNA of *Acremonium cellulolyticus* ACCP-5-1 was isolated in accordance with the method described in Example 1-1. cDNA of *Acremonium cellulolyticus* ACCP-5-1 was prepared in accordance with the method described in Example 1-4.

(7-2) Cloning of ACC10 Gene Fragment

The following primers were prepared based on the sequences of known endoglucanases which were classified into Glycoside Hydrolase family 61 and the poly A nucleotide sequence.

(SEQ ID NO: 61)
ACC10-F: GGTGTACGTGGGCACCAAYGGNMGNGG (SEQ ID NO: 62)
ACC10-R: AATTCGCGGCCGCTAAAAAAAAA

PCR was carried out using ACC10-F and ACC10-R as primers and cDNA as a template, and using LA Taq polymerase (Takara Bio). The PCR was carried out by repeating a cycle consisting of a reaction at 94° C. for 30 seconds, annealing for 30 seconds, and a reaction at 72° C. for 1 minute 40 times. The annealing temperature was lowered stepwisely from 63° C. to 53° C. in the first 20 cycles, and maintained at 53° C. in the subsequent 20 cycles. The amplified DNA fragment of 300 bp was inserted into a pCR2.1-TOPO plasmid vector using a TOPO TA cloning kit (Invitrogen) in accordance with a protocol attached to the kit to obtain plasmid TOPO-pACC10-partial.

The inserted DNA fragment cloned into plasmid TOPO-pACC10-partial was sequenced, and the obtained nucleotide sequence was translated into the amino acid sequence, and a homology search was carried out using the amino acid sequence. The sequence showed a 65% identity with that of endoglucanase EGIV (Q0DOT6) derived from *Aspergillus terreus*, and thus, it was judged that the DNA fragment was part of an endoglucanase (Glycoside Hydrolase family 61) gene.

(7-3) Cloning of Full-Length of ACC10 Gene by Inverse PCR

In accordance with the method described in Example 1-3, PCR was carried out using circular DNA (obtained by digestion with HindIII) as a template and the following sequences contained in the ACC10 gene fragment as primers to obtain the 5' upstream region and the 3' downstream region of the ACC10 gene.

(SEQ ID NO: 63)
ACC10-inv-F: TTCTGCTACTGCGGTTGCTA (SEQ ID NO: 64)
ACC10-inv-R: GAATAACGTAGGTCGACAAG The 5' upstream region and the 3' downstream region were sequenced to determine the complete nucleotide sequence of the ACC10 gene.

The following primers were prepared based on the nucleotide sequence obtained by the inverse PCR, and PCR was carried out using genomic DNA as a template to amplify the ACC10 gene.

(SEQ ID NO: 65)
pACC10-F: CGTTGACCGAAAGCCACTT (SEQ ID NO: 66)
pACC10-R: TGGCCTAAAGCTAAATGATG

The amplified DNA was inserted into a pCR2.1-TOPO plasmid vector using a TOPO TA cloning kit (Invitrogen) to obtain plasmid pACC10. *Escherichia coli* TOP10 (Invitrogen) was transformed with the obtained plasmid pACC9 to obtain *Escherichia coli* TOP10/pACC10.

(7-4) Intron Analysis of ACC10 Gene

The following primers containing the initiation codon and the stop codon were prepared based on the ACC10 gene sequence, and PCR was carried out using cDNA as a template to amplify the ACC10 cDNA gene.

(SEQ ID NO: 67)
ACC10-N: ATGCCTTCTACTAAAGTCGCTGCCC (SEQ ID NO: 68)
ACC10-C: TTAAAGGACAGTAGTGGTGATGACG

The nucleotide sequence of the ACC10 cDNA gene was sequenced, and compared with the pACC10 gene to determine the location of introns.

(7-5) Deduction of Amino Acid Sequence of ACC10

The endoglucanase ACC10 gene isolated from *Acremonium cellulolyticus* by the method described above consisted of 1020 bp nucleotides corresponding to nucleotides 124-1143 of SEQ ID NO: 13. It was found that the ACC10 gene contained an intron at position 225-275 of SEQ ID NO: 13. The amino acid sequence of ACC10 deduced from the open reading frame (ORF) was that of SEQ ID NO: 14. It was assumed using a signal sequence prediction software SignalP 3.0 that the amino acid sequence at position −21 to −1 of ACC10 was a signal sequence.

Example 8: Cloning of BGLC Gene (8-1) Preparation of Genomic DNA and cDNA

Genomic DNA of *Acremonium cellulolyticus* ACCP-5-1 was isolated in accordance with the method described in Example 1-1. cDNA of *Acremonium cellulolyticus* ACCP-5-1 was prepared in accordance with the method described in Example 1-4

(8-2) Cloning of BGLC Gene Fragment

The following primers were prepared based on the sequences of known β-glucosidases which were classified into Glycoside Hydrolase family 1.

(SEQ ID NO: 69)
BGLC-F: CCTGGGTGACCCTGTACCAYTGGGAYYT (SEQ ID NO: 70)
BGLC-R: TGGGCAGGAGCAGCCRWWYTCNGT

PCR was carried out using BGLC-F and BGLC-R as primers and genomic DNA as a template, and using LA Taq polymerase (Takara Bio). The PCR was carried out by repeating a cycle consisting of a reaction at 94° C. for 30 seconds, annealing for 30 seconds, and a reaction at 72° C. for 1 minute 40 times. The annealing temperature was lowered stepwisely from 63° C. to 53° C. in the first 20 cycles, and maintained at 53° C. in the subsequent 20 cycles. The amplified DNA fragment of 1.2 kbp was inserted into a pCR2.1-TOPO plasmid vector using a TOPO TA cloning kit (Invitrogen) in accordance with a protocol attached to the kit to obtain plasmid TOPO-pBGLC-partial.

The inserted DNA fragment cloned into plasmid TOPO-pBGLC-partial was sequenced, and the obtained nucleotide sequence was translated into the amino acid sequence, and a homology search was carried out using the amino acid sequence. The sequence showed a 69% identity with that of β-glucosidase 1 (Q4WRG4) derived from *Aspergillus fumigatus*, and thus, it was judged that the DNA fragment was part of a β-glucosidase (Glycoside Hydrolase family 1) gene.

(8-3) Cloning of Full-Length of BGLC Gene by Inverse PCR

In accordance with the method described in Example 1-3, PCR was carried out using circular DNA (obtained by digestion with XbaI) as a template and the following sequences contained in the BGLC gene fragment as primers to obtain the 5' upstream region and the 3' downstream region of the BGLC gene.

BGLC-inv-F: GGAGTTCTTCTACATTTCCC (SEQ ID NO: 71)

BGLC-inv-R: AACAAGGACGGCGTGTCAGT (SEQ ID NO: 72)

The 5' upstream region and the 3' downstream region were sequenced to determine the complete nucleotide sequence of the BGLC gene.

The following primers were prepared based on the nucleotide sequence obtained by the inverse PCR, and PCR was carried out using genomic DNA as a template to amplify the BGLC gene.

pBGLC-F: CTCCGTCAAGTGCGAAGTAT (SEQ ID NO: 73)

pBGLC-R: GGCTCGCTAATACTAACTGC (SEQ ID NO: 74)

The amplified DNA was inserted into a pCR2.1-TOPO plasmid vector using a TOPO TA cloning kit (Invitrogen) to obtain plasmid pBGLC. *Escherichia coli* TOP10 (Invitrogen) was transformed with the obtained plasmid pBGLC to obtain *Escherichia coli* TOP10/pBGLC.

(8-4) Intron Analysis of BGLC Gene

The following primers containing the initiation codon and the stop codon were prepared based on the BGLC gene sequence, and PCR was carried out using cDNA as a template to amplify the BGLC cDNA gene.

BGLC-N: ATGGGCTCTACATCTCCTGCCCAA (SEQ ID NO: 75)

BGLC-C: CTAGTTCCTCGGCTCTATGTATTT (SEQ ID NO: 76)

The nucleotide sequence of the BGLC cDNA gene was sequenced, and compared with the pBGLC gene to determine the location of introns.

(8-5) Deduction of Amino Acid Sequence of BGLC

The β-glucosidase BGLC gene isolated from *Acremonium cellulolyticus* by the method described above consisted of 1650 bp nucleotides corresponding to nucleotides 238-1887 of SEQ ID NO: 15. It was found that the BGLC gene contained three introns at positions 784-850, 1138-1205, and 1703-1756 of SEQ ID NO: 15. The amino acid sequence of BGLC deduced from the open reading frame (ORF) was that of SEQ ID NO: 16. It was assumed using a signal sequence prediction software SignalP 3.0 that the amino acid sequence at position −28 to −1 of BGLC was a signal sequence.

Example 9: Cloning of BGLD Gene (9-1) Preparation of Genomic DNA and cDNA

Genomic DNA of *Acremonium cellulolyticus* ACCP-5-1 was isolated in accordance with the method described in Example 1-1. cDNA of *Acremonium cellulolyticus* ACCP-5-1 was prepared in accordance with the method described in Example 1-4.

(9-2) Cloning of BGLD Gene Fragment

The following primers were prepared based on the sequences of known β-glucosidases which were classified into Glycoside Hydrolase family 1.

BGLD-F: CACCGCCGCCTACCARRTNGARGG (SEQ ID NO: 77)

BGLD-R: TGGCGGTGTAGTGGTTCATGSCRWARWARTC (SEQ ID NO: 78)

PCR was carried out using BGLD-F and BGLD-R as primers and genomic DNA as a template, and using LA Taq polymerase (Takara Bio). The PCR was carried out by repeating a cycle consisting of a reaction at 94° C. for 30 seconds, annealing for 30 seconds, and a reaction at 72° C. for 1 minute 40 times. The annealing temperature was lowered stepwisely from 63° C. to 53° C. in the first 20 cycles, and maintained at 53° C. in the subsequent 20 cycles. The amplified DNA fragment of 1 kbp was inserted into a pCR2.1-TOPO plasmid vector using a TOPO TA cloning kit (Invitrogen) in accordance with a protocol attached to the kit to obtain plasmid TOPO-pBGLD-partial.

The inserted DNA fragment cloned into plasmid TOPO-pBGLD-partial was sequenced, and the obtained nucleotide sequence was translated into the amino acid sequence, and a homology search was carried out using the amino acid sequence. The sequence showed a 76% identity with that of β-glucosidase 1 (Q8X214) derived from *Talaromyces emersonii*, and thus, it was judged that the DNA fragment was part of a β-glucosidase (Glycoside Hydrolase family 1) gene.

(9-3) Cloning of Full-Length of BGLD Gene by Inverse PCR

In accordance with the method described in Example 1-3, PCR was carried out using circular DNA (obtained by digestion with XhoI) as a template and the following sequences contained in the BGLD gene fragment as primers to obtain the 5' upstream region and the 3' downstream region of the BGLD gene.

BGLD-inv-F: CGGTTTCAATATCGGTAAGC (SEQ ID NO: 79)

BGLD-inv-R: GTGTCCAAAGCTCTGGAATG (SEQ ID NO: 80)

The 5' upstream region and the 3' downstream region were sequenced to determine the complete nucleotide sequence of the BGLD gene.

The following primers were prepared based on the nucleotide sequence obtained by the inverse PCR, and PCR was carried out using genomic DNA as a template to amplify the BGLD gene.

pBGLD-F: TTCTCTCACTTTCCCTTTCC (SEQ ID NO: 81)

pBGLD-R: AATTGATGCTCCTGATGCGG (SEQ ID NO: 82)

The amplified DNA was inserted into a pCR2.1-TOPO plasmid vector using a TOPO TA cloning kit (Invitrogen) to obtain plasmid pBGLD. *Escherichia coli* TOP10 (Invitrogen) was transformed with the obtained plasmid pBGLD to obtain *Escherichia coli* TOP10/pBGLD.

(9-4) Intron Analysis of BGLD Gene

The following primers containing the initiation codon and the stop codon were prepared based on the BGLD gene sequence, and PCR was carried out using cDNA as a template to amplify the BGLD cDNA gene.

```
                                                (SEQ ID NO: 83)
          BGLD-N: ATGGGTAGCGTAACTAGTACCAAC (SEQ ID NO: 84)
          BGLD-C: CTACTCTTTCGAGATGTATTTGTT
```

The nucleotide sequence of the BGLD cDNA gene was sequenced, and compared with the pBGLD gene to determine the location of introns.

(9-5) Deduction of Amino Acid Sequence of BGLD

The β-glucosidase BGLD gene isolated from *Acremonium cellulolyticus* by the method described above consisted of 1700 bp nucleotides corresponding to nucleotides 66-1765 of SEQ ID NO: 17. It was found that the BGLD gene contained four introns at positions 149-211, 404-460, 934-988, and 1575-1626 of SEQ ID NO: 17. The amino acid sequence of BGLD deduced from the open reading frame (ORF) was that of SEQ ID NO: 18. It was assumed using a signal sequence prediction software SignalP 3.0 that the amino acid sequence at position −33 to −1 of BGLD was a signal sequence.

INDUSTRIAL APPLICABILITY

The protein of the present invention may be used as a cellulase preparation, and may be applied to the use of digestion of a cellulose-based substrate.

Although the present invention has been described with reference to specific embodiments, various changes and modifications obvious to those skilled in the art are possible without departing from the scope of the appended claims.

FREE TEXT IN SEQUENCE LISTING

The nucleotide sequences of SEQ ID NOS.: 19-84 in the sequence listing are artificially synthesized primer sequences. The abbreviations "N" in SEQ ID NO: 27 (positions 18 and 27), SEQ ID NO: 41 (position 18), SEQ ID NO: 42 (position 14), SEQ ID NO: 54 (positions 26 and 29), SEQ ID NO: 61 (positions 22 and 25), SEQ ID NO: 70 (position 22), and SEQ ID NO: 77 (position 19) stand for an arbitrary nucleotide.

The invention claimed is:

1. A composition comprising a protein and an effective amount of an added preservative, wherein said protein consists of the amino acid sequence of residues 1-301 of SEQ ID NO: 14.

2. A protein having endoglucanase activity, wherein said protein consists of the amino acid sequence of residues 1-301 of SEQ ID NO: 14 with a single substitution.

* * * * *

SEQUENCE LISTING

```
<160> NUMBER OF SEQ ID NOS: 84

<210> SEQ ID NO 1
<211> LENGTH: 1644
<212> TYPE: DNA
<213> ORGANISM: Acremonium cellulolyticus
<220> FEATURE:
<221> NAME/KEY: sig_peptide
<222> LOCATION: (136)..(216)
<220> FEATURE:
<221> NAME/KEY: exon
<222> LOCATION: (136)..(232)
<220> FEATURE:
<221> NAME/KEY: CDS
<222> LOCATION: (136)..(232)
<220> FEATURE:
<221> NAME/KEY: mat_peptide
<222> LOCATION: join (217..232,292..350,426..578,632..696,755..852,
       908..1434)
<220> FEATURE:
<221> NAME/KEY: Intron
<222> LOCATION: (233)..(291)
<220> FEATURE:
<221> NAME/KEY: exon
<222> LOCATION: (292)..(350)
<220> FEATURE:
<221> NAME/KEY: CDS
<222> LOCATION: (292)..(350)
<220> FEATURE:
<221> NAME/KEY: Intron
<222> LOCATION: (351)..(425)
<220> FEATURE:
<221> NAME/KEY: exon
<222> LOCATION: (426)..(578)
<220> FEATURE:
<221> NAME/KEY: CDS
<222> LOCATION: (426)..(578)
<220> FEATURE:
<221> NAME/KEY: Intron
<222> LOCATION: (579)..(631)
<220> FEATURE:
<221> NAME/KEY: exon
<222> LOCATION: (632)..(696)
<220> FEATURE:
<221> NAME/KEY: CDS
<222> LOCATION: (632)..(696)
<220> FEATURE:
<221> NAME/KEY: Intron
<222> LOCATION: (697)..(754)
<220> FEATURE:
<221> NAME/KEY: exon
```

```
<222> LOCATION: (755)..(852)
<220> FEATURE:
<221> NAME/KEY: CDS
<222> LOCATION: (755)..(852)
<220> FEATURE:
<221> NAME/KEY: Intron
<222> LOCATION: (853)..(907)
<220> FEATURE:
<221> NAME/KEY: exon
<222> LOCATION: (908)..(1437)
<220> FEATURE:
<221> NAME/KEY: CDS
<222> LOCATION: (908)..(1437)

<400> SEQUENCE: 1
gaaggatggt agattgtccg gtggttgttc gatccaatat aaaagcatgg caggcgctgt       60
taaaaccgtg actactctca agacagaccg tacatcagat tcatcggaaa atacaagctt      120
gagaatctta tcacg atg aag acc agc atc att tct atc gtt ctg tct acg      171
              Met Lys Thr Ser Ile Ile Ser Ile Val Leu Ser Thr
                  -25                 -20 gca gga ctc act tta ggg gcc ccc tca aag gac acc aag aaa cgt gct       219
Ala Gly Leu Thr Leu Gly Ala Pro Ser Lys Asp Thr Lys Lys Arg Ala
-15                 -10                 -5                 -1  1 tca agt ttc gaa t gtatgcatat ctagtaaata gattcaagag ttcaatgact         272
Ser Ser Phe Glu
             5 gatatatgat gcctcgtag gg ttc ggt tca aat gag tcc gga gca gaa ttt       323
                       Trp Phe Gly Ser Asn Glu Ser Gly Ala Glu Phe
                                    10                  15 gga agt ggg aat atc cca ggt gtg gag gtatgcagac ttatatcgct              370
Gly Ser Gly Asn Ile Pro Gly Val Glu
             20                  25 tctatcaagc gtgacatcca gggggaaat tcaacttaac cagatgaatg gctag ggc       428
                                                              Gly acc gac tac acc ttt ccc aat aca aca gcg att caa ata ctc atc gac       476
Thr Asp Tyr Thr Phe Pro Asn Thr Thr Ala Ile Gln Ile Leu Ile Asp
             30                  35                  40 gcc ggt atg aac atc ttc cgc gtt cca ttc cta atg gag cga atg atc       524
Ala Gly Met Asn Ile Phe Arg Val Pro Phe Leu Met Glu Arg Met Ile
             45                  50                  55 ccg act gag atg act gga tct ctt aat acg gct tat ttt gag ggg tac       572
Pro Thr Glu Met Thr Gly Ser Leu Asn Thr Ala Tyr Phe Glu Gly Tyr
60                  65                  70 agc gag gtacggaccc ttatcagtcc cttcaggagt gttttggtcc tgatcggata       628
Ser Glu
75 tag gtc att aac tac atc acc ggt caa gga gca cat gca gtg gtt gac       676
    Val Ile Asn Tyr Ile Thr Gly Gln Gly Ala His Ala Val Val Asp
                 80                  85                  90 cct cac aac ttt gga cga ta  gtaagagtcc tctcctggtt attttgaaag          726
Pro His Asn Phe Gly Arg Tyr
                 95 actttagaga tacttactct cggcctag t tat gga acc cct atc tca tca aca      779
                                  Tyr Gly Thr Pro Ile Ser Ser Thr
                                                100                 105 tcc gac ttc cag act ttc tgg tcc acg ctt gcc tcc caa ttc aaa tca       827
Ser Asp Phe Gln Thr Phe Trp Ser Thr Leu Ala Ser Gln Phe Lys Ser
             110                 115                 120 aat gac aag gtc att ttt gac aca a gtaagtatat atattttttt                872
Asn Asp Lys Val Ile Phe Asp Thr
             125                 130
```

| | | |
|---|---|---|
| tacatctcaa atataaacct cgctgacaca ctcag ac aac gaa tac cac gac<br>Asn Asn Glu Tyr His Asp<br>135 | | 924 |
| atg gat gaa tcc gtc gtc gta gcc cta aac caa gca gca atc gac ggc<br>Met Asp Glu Ser Val Val Val Ala Leu Asn Gln Ala Ala Ile Asp Gly<br>140               145               150 | | 972 |
| atc cgc gat gcc ggg gcc aca aca caa tac atc ttc gtc gaa ggc aac<br>Ile Arg Asp Ala Gly Ala Thr Thr Gln Tyr Ile Phe Val Glu Gly Asn<br>155               160               165 | | 1020 |
| tct tac act ggt gcc tgg aca tgg aca aca tac aac acg gcc atg gtg<br>Ser Tyr Thr Gly Ala Trp Thr Trp Thr Thr Tyr Asn Thr Ala Met Val<br>170               175               180 | | 1068 |
| aac ctc acc gat cca tct gat cta atc gtc tac gaa atg cat caa tac<br>Asn Leu Thr Asp Pro Ser Asp Leu Ile Val Tyr Glu Met His Gln Tyr<br>185               190              195               200 | | 1116 |
| ctc gac tct gac ggg tct ggt aca tca gac caa tgc gtg agc agc aca<br>Leu Asp Ser Asp Gly Ser Gly Thr Ser Asp Gln Cys Val Ser Ser Thr<br>205               210               215 | | 1164 |
| atc ggc cag gaa cgt gtt gta gat gct aca act tgg ttg caa acc aac<br>Ile Gly Gln Glu Arg Val Val Asp Ala Thr Thr Trp Leu Gln Thr Asn<br>220               225              230 | | 1212 |
| gga aag cga ggc atc ctc ggc gaa ttc gcg ggt ggc gca aat agt gtt<br>Gly Lys Arg Gly Ile Leu Gly Glu Phe Ala Gly Gly Ala Asn Ser Val<br>235               240               245 | | 1260 |
| tgc gaa gag gcc gtg gag ggg atg ctg aat tat ctg gag cag aat tcc<br>Cys Glu Glu Ala Val Glu Gly Met Leu Asn Tyr Leu Glu Gln Asn Ser<br>250               255               260 | | 1308 |
| gac gtc tgg ctc gga gcg agc tgg tgg agt gcg ggc cca tgg tgg ggt<br>Asp Val Trp Leu Gly Ala Ser Trp Trp Ser Ala Gly Pro Trp Trp Gly<br>265               270              275               280 | | 1356 |
| gac tac att ttc tca atg gaa cca cct agt ggc act gcg tat gtg aat<br>Asp Tyr Ile Phe Ser Met Glu Pro Pro Ser Gly Thr Ala Tyr Val Asn<br>285               290              295 | | 1404 |
| tat ctg tcg att ctg gag agt tat ttc cca tga ttttgaggct attcgcaaat<br>Tyr Leu Ser Ile Leu Glu Ser Tyr Phe Pro<br>300               305 | | 1457 |
| atgttgatat agggcttgtt agagactagt acaaaagtgg tatagtacgg tggagactat | | 1517 |
| ccgtaccttg ctatatcaac tagaatttct agctagaaaa ccagaaacgg ggagggcctt | | 1577 |
| tcgttatttg ttctgtcaac tggtgcactc agtagcccaa aaaccctgc gagaaatcct | | 1637 |
| tctcggt | | 1644 |

<210> SEQ ID NO 2
<211> LENGTH: 333
<212> TYPE: PRT
<213> ORGANISM: Acremonium cellulolyticus

<400> SEQUENCE: 2

Met Lys Thr Ser Ile Ile Ser Ile Val Leu Ser Thr Ala Gly Leu Thr
           -25                   -20                     -15

Leu Gly Ala Pro Ser Lys Asp Thr Lys Lys Arg Ala Ser Ser Phe Glu
       -10                 -5                -1  1                5

Trp Phe Gly Ser Asn Glu Ser Gly Ala Glu Phe Gly Ser Gly Asn Ile
             10                  15                  20

Pro Gly Val Glu Gly Thr Asp Tyr Thr Phe Pro Asn Thr Thr Ala Ile
           25                  30                  35

Gln Ile Leu Ile Asp Ala Gly Met Asn Ile Phe Arg Val Pro Phe Leu
           40                  45                  50

| | | | | | | | | | | | |
|---|---|---|---|---|---|---|---|---|---|---|---|
| Met | Glu | Arg | Met | Ile | Pro | Thr | Glu | Met | Thr | Gly | Ser | Leu | Asn | Thr | Ala |
| | | | 55 | | | | 60 | | | | 65 | | | | |

Met Glu Arg Met Ile Pro Thr Glu Met Thr Gly Ser Leu Asn Thr Ala
                55                60                65

Tyr Phe Glu Gly Tyr Ser Glu Val Ile Asn Tyr Ile Thr Gly Gln Gly
 70               75                80                85

Ala His Ala Val Val Asp Pro His Asn Phe Gly Arg Tyr Tyr Gly Thr
                90                95               100

Pro Ile Ser Ser Thr Ser Asp Phe Gln Thr Phe Trp Ser Thr Leu Ala
               105              110              115

Ser Gln Phe Lys Ser Asn Asp Lys Val Ile Phe Asp Thr Asn Asn Glu
        120              125            130

Tyr His Asp Met Asp Glu Ser Val Val Val Ala Leu Asn Gln Ala Ala
      135             140              145

Ile Asp Gly Ile Arg Asp Ala Gly Ala Thr Thr Gln Tyr Ile Phe Val
150              155              160             165

Glu Gly Asn Ser Tyr Thr Gly Ala Trp Thr Trp Thr Thr Tyr Asn Thr
             170            175              180

Ala Met Val Asn Leu Thr Asp Pro Ser Asp Leu Ile Val Tyr Glu Met
        185              190            195

His Gln Tyr Leu Asp Ser Asp Gly Ser Gly Thr Ser Asp Gln Cys Val
      200             205              210

Ser Ser Thr Ile Gly Gln Glu Arg Val Val Asp Ala Thr Thr Trp Leu
     215              220              225

Gln Thr Asn Gly Lys Arg Gly Ile Leu Gly Glu Phe Ala Gly Gly Ala
230              235              240             245

Asn Ser Val Cys Glu Glu Ala Val Glu Gly Met Leu Asn Tyr Leu Glu
          250             255            260

Gln Asn Ser Asp Val Trp Leu Gly Ala Ser Trp Trp Ser Ala Gly Pro
      265             270              275

Trp Trp Gly Asp Tyr Ile Phe Ser Met Glu Pro Pro Ser Gly Thr Ala
          280             285            290

Tyr Val Asn Tyr Leu Ser Ile Leu Glu Ser Tyr Phe Pro
295              300              305

<210> SEQ ID NO 3
<211> LENGTH: 1839
<212> TYPE: DNA
<213> ORGANISM: Acremonium cellulolyticus
<220> FEATURE:
<221> NAME/KEY: sig_peptide
<222> LOCATION: (128)..(187)
<220> FEATURE:
<221> NAME/KEY: exon
<222> LOCATION: (128)..(1615)
<220> FEATURE:
<221> NAME/KEY: CDS
<222> LOCATION: (128)..(1615)
<220> FEATURE:
<221> NAME/KEY: mat_peptide
<222> LOCATION: (188)..(1612)

<400> SEQUENCE: 3
attgctccgc ataggttcaa gggtatataa acaggcttac tgtctaataa tctcaataac    60
tgctcaaatc cattgtttgt ccttcttcgt acctgcggcg agattcaatt ttggactgat   120 gtctaac atg gcg act aga cca ttg gct ttt gca gct att gct gct ctt   169
         Met Ala Thr Arg Pro Leu Ala Phe Ala Ala Ile Ala Ala Leu
             -20             -15             -10 ttc cac cat gcc gcc tca cag cag gcc cct acc cca gat aat tta gct   217
Phe His His Ala Ala Ser Gln Gln Ala Pro Thr Pro Asp Asn Leu Ala
   -5              -1  1         5              10

```
tct cta ccg acc tgg aaa tgt aca act tcc ggc ggc tgt gtt caa cag      265
Ser Leu Pro Thr Trp Lys Cys Thr Thr Ser Gly Gly Cys Val Gln Gln
            15              20                  25 tcg acc tct att gtc gtg gat tgg gtg tat cac tgg atc cac aca gtc      313
Ser Thr Ser Ile Val Val Asp Trp Val Tyr His Trp Ile His Thr Val
                30              35                  40 aat ggg agc aca tcg tgc acc aca tct agc gga ttg gac cca act tta      361
Asn Gly Ser Thr Ser Cys Thr Thr Ser Ser Gly Leu Asp Pro Thr Leu
            45              50                  55 tgt gga acg gaa gag gaa tgc tat aca aac tgt gaa atc tca cct gca      409
Cys Gly Thr Glu Glu Glu Cys Tyr Thr Asn Cys Glu Ile Ser Pro Ala
        60              65                  70 acc tac gat ggc ctc ggt ata aaa act tct gga aac gct tta acc ctc      457
Thr Tyr Asp Gly Leu Gly Ile Lys Thr Ser Gly Asn Ala Leu Thr Leu
75              80              85                  90 aat caa tac gtc aca agc aat gga acg aca agt aac gcc tct ccg cgt      505
Asn Gln Tyr Val Thr Ser Asn Gly Thr Thr Ser Asn Ala Ser Pro Arg
                95              100                 105 gta tat ctt ttg gat ccc gcc ggc aag aat tat gag atg ctg cag ctc      553
Val Tyr Leu Leu Asp Pro Ala Gly Lys Asn Tyr Glu Met Leu Gln Leu
            110                 115                 120 ctc ggt caa gag att agc ttt gac gta gat gcc tcc aat tta cca tgt      601
Leu Gly Gln Glu Ile Ser Phe Asp Val Asp Ala Ser Asn Leu Pro Cys
        125                 130                 135 ggc gaa aac ggg gct ctt tat ctc tct gag atg gat gcg act gga ggt      649
Gly Glu Asn Gly Ala Leu Tyr Leu Ser Glu Met Asp Ala Thr Gly Gly
    140                 145                 150 cga agc cag tac aac cct gcc gga gct tca tac ggt tcc ggt tac tgt      697
Arg Ser Gln Tyr Asn Pro Ala Gly Ala Ser Tyr Gly Ser Gly Tyr Cys
155                 160                 165                 170 gat gct cag tgt gga agt agc agc tgg ttt aat ggc tcg att aat agc      745
Asp Ala Gln Cys Gly Ser Ser Ser Trp Phe Asn Gly Ser Ile Asn Ser
                175                 180                 185 gct ggc ctc ggt tct tgc tgt aac gaa atg gat ctc tgg gaa gca aat      793
Ala Gly Leu Gly Ser Cys Cys Asn Glu Met Asp Leu Trp Glu Ala Asn
            190                 195                 200 ggc gag gca act gct ttg aca cct cat cca tgc agt gtc gat ggt cct      841
Gly Glu Ala Thr Ala Leu Thr Pro His Pro Cys Ser Val Asp Gly Pro
        205                 210                 215 tat ggc tgc tct ggt agc gcc tgt ggt tcg act gga gtg tgt gac aag      889
Tyr Gly Cys Ser Gly Ser Ala Cys Gly Ser Thr Gly Val Cys Asp Lys
    220                 225                 230 aat ggt tgc gga ttc aat cca tat gcc ctt gga aat cac agc tac tac      937
Asn Gly Cys Gly Phe Asn Pro Tyr Ala Leu Gly Asn His Ser Tyr Tyr
235                 240                 245                 250 ggc cca ggt ctt aca gtg gac aca agc aag ccc ttt aca gtt acg aca      985
Gly Pro Gly Leu Thr Val Asp Thr Ser Lys Pro Phe Thr Val Thr Thr
                255                 260                 265 cag ttt gtg acc aac gat ggc acc aag acc ggc acc ctg acc gaa att     1033
Gln Phe Val Thr Asn Asp Gly Thr Lys Thr Gly Thr Leu Thr Glu Ile
            270                 275                 280 cgt cga tct tac act cag aat ggc aag gtt att gcg aat gcc gtt gca     1081
Arg Arg Ser Tyr Thr Gln Asn Gly Lys Val Ile Ala Asn Ala Val Ala
        285                 290                 295 tcc tct tcg tcg ggg ttt tca ggt caa agt tct atc aca gag tcc ttc     1129
Ser Ser Ser Ser Gly Phe Ser Gly Gln Ser Ser Ile Thr Glu Ser Phe
    300                 305                 310 tgt act gcg atg gac tcc gaa gcc ggg aca ctg ggt ggt ctg act aca     1177
Cys Thr Ala Met Asp Ser Glu Ala Gly Thr Leu Gly Gly Leu Thr Thr
```

```
                                                                           1225
atg ggt gag gcc ctt ggc cgt ggc atg gtt ctt atc ttc agc att tgg
Met Gly Glu Ala Leu Gly Arg Gly Met Val Leu Ile Phe Ser Ile Trp
            335                 340                 345 aat gat gca ggt gga tac atg aac tgg ctg gat agt ggt agc tca ggc       1273
Asn Asp Ala Gly Gly Tyr Met Asn Trp Leu Asp Ser Gly Ser Ser Gly
            350                 355                 360 cct tgc agt agt act gca gga att ccg tcc acc att cag gcg aat gac       1321
Pro Cys Ser Ser Thr Ala Gly Ile Pro Ser Thr Ile Gln Ala Asn Asp
            365                 370                 375 ccc ggt act tcg gtt act ttc tca aac atc aag tgg ggt gat att gga       1369
Pro Gly Thr Ser Val Thr Phe Ser Asn Ile Lys Trp Gly Asp Ile Gly
            380                 385                 390 tct aca ggg tct ggc act gga gga agc agt tca tca tcg tcg tca act       1417
Ser Thr Gly Ser Gly Thr Gly Gly Ser Ser Ser Ser Ser Ser Ser Thr
395                 400                 405                 410 tcg acc tca cca aaa act acc agc acc aca aca tca gca acg acc           1465
Ser Thr Ser Pro Lys Thr Thr Ser Thr Thr Thr Ser Ala Thr Thr
                415                 420                 425 aaa aca tca gca acg aca act aca acc agc aca ggg gca act cag act       1513
Lys Thr Ser Ala Thr Thr Thr Thr Thr Ser Thr Gly Ala Thr Gln Thr
            430                 435                 440 cac tat ggt caa tgt gga ggc atg tat tat act ggt cct act gtt tgt       1561
His Tyr Gly Gln Cys Gly Gly Met Tyr Tyr Thr Gly Pro Thr Val Cys
            445                 450                 455 gcc tct ccg tac acc tgt caa gta cag aat ccg tac tat tca cag tgc       1609
Ala Ser Pro Tyr Thr Cys Gln Val Gln Asn Pro Tyr Tyr Ser Gln Cys
            460                 465                 470 ctt tag acgccgtgcc gacctatttg tatatatgcc aaattttcgt ggcttcacag        1665
Leu
475 cagaaatcat tcgatttact tcatttcttt tacatataaa tttgaaatat aaatttgact    1725 tgacaaagac gagcaaaaaa tttcctatat ttgctctaat cagctgttca atctatctga    1785 gagaaaaaga atagaagtag taacctcatt acgtctggag gcactaactc tgaa          1839

<210> SEQ ID NO 4
<211> LENGTH: 495
<212> TYPE: PRT
<213> ORGANISM: Acremonium cellulolyticus

<400> SEQUENCE: 4

Met Ala Thr Arg Pro Leu Ala Phe Ala Ala Ile Ala Ala Leu Phe His
-20                 -15                 -10                  -5

His Ala Ala Ser Gln Gln Ala Pro Thr Pro Asp Asn Leu Ala Ser Leu
            -1  1                5                  10

Pro Thr Trp Lys Cys Thr Thr Ser Gly Gly Cys Val Gln Gln Ser Thr
            15                  20                  25

Ser Ile Val Val Asp Trp Val Tyr His Trp Ile His Thr Val Asn Gly
            30                  35                  40

Ser Thr Ser Cys Thr Thr Ser Ser Gly Leu Asp Pro Thr Leu Cys Gly
45                  50                  55                  60

Thr Glu Glu Glu Cys Tyr Thr Asn Cys Glu Ile Ser Pro Ala Thr Tyr
                65                  70                  75

Asp Gly Leu Gly Ile Lys Thr Ser Gly Asn Ala Leu Thr Leu Asn Gln
            80                  85                  90

Tyr Val Thr Ser Asn Gly Thr Thr Ser Asn Ala Ser Pro Arg Val Tyr
            95                  100                 105
```

Leu Leu Asp Pro Ala Gly Lys Asn Tyr Glu Met Leu Gln Leu Gly
        110                 115                 120

Gln Glu Ile Ser Phe Asp Val Asp Ala Ser Asn Leu Pro Cys Gly Glu
125                 130                 135                 140

Asn Gly Ala Leu Tyr Leu Ser Glu Met Asp Ala Thr Gly Gly Arg Ser
                145                 150                 155

Gln Tyr Asn Pro Ala Gly Ala Ser Tyr Gly Ser Gly Tyr Cys Asp Ala
                160                 165                 170

Gln Cys Gly Ser Ser Ser Trp Phe Asn Gly Ser Ile Asn Ser Ala Gly
                175                 180                 185

Leu Gly Ser Cys Cys Asn Glu Met Asp Leu Trp Glu Ala Asn Gly Glu
        190                 195                 200

Ala Thr Ala Leu Thr Pro His Pro Cys Ser Val Asp Gly Pro Tyr Gly
205                 210                 215                 220

Cys Ser Gly Ser Ala Cys Gly Ser Thr Gly Val Cys Asp Lys Asn Gly
                225                 230                 235

Cys Gly Phe Asn Pro Tyr Ala Leu Gly Asn His Ser Tyr Tyr Gly Pro
                240                 245                 250

Gly Leu Thr Val Asp Thr Ser Lys Pro Phe Thr Val Thr Thr Gln Phe
        255                 260                 265

Val Thr Asn Asp Gly Thr Lys Thr Gly Thr Leu Thr Glu Ile Arg Arg
270                 275                 280

Ser Tyr Thr Gln Asn Gly Lys Val Ile Ala Asn Ala Val Ala Ser Ser
285                 290                 295                 300

Ser Ser Gly Phe Ser Gly Gln Ser Ile Thr Glu Ser Phe Cys Thr
                305                 310                 315

Ala Met Asp Ser Glu Ala Gly Thr Leu Gly Gly Leu Thr Thr Met Gly
                320                 325                 330

Glu Ala Leu Gly Arg Gly Met Val Leu Ile Phe Ser Ile Trp Asn Asp
        335                 340                 345

Ala Gly Gly Tyr Met Asn Trp Leu Asp Ser Gly Ser Ser Gly Pro Cys
350                 355                 360

Ser Ser Thr Ala Gly Ile Pro Ser Thr Ile Gln Ala Asn Asp Pro Gly
365                 370                 375                 380

Thr Ser Val Thr Phe Ser Asn Ile Lys Trp Gly Asp Ile Gly Ser Thr
                385                 390                 395

Gly Ser Gly Thr Gly Gly Ser Ser Ser Ser Ser Ser Thr Ser Thr
                400                 405                 410

Ser Pro Lys Thr Thr Ser Thr Thr Thr Ser Ala Thr Thr Lys Thr
        415                 420                 425

Ser Ala Thr Thr Thr Thr Thr Ser Thr Gly Ala Thr Gln Thr His Tyr
430                 435                 440

Gly Gln Cys Gly Gly Met Tyr Tyr Thr Gly Pro Thr Val Cys Ala Ser
445                 450                 455                 460

Pro Tyr Thr Cys Gln Val Gln Asn Pro Tyr Tyr Ser Gln Cys Leu
                465                 470                 475

<210> SEQ ID NO 5
<211> LENGTH: 1746
<212> TYPE: DNA
<213> ORGANISM: Acremonium cellulolyticus
<220> FEATURE:
<221> NAME/KEY: sig_peptide
<222> LOCATION: (169)..(231)
<220> FEATURE:

```
<221> NAME/KEY: exon
<222> LOCATION: (169)..(253)
<220> FEATURE:
<221> NAME/KEY: CDS
<222> LOCATION: (169)..(253)
<220> FEATURE:
<221> NAME/KEY: mat_peptide
<222> LOCATION: join (232..253,310..405,462..1371,1451..1595)
<220> FEATURE:
<221> NAME/KEY: Intron
<222> LOCATION: (254)..(309)
<220> FEATURE:
<221> NAME/KEY: exon
<222> LOCATION: (310)..(405)
<220> FEATURE:
<221> NAME/KEY: CDS
<222> LOCATION: (310)..(405)
<220> FEATURE:
<221> NAME/KEY: Intron
<222> LOCATION: (406)..(461)
<220> FEATURE:
<221> NAME/KEY: exon
<222> LOCATION: (462)..(1371)
<220> FEATURE:
<221> NAME/KEY: CDS
<222> LOCATION: (462)..(1371)
<220> FEATURE:
<221> NAME/KEY: Intron
<222> LOCATION: (1372)..(1450)
<220> FEATURE:
<221> NAME/KEY: exon
<222> LOCATION: (1451)..(1598)
<220> FEATURE:
<221> NAME/KEY: CDS
<222> LOCATION: (1451)..(1598)

<400> SEQUENCE: 5
ctctgcattg aatcccgaga gatgcacgac tcgtctgcag aaatgggaac gaaaaaccga      60
taagccaaaa ggtttggata ttaaagatat ggccatatct ccagtcgagt ttcctggaaa     120
ttggagacaa gaatcacatc ccggtttcgt cgctattact tgcgcagc atg aca atc      177
                                                    Met Thr Ile
                                                        -20 atc tca aaa ttc ggt att ggg gtg ttg atc gca gtg gcc act gcg gcc       225
Ile Ser Lys Phe Gly Ile Gly Val Leu Ile Ala Val Ala Thr Ala Ala
        -15                 -10                 -5 act gcg caa cag act gtt tgg ggg caa t gtgagcttac atatctctga           273
Thr Ala Gln Gln Thr Val Trp Gly Gln
     -1   1                   5 accaaacgaa ttggcttctc atcattattt ctatag gt  ggt ggt atc ggc tgg       326
                                            Cys Gly Gly Ile Gly Trp
                                                              10 act gga ccc agc act tgt gtt tct ggc tcc tac tgc gct cct ggg aat       374
Thr Gly Pro Ser Thr Cys Val Ser Gly Ser Tyr Cys Ala Pro Gly Asn
         15                  20                  25 ccc tac tac tct cag tgt ctt cca ggg tct g vttggtggtt tactctcaat       425
Pro Tyr Tyr Ser Gln Cys Leu Pro Gly Ser
 30                  35 aatgtccgaa tatctcaatc gctcacttga actcag ga  ccg gca aca tcc acg       478
                                            Gly Pro Ala Thr Ser Thr
                                                 40                  45 gta aca acc acg tca aga acg aca aca acc aca gcg agc att acg aca       526
Val Thr Thr Thr Ser Arg Thr Thr Thr Thr Ala Ser Ile Thr Thr
             50                  55                  60 agt gtt agc aca acg aca act ccc acg agt acc ggt aag gtg cag ttc       574
Ser Val Ser Thr Thr Thr Thr Pro Thr Ser Thr Gly Lys Val Gln Phe
             65                  70                  75 gcc gga gtg aac att gcc ggc ttc gac ttt ggc atg gtt acc agc ggc       622
```

```
                                                                       -continued Ala Gly Val Asn Ile Ala Gly Phe Asp Phe Gly Met Val Thr Ser Gly
             80              85              90 aca cag gat cta agt cag att gtc gat gag tcc gtc gat ggc gtc acg      670
Thr Gln Asp Leu Ser Gln Ile Val Asp Glu Ser Val Asp Gly Val Thr
 95             100             105 caa atg aag cat ttt gtt aac gat gat acc ttt aac ata ttc cgc ttg      718
Gln Met Lys His Phe Val Asn Asp Asp Thr Phe Asn Ile Phe Arg Leu
110             115             120             125 cct act ggg tgg cag tat ctc gtc aac aat gcc cta ggt ggc cag ctt      766
Pro Thr Gly Trp Gln Tyr Leu Val Asn Asn Ala Leu Gly Gly Gln Leu
             130             135             140 gac gcg aca aag ttc ggc cag tac gat aag ctc gtt cag ggc tgc ctt      814
Asp Ala Thr Lys Phe Gly Gln Tyr Asp Lys Leu Val Gln Gly Cys Leu
             145             150             155 tct acg ggt gcg cac tgc atc gtt gac att cat aac tat gcc cgc tgg      862
Ser Thr Gly Ala His Cys Ile Val Asp Ile His Asn Tyr Ala Arg Trp
             160             165             170 aat gga gcc atc att ggc caa ggt gga ccg acc gat gca caa ttt gtg      910
Asn Gly Ala Ile Ile Gly Gln Gly Gly Pro Thr Asp Ala Gln Phe Val
175             180             185 gat ttg tgg act cag ctt gcg acc aaa tat aag gct aat agc agg atc      958
Asp Leu Trp Thr Gln Leu Ala Thr Lys Tyr Lys Ala Asn Ser Arg Ile
190             195             200             205 gtc ttt ggc gtc atg aat gag ccc cat gat ctg aat atc acc aca tgg     1006
Val Phe Gly Val Met Asn Glu Pro His Asp Leu Asn Ile Thr Thr Trp
             210             215             220 gct gcc acc gta caa aag gtc gtt aca gca att cgt aat gct ggc gca     1054
Ala Ala Thr Val Gln Lys Val Val Thr Ala Ile Arg Asn Ala Gly Ala
             225             230             235 act tca cag atg atc ttg ctc cct ggt acc gac tac aca agt gcc gcc     1102
Thr Ser Gln Met Ile Leu Leu Pro Gly Thr Asp Tyr Thr Ser Ala Ala
             240             245             250 aat ttc gtg gaa aat gga tcc ggt gca gcc ctg gcg gca gtg gtc aat     1150
Asn Phe Val Glu Asn Gly Ser Gly Ala Ala Leu Ala Ala Val Val Asn
255             260             265 cca gat gga tct act cac aat ttg atc ttc gat gta cat aag tac ctg     1198
Pro Asp Gly Ser Thr His Asn Leu Ile Phe Asp Val His Lys Tyr Leu
270             275             280             285 gat tcg gac aat agt ggc acc cat tcc gag tgc gtc acc aac aat gtc     1246
Asp Ser Asp Asn Ser Gly Thr His Ser Glu Cys Val Thr Asn Asn Val
             290             295             300 gac gct ttc tcg agt ctc gca acc tgg ctg cga tct gta ggt cgc cag     1294
Asp Ala Phe Ser Ser Leu Ala Thr Trp Leu Arg Ser Val Gly Arg Gln
             305             310             315 gct ctg ctc tct gaa acc ggt ggc ggt aac gtt cag agc tgt gca acg     1342
Ala Leu Leu Ser Glu Thr Gly Gly Gly Asn Val Gln Ser Cys Ala Thr
             320             325             330 tac atg tgc caa cag ctt gac ttc ctg aa  gtaagtgtac atatgaatct       1391
Tyr Met Cys Gln Gln Leu Asp Phe Leu Asn
335             340 cctatatttt gcactaaaaa tccgtcaagc catatctgat atgctgatat tgcctgtag    1450 t gcg aac tcc gat gtc tac ctc gga tgg act tcc tgg tca gct ggt ggc   1499
  Ala Asn Ser Asp Val Tyr Leu Gly Trp Thr Ser Trp Ser Ala Gly Gly
            345             350             355 ttt cag gcg tcg tgg aac tat att ttg acg gaa gta cca aat ggc aat     1547
Phe Gln Ala Ser Trp Asn Tyr Ile Leu Thr Glu Val Pro Asn Gly Asn
360             365             370             375 acc gat cag tac ttg gtc cag cag tgt ttc gtt cca aag tgg aaa tcc     1595
Thr Asp Gln Tyr Leu Val Gln Gln Cys Phe Val Pro Lys Trp Lys Ser
```

```
                      380           385            390
tga atggctggtc caggtcttgt attaggtcgt acgctaaatt cttaagtttt       1648
tgggcctata tctgcttgat gcgtaagatg tgggtaatct ataaacctgc aagcctagct  1708
agcttaacgc agtaggatga tgagcacttt agcgttgc                           1746
```

<210> SEQ ID NO 6
<211> LENGTH: 412
<212> TYPE: PRT
<213> ORGANISM: Acremonium cellulolyticus

<400> SEQUENCE: 6

```
Met Thr Ile Ile Ser Lys Phe Gly Ile Gly Val Leu Ile Ala Val Ala
    -20             -15                 -10

Thr Ala Ala Thr Ala Gln Gln Thr Val Trp Gly Gln Cys Gly Gly Ile
 -5              -1   1               5                      10

Gly Trp Thr Gly Pro Ser Thr Cys Val Ser Gly Ser Tyr Cys Ala Pro
                15                  20                  25

Gly Asn Pro Tyr Tyr Ser Gln Cys Leu Pro Gly Ser Pro Ala Thr
            30                  35                  40

Ser Thr Val Thr Thr Thr Ser Arg Thr Thr Thr Thr Ala Ser Ile
 45                      50                      55

Thr Thr Ser Val Ser Thr Thr Thr Pro Thr Ser Thr Gly Lys Val
 60                  65                  70                  75

Gln Phe Ala Gly Val Asn Ile Ala Gly Phe Asp Phe Gly Met Val Thr
                80                  85                      90

Ser Gly Thr Gln Asp Leu Ser Gln Ile Val Asp Glu Ser Val Asp Gly
                95                  100                 105

Val Thr Gln Met Lys His Phe Val Asn Asp Asp Thr Phe Asn Ile Phe
            110                 115                 120

Arg Leu Pro Thr Gly Trp Gln Tyr Leu Val Asn Asn Ala Leu Gly Gly
            125                 130                 135

Gln Leu Asp Ala Thr Lys Phe Gly Gln Tyr Asp Lys Leu Val Gln Gly
140                 145                 150                 155

Cys Leu Ser Thr Gly Ala His Cys Ile Val Asp Ile His Asn Tyr Ala
                160                 165                 170

Arg Trp Asn Gly Ala Ile Ile Gly Gln Gly Gly Pro Thr Asp Ala Gln
            175                 180                 185

Phe Val Asp Leu Trp Thr Gln Leu Ala Thr Lys Tyr Lys Ala Asn Ser
            190                 195                 200

Arg Ile Val Phe Gly Val Met Asn Glu Pro His Asp Leu Asn Ile Thr
205                 210                 215

Thr Trp Ala Ala Thr Val Gln Lys Val Val Thr Ala Ile Arg Asn Ala
220                 225                 230                 235

Gly Ala Thr Ser Gln Met Ile Leu Pro Gly Thr Asp Tyr Thr Ser
                240                 245                 250

Ala Ala Asn Phe Val Glu Asn Gly Ser Gly Ala Ala Leu Ala Ala Val
            255                 260                 265

Val Asn Pro Asp Gly Ser Thr His Asn Leu Ile Phe Asp Val His Lys
            270                 275                 280

Tyr Leu Asp Ser Asp Asn Ser Gly Thr His Ser Glu Cys Val Thr Asn
            285                 290                 295

Asn Val Asp Ala Phe Ser Ser Leu Ala Thr Trp Leu Arg Ser Val Gly
300                 305                 310                 315
```

```
Arg Gln Ala Leu Leu Ser Glu Thr Gly Gly Asn Val Gln Ser Cys
            320                 325                 330

Ala Thr Tyr Met Cys Gln Gln Leu Asp Phe Leu Asn Ala Asn Ser Asp
        335                 340                 345

Val Tyr Leu Gly Trp Thr Ser Trp Ala Gly Gly Phe Gln Ala Ser
    350                 355                 360

Trp Asn Tyr Ile Leu Thr Glu Val Pro Asn Gly Asn Thr Asp Gln Tyr
365                 370                 375

Leu Val Gln Gln Cys Phe Val Pro Lys Trp Lys Ser
380                 385                 390

<210> SEQ ID NO 7
<211> LENGTH: 1551
<212> TYPE: DNA
<213> ORGANISM: Acremonium cellulolyticus
<220> FEATURE:
<221> NAME/KEY: sig_peptide
<222> LOCATION: (70)..(129)
<220> FEATURE:
<221> NAME/KEY: exon
<222> LOCATION: (70)..(450)
<220> FEATURE:
<221> NAME/KEY: CDS
<222> LOCATION: (70)..(450)
<220> FEATURE:
<221> NAME/KEY: mat_peptide
<222> LOCATION: join (130..450,501..764,831..1373)
<220> FEATURE:
<221> NAME/KEY: Intron
<222> LOCATION: (451)..(500)
<220> FEATURE:
<221> NAME/KEY: exon
<222> LOCATION: (501)..(764)
<220> FEATURE:
<221> NAME/KEY: CDS
<222> LOCATION: (501)..(764)
<220> FEATURE:
<221> NAME/KEY: Intron
<222> LOCATION: (765)..(830)
<220> FEATURE:
<221> NAME/KEY: exon
<222> LOCATION: (831)..(1376)
<220> FEATURE:
<221> NAME/KEY: CDS
<222> LOCATION: (831)..(1376)

<400> SEQUENCE: 7
cagtcagttg tgtagacacg tttactgaat attgaacagc tcccgcgtac tcaatacacc      60 ttaacaagc atg agg tct aca tca aca ttt gta gct agt gct ata cta gcg     111
           Met Arg Ser Thr Ser Thr Phe Val Ala Ser Ala Ile Leu Ala
               -20                 -15                 -10 gtc gct tcc gtt caa gcc cag cag act gga tat ggc cag tgc ggt ggt       159
Val Ala Ser Val Gln Ala Gln Gln Thr Gly Tyr Gly Gln Cys Gly Gly
 -5                  -1  1               5                  10 gag aac tgg act ggt gcc acg acc tgc gtg tct ggt tgg aca tgt acc       207
Glu Asn Trp Thr Gly Ala Thr Thr Cys Val Ser Gly Trp Thr Cys Thr
            15                  20                  25 tat ctt aac gac tgg tac tct caa tgt cta cca gct tcc agc act ctg       255
Tyr Leu Asn Asp Trp Tyr Ser Gln Cys Leu Pro Ala Ser Ser Thr Leu
        30                  35                  40 act acc acg aca tct tcg aag acc tct act act gct aca acg act tca       303
Thr Thr Thr Thr Ser Ser Lys Thr Ser Thr Thr Ala Thr Thr Thr Ser
    45                  50                  55 aag act aca acc tca tcg acg agt tca ccg acg agt acc gga aaa ttg       351
Lys Thr Thr Thr Ser Ser Thr Ser Ser Pro Thr Ser Thr Gly Lys Leu
60                  65                  70
```

```
aaa tgg ttc ggt gta gat gaa tca tgt gcc gag ttc gga act gca atg      399
Lys Trp Phe Gly Val Asp Glu Ser Cys Ala Glu Phe Gly Thr Ala Met
 75                  80                  85                  90 cca ggc act tgg ggt gtc gac ttc acc ttc gcc aat aca gca acc att      447
Pro Gly Thr Trp Gly Val Asp Phe Thr Phe Ala Asn Thr Ala Thr Ile
                 95                 100                 105 ggt gtacgtattc ttgcatagtt cgccagaaaa agcgctaatg gcatgagcag gaa       503
Gly                                                         Glu ttc atc agt cag ggt ttc aat att ttc cgt atc ccc ttt gcc atg gaa      551
Phe Ile Ser Gln Gly Phe Asn Ile Phe Arg Ile Pro Phe Ala Met Glu
        110                 115                 120 cga atg gta caa ggg tca att gac gct gct tta aat acc gca tat ttg      599
Arg Met Val Gln Gly Ser Ile Asp Ala Ala Leu Asn Thr Ala Tyr Leu
125                 130                 135                 140 acc aac tac tca gtt gcc gtc aac tat att acc tcg aat gga gca tac      647
Thr Asn Tyr Ser Val Ala Val Asn Tyr Ile Thr Ser Asn Gly Ala Tyr
                    145                 150                 155 gcc gtg att gat cct cat aat tat gga agg tac aat ggc agc atc atc      695
Ala Val Ile Asp Pro His Asn Tyr Gly Arg Tyr Asn Gly Ser Ile Ile
                160                 165                 170 acc gat act act gct ttc cag acc ttc tgg tct aac ttg gcc act gct      743
Thr Asp Thr Thr Ala Phe Gln Thr Phe Trp Ser Asn Leu Ala Thr Ala
            175                 180                 185 ttc aag agc aat tcc aaa gtt gtaagtgcat ctcctctggc cttcttcttt        794
Phe Lys Ser Asn Ser Lys Val
        190                 195 cttcaaattc tatcagtaga gattgacaat cgaaag atc ttt gac aca aac aac      848
                                       Ile Phe Asp Thr Asn Asn
                                                           200 gag tat cac gac atg gat gaa acc ctg gtt ttt aac ctg aac caa gca      896
Glu Tyr His Asp Met Asp Glu Thr Leu Val Phe Asn Leu Asn Gln Ala
                205                 210                 215 gca att gac ggt att cgt ggc gcc gga gcc aca acg caa tat atc ttt      944
Ala Ile Asp Gly Ile Arg Gly Ala Gly Ala Thr Thr Gln Tyr Ile Phe
        220                 225                 230 gcc gaa ggt aat agc tgg act gga gca tgg acc tgg aac acg acc aat      992
Ala Glu Gly Asn Ser Trp Thr Gly Ala Trp Thr Trp Asn Thr Thr Asn
235                 240                 245 gat tca ctc aaa gat cta agt gat cct gag aac cta ctt gtc tac gaa     1040
Asp Ser Leu Lys Asp Leu Ser Asp Pro Glu Asn Leu Leu Val Tyr Glu
250                 255                 260                 265 atg cac caa tac ctt gac tct gat gga tct ggc aca aat tct gcc tgc     1088
Met His Gln Tyr Leu Asp Ser Asp Gly Ser Gly Thr Asn Ser Ala Cys
                270                 275                 280 gtc tcc tca aca att ggt gtc gag cgt gta gaa ggt gcc act gct tgg     1136
Val Ser Ser Thr Ile Gly Val Glu Arg Val Glu Gly Ala Thr Ala Trp
            285                 290                 295 tta cag gcg aac aaa aag ctc ggt gtt cta gga gag tat gcc ggt ggc     1184
Leu Gln Ala Asn Lys Lys Leu Gly Val Leu Gly Glu Tyr Ala Gly Gly
        300                 305                 310 ccc aac tcg gtc tgt caa gcc gcc gta aca gga atg ctg gac cat cta     1232
Pro Asn Ser Val Cys Gln Ala Ala Val Thr Gly Met Leu Asp His Leu
315                 320                 325 gtc gcc aac aac gac gtc tgg cta gga gcc gtg tgg tgg gcg gct ggt     1280
Val Ala Asn Asn Asp Val Trp Leu Gly Ala Val Trp Trp Ala Ala Gly
330                 335                 340                 345 cca tgg tgg cct tct tcg act tgg gca agc att gag cca ccg agt gga     1328
Pro Trp Trp Pro Ser Ser Thr Trp Ala Ser Ile Glu Pro Pro Ser Gly
                350                 355                 360
```

```
cag gct tat gtc tat tat gat gaa atc ctg cag gcc tac acc cct tag      1376
Gln Ala Tyr Val Tyr Tyr Asp Glu Ile Leu Gln Ala Tyr Thr Pro
    365                 370                 375 ataggcttag ggttagggtt aacatcctct taaatcgtag caatcaagac gcttactacc    1436
atgacggatg caccacttat aagggccttt ttaagatgac cttagatcac agttgggtcc    1496
cataatatgt aacttctaca tgaattgttt gataccttatg aagacccagc tgagt        1551
```

<210> SEQ ID NO 8
<211> LENGTH: 396
<212> TYPE: PRT
<213> ORGANISM: Acremonium cellulolyticus

<400> SEQUENCE: 8

```
Met Arg Ser Thr Ser Thr Phe Val Ala Ser Ala Ile Leu Ala Val Ala
-20             -15                 -10                  -5

Ser Val Gln Ala Gln Thr Gly Tyr Gly Gln Cys Gly Gly Glu Asn
         -1  1              5                  10

Trp Thr Gly Ala Thr Thr Cys Val Ser Gly Trp Thr Cys Thr Tyr Leu
         15                  20                  25

Asn Asp Trp Tyr Ser Gln Cys Leu Pro Ala Ser Ser Thr Leu Thr Thr
        30                  35                  40

Thr Thr Ser Ser Lys Thr Ser Thr Thr Ala Thr Thr Ser Lys Thr
45                  50                  55                  60

Thr Thr Ser Ser Thr Ser Ser Pro Thr Ser Thr Gly Lys Leu Lys Trp
                65                  70                  75

Phe Gly Val Asp Glu Ser Cys Ala Glu Phe Gly Thr Ala Met Pro Gly
            80                  85                  90

Thr Trp Gly Val Asp Phe Thr Phe Ala Asn Thr Ala Thr Ile Gly Glu
            95                 100                 105

Phe Ile Ser Gln Gly Phe Asn Ile Phe Arg Ile Pro Phe Ala Met Glu
        110                 115                 120

Arg Met Val Gln Gly Ser Ile Asp Ala Ala Leu Asn Thr Ala Tyr Leu
125                 130                 135                 140

Thr Asn Tyr Ser Val Ala Val Asn Tyr Ile Thr Ser Asn Gly Ala Tyr
                145                 150                 155

Ala Val Ile Asp Pro His Asn Tyr Gly Arg Tyr Asn Gly Ser Ile Ile
            160                 165                 170

Thr Asp Thr Thr Ala Phe Gln Thr Phe Trp Ser Asn Leu Ala Thr Ala
        175                 180                 185

Phe Lys Ser Asn Ser Lys Val Ile Phe Asp Thr Asn Asn Glu Tyr His
    190                 195                 200

Asp Met Asp Glu Thr Leu Val Phe Asn Leu Asn Gln Ala Ala Ile Asp
205                 210                 215                 220

Gly Ile Arg Gly Ala Gly Ala Thr Thr Gln Tyr Ile Phe Ala Glu Gly
                225                 230                 235

Asn Ser Trp Thr Gly Ala Trp Thr Trp Asn Thr Asn Asp Ser Leu
            240                 245                 250

Lys Asp Leu Ser Asp Pro Glu Asn Leu Leu Val Tyr Glu Met His Gln
        255                 260                 265

Tyr Leu Asp Ser Asp Gly Ser Gly Thr Asn Ser Ala Cys Val Ser Ser
    270                 275                 280

Thr Ile Gly Val Glu Arg Val Glu Gly Ala Thr Ala Trp Leu Gln Ala
285                 290                 295                 300

Asn Lys Lys Leu Gly Val Leu Gly Glu Tyr Ala Gly Gly Pro Asn Ser
```

305                 310                 315
Val Cys Gln Ala Ala Val Thr Gly Met Leu Asp His Leu Val Ala Asn
            320                 325                 330

Asn Asp Val Trp Leu Gly Ala Val Trp Trp Ala Gly Pro Trp Trp
                335                 340                 345

Pro Ser Ser Thr Trp Ala Ser Ile Glu Pro Pro Ser Gly Gln Ala Tyr
    350                 355                 360

Val Tyr Tyr Asp Glu Ile Leu Gln Ala Tyr Thr Pro
365                 370                 375

<210> SEQ ID NO 9
<211> LENGTH: 1090
<212> TYPE: DNA
<213> ORGANISM: Acremonium cellulolyticus
<220> FEATURE:
<221> NAME/KEY: sig_peptide
<222> LOCATION: (141)..(185)
<220> FEATURE:
<221> NAME/KEY: exon
<222> LOCATION: (141)..(550)
<220> FEATURE:
<221> NAME/KEY: CDS
<222> LOCATION: (141)..(550)
<220> FEATURE:
<221> NAME/KEY: mat_peptide
<222> LOCATION: join (186..550,610..830,895..971)
<220> FEATURE:
<221> NAME/KEY: Intron
<222> LOCATION: (551)..(609)
<220> FEATURE:
<221> NAME/KEY: exon
<222> LOCATION: (610)..(830)
<220> FEATURE:
<221> NAME/KEY: CDS
<222> LOCATION: (610)..(830)
<220> FEATURE:
<221> NAME/KEY: Intron
<222> LOCATION: (831)..(894)
<220> FEATURE:
<221> NAME/KEY: exon
<222> LOCATION: (895)..(974)
<220> FEATURE:
<221> NAME/KEY: CDS
<222> LOCATION: (895)..(974)

<400> SEQUENCE: 9
aaagaccgcg tgttaggatc ggttgacttg tctataaaag cctcgactcc tacgcttcca      60
gagttgtctg ctaggcttct atcatcggac tatcacaact tttaaaccta cacttctaag     120
aaaaagaatc tcatttcaag atg aag cta act ttt ctc ctg aac ctg gcc gtt    173
                      Met Lys Leu Thr Phe Leu Leu Asn Leu Ala Val
                      -15                 -10                 -5 gcc gca tct gct cag cag agc cta tgc tct caa tac tcg agc tac acc      221
Ala Ala Ser Ala Gln Gln Ser Leu Cys Ser Gln Tyr Ser Ser Tyr Thr
         -1  1                 5                  10 agt ggc cag tac tcc gtc aac aac aac cta tgg ggt gag agc agt ggc      269
Ser Gly Gln Tyr Ser Val Asn Asn Asn Leu Trp Gly Glu Ser Ser Gly
         15                  20                  25 tct ggc tcc cag tgc act tat gtc aat tcc att tcc agc tct ggc gtt      317
Ser Gly Ser Gln Cys Thr Tyr Val Asn Ser Ile Ser Ser Ser Gly Val
     30                  35                  40 tca tgg tct act acc tgg aac tgg tcc gga ggc agc acc tcg gtc aag      365
Ser Trp Ser Thr Thr Trp Asn Trp Ser Gly Gly Ser Thr Ser Val Lys
45                  50                  55                  60 agc tat gcc aat tcg cag ttg act ggc ctc acc aag aag ctc gtc agc      413
Ser Tyr Ala Asn Ser Gln Leu Ser Gly Leu Thr Lys Lys Leu Val Ser
                 65                  70                  75

```
aac ttg caa agc att cct acc tct gtg cag tgg agc tat agc aat acc      461
Asn Leu Gln Ser Ile Pro Thr Ser Val Gln Trp Ser Tyr Ser Asn Thr
         80                  85                  90 aac atc gtt gcc gat gtt tcg tat gat ctc ttc acg gca gcg gat atc      509
Asn Ile Val Ala Asp Val Ser Tyr Asp Leu Phe Thr Ala Ala Asp Ile
     95                 100                 105 aac cat gtt acc tac agt ggt gac tat gag ctc atg atc tg               550
Asn His Val Thr Tyr Ser Gly Asp Tyr Glu Leu Met Ile Trp
        110                 115                 120 gtaaatatgc ccccgtcgta tttcaagtat gagacatctc ccgctaatca agatatcag     609 g ctc ggt aag tac ggc ggt gcc cag ccc ctc ggc agt caa atc gga aca    658
  Leu Gly Lys Tyr Gly Gly Ala Gln Pro Leu Gly Ser Gln Ile Gly Thr
              125                 130                 135 gcc aac gtg gga ggc gca acc tgg cag ctg tgg tat ggc gta aac gga      706
Ala Asn Val Gly Gly Ala Thr Trp Gln Leu Trp Tyr Gly Val Asn Gly
        140                 145                 150 tcc caa aaa acg tac agt ttc gtc gcc tcc agc caa aca act tca tgg      754
Ser Gln Lys Thr Tyr Ser Phe Val Ala Ser Ser Gln Thr Thr Ser Trp
155                 160                 165                 170 aac ggc gat atc ttg cag ttc ttc aag tat cta cag agc aac cag ggc      802
Asn Gly Asp Ile Leu Gln Phe Phe Lys Tyr Leu Gln Ser Asn Gln Gly
                175                 180                 185 ttt cca gct agc agc cag tac ttg atc g gtaagccatg acccttctg           850
Phe Pro Ala Ser Ser Gln Tyr Leu Ile
                190                 195 ttcctataga ctccttgtat ctgacatgat tgcttcggta tcag at  ctg caa ttc     905
                                                    Asp Leu Gln Phe ggc acg gaa ccg ttt aca gga agc cag act act ttg acg gtc aac cat      953
Gly Thr Glu Pro Phe Thr Gly Ser Gln Thr Thr Leu Thr Val Asn His
200                 205                 210                 215 tgg tct gca tct gtc aat tag actactatag tctttcgaat tgcagacact         1004
Trp Ser Ala Ser Val Asn
                220 ggtttctacg tgtatctgtc atccagttgc atgtgaggat ggatgaactt cttccgtgga   1064 cgtattggtg tcttatttcc tacgcg                                         1090

<210> SEQ ID NO 10
<211> LENGTH: 236
<212> TYPE: PRT
<213> ORGANISM: Acremonium cellulolyticus

<400> SEQUENCE: 10

Met Lys Leu Thr Phe Leu Leu Asn Leu Ala Val Ala Ala Ser Ala Gln
-15                 -10                 -5                  -1  1

Gln Ser Leu Cys Ser Gln Tyr Ser Tyr Thr Ser Gly Gln Tyr Ser
         5                  10                  15

Val Asn Asn Asn Leu Trp Gly Glu Ser Ser Gly Ser Gly Ser Gln Cys
        20                  25                  30

Thr Tyr Val Asn Ser Ile Ser Ser Ser Gly Val Ser Trp Ser Thr Thr
            35                  40                  45

Trp Asn Trp Ser Gly Gly Ser Thr Ser Val Lys Ser Tyr Ala Asn Ser
50                  55                  60                  65

Gln Leu Ser Gly Leu Thr Lys Lys Leu Val Ser Asn Leu Gln Ser Ile
                70                  75                  80

Pro Thr Ser Val Gln Trp Ser Tyr Ser Asn Thr Asn Ile Val Ala Asp
            85                  90                  95
```

-continued

```
Val Ser Tyr Asp Leu Phe Thr Ala Ala Asp Ile Asn His Val Thr Tyr
            100                 105                 110
Ser Gly Asp Tyr Glu Leu Met Ile Trp Leu Gly Lys Tyr Gly Gly Ala
        115                 120                 125
Gln Pro Leu Gly Ser Gln Ile Gly Thr Ala Asn Val Gly Gly Ala Thr
130                 135                 140                 145
Trp Gln Leu Trp Tyr Gly Val Asn Gly Ser Gln Lys Thr Tyr Ser Phe
                150                 155                 160
Val Ala Ser Ser Gln Thr Thr Ser Trp Asn Gly Asp Ile Leu Gln Phe
            165                 170                 175
Phe Lys Tyr Leu Gln Ser Asn Gln Gly Phe Pro Ala Ser Ser Gln Tyr
        180                 185                 190
Leu Ile Asp Leu Gln Phe Gly Thr Glu Pro Phe Thr Gly Ser Gln Thr
    195                 200                 205
Thr Leu Thr Val Asn His Trp Ser Ala Ser Val Asn
210                 215                 220

<210> SEQ ID NO 11
<211> LENGTH: 1379
<212> TYPE: DNA
<213> ORGANISM: Acremonium cellulolyticus
<220> FEATURE:
<221> NAME/KEY: sig_peptide
<222> LOCATION: (114)..(161)
<220> FEATURE:
<221> NAME/KEY: exon
<222> LOCATION: (114)..(182)
<220> FEATURE:
<221> NAME/KEY: CDS
<222> LOCATION: (114)..(182)
<220> FEATURE:
<221> NAME/KEY: mat_peptide
<222> LOCATION: join (162..182,233..298,358..1227)
<220> FEATURE:
<221> NAME/KEY: Intron
<222> LOCATION: (183)..(232)
<220> FEATURE:
<221> NAME/KEY: exon
<222> LOCATION: (233)..(298)
<220> FEATURE:
<221> NAME/KEY: CDS
<222> LOCATION: (233)..(298)
<220> FEATURE:
<221> NAME/KEY: Intron
<222> LOCATION: (299)..(357)
<220> FEATURE:
<221> NAME/KEY: exon
<222> LOCATION: (358)..(1230)
<220> FEATURE:
<221> NAME/KEY: CDS
<222> LOCATION: (358)..(1230)

<400> SEQUENCE: 11
tacattccga aggcacagtt ccttcttcca ttcattcctt tgcgtttact accgttctct      60
tctctagact atctttgaat tcttgttcga gatctttacc accggttgga aaa atg       116
                                                            Met aag gct ttc tat ctt tct ctc tgg gcg ctg gcg ggt tcg gcg tct gcc      164
Lys Ala Phe Tyr Leu Ser Leu Trp Ala Leu Ala Gly Ser Ala Ser Ala
-15                 -10                 -5                  -1  1 tac ctt gca act act act gtaagaaact ggactattac atgggcgaat              212
Tyr Leu Ala Thr Thr Thr
                5 ttatgctaat tgtcttatag cgt tac tat gac ggc cag gaa ggt gct tgc ggt    265
                      Arg Tyr Tyr Asp Gly Gln Glu Gly Ala Cys Gly
                           10                  15
```

| | |
|---|---|
| tgt ggt agc agc tcc gga ctc gac tca tgg cag gttagtattc ccaaccgtct<br>Cys Gly Ser Ser Ser Gly Leu Asp Ser Trp Gln<br>20                       25 | 318 |
| tccatgacag gattacctag gtatgttaac atgaaacag ctc gac gtg tca acc<br>                                                     Leu Asp Val Ser Thr<br>                                                      30 | 372 |
| ggt gtc tat acc gcc gcc ggt tct caa gcc ctc ttc gac acc gac ggc<br>Gly Val Tyr Thr Ala Ala Gly Ser Gln Ala Leu Phe Asp Thr Asp Gly<br>35                       40                    45                    50 | 420 |
| tcc tcc tgg tgc ggc ggc ggt tgc ggt aaa tgc tac aac cta acc tcc<br>Ser Ser Trp Cys Gly Gly Gly Cys Gly Lys Cys Tyr Asn Leu Thr Ser<br>                    55                    60                    65 | 468 |
| acc ggc acc tcc gcc tgc aac ggc tgc ggt gaa gga ggt gtc gcc ggc<br>Thr Gly Thr Ser Ala Cys Asn Gly Cys Gly Glu Gly Gly Val Ala Gly<br>                70                    75                    80 | 516 |
| gaa agc atc atc gtc atg gtc acc aac ctc tgc ccc tac aac gga aac<br>Glu Ser Ile Ile Val Met Val Thr Asn Leu Cys Pro Tyr Asn Gly Asn<br>      85                    90                    95 | 564 |
| gaa gtc tgg tgc ccc tcg gtc ggt gcc aaa aac aac tac gga tac agc<br>Glu Val Trp Cys Pro Ser Val Gly Ala Lys Asn Asn Tyr Gly Tyr Ser<br>100                    105                  110 | 612 |
| tac cac ttc gat atc atg gct caa agc gaa gtg ttt ggt gac aac gtt<br>Tyr His Phe Asp Ile Met Ala Gln Ser Glu Val Phe Gly Asp Asn Val<br>115                    120                  125                  130 | 660 |
| gtc gtc aac ttt gag ccc gtc gct tgc ccc ggt cag gct gcc tcg gat<br>Val Val Asn Phe Glu Pro Val Ala Cys Pro Gly Gln Ala Ala Ser Asp<br>                    135                  140                  145 | 708 |
| tgg gag act tgt act tgc tat ggt cag acg gat act gat act acc cct<br>Trp Glu Thr Cys Thr Cys Tyr Gly Gln Thr Asp Thr Asp Thr Thr Pro<br>150                    155                  160 | 756 |
| gct ggg atg acg act gct gct gga tct gcg ggt act gtt gcg act tca<br>Ala Gly Met Thr Thr Ala Ala Gly Ser Ala Gly Thr Val Ala Thr Ser<br>                 165                  170                  175 | 804 |
| tct gct tct tcg tcg tcg act tca act tcg acc act ttg ctc gct gtt<br>Ser Ala Ser Ser Ser Ser Thr Ser Thr Ser Thr Thr Leu Leu Ala Val<br>180                    185                  190 | 852 |
| tcg act tct ccc gtg aaa gag gtt gct tcc tcg act tcc acc tca tct<br>Ser Thr Ser Pro Val Lys Glu Val Ala Ser Ser Thr Ser Thr Ser Ser<br>195                    200                  205                  210 | 900 |
| acc tct acc tcg acc gtc aag cca gtc tcg act gtc gtt gcc gaa acc<br>Thr Ser Thr Ser Thr Val Lys Pro Val Ser Thr Val Val Ala Glu Thr<br>                    215                  220                  225 | 948 |
| tcc cct gcc gct gtc gtt gag ccc acc aca aca gca gtc tca aac ccc<br>Ser Pro Ala Ala Val Val Glu Pro Thr Thr Thr Ala Val Ser Asn Pro<br>              230                    235                  240 | 996 |
| caa ggc gcc gct aca aca acc acc acc tac gtg aca gat tac act acc<br>Gln Gly Ala Ala Thr Thr Thr Thr Thr Tyr Val Thr Asp Tyr Thr Thr<br>              245                    250                  255 | 1044 |
| gtc acc gaa acc tcc acc atc tgg gcc act caa acc ccc agc tcc aca<br>Val Thr Glu Thr Ser Thr Ile Trp Ala Thr Gln Thr Pro Ser Ser Thr<br>260                    265                  270 | 1092 |
| acc ggt agc tcc agt gcc gtc cag act ctg tac gga cag tgc ggc ggt<br>Thr Gly Ser Ser Ser Ala Val Gln Thr Leu Tyr Gly Gln Cys Gly Gly<br>275                    280                  285                  290 | 1140 |
| atc aac tgg acc ggc gcc acg aca tgc act tct ggc gca act tgc aag<br>Ile Asn Trp Thr Gly Ala Thr Thr Cys Thr Ser Gly Ala Thr Cys Lys<br>                    295                  300                  305 | 1188 |
| gtg cag aac cct tac tac tac cag tgc gtc agc tcg tcc taa<br>Val Gln Asn Pro Tyr Tyr Tyr Gln Cys Val Ser Ser Ser<br>310                    315 | 1230 |

```
atcagcgagt tgatccggga agataactag tccacttgga caaattctct gaagatattc    1290
atctttcttt tcaaaatctt tctacttctc tttgagacta ttacttttcg cttcgtgtct    1350
tctgtgcatg gtcaggataa tcagctcag                                      1379
```

<210> SEQ ID NO 12
<211> LENGTH: 335
<212> TYPE: PRT
<213> ORGANISM: Acremonium cellulolyticus

<400> SEQUENCE: 12

```
Met Lys Ala Phe Tyr Leu Ser Leu Trp Ala Leu Ala Gly Ser Ala Ser
    -15             -10                 -5                  -1

Ala Tyr Leu Ala Thr Thr Thr Arg Tyr Tyr Asp Gly Gln Glu Gly Ala
1               5                  10                  15

Cys Gly Cys Gly Ser Ser Ser Gly Leu Asp Ser Trp Gln Leu Asp Val
                20                  25                  30

Ser Thr Gly Val Tyr Thr Ala Ala Gly Ser Gln Ala Leu Phe Asp Thr
            35                  40                  45

Asp Gly Ser Ser Trp Cys Gly Gly Cys Gly Lys Cys Tyr Asn Leu
50                  55                  60

Thr Ser Thr Gly Thr Ser Ala Cys Asn Gly Cys Gly Glu Gly Gly Val
65                  70                  75                  80

Ala Gly Glu Ser Ile Ile Val Met Val Thr Asn Leu Cys Pro Tyr Asn
                85                  90                  95

Gly Asn Glu Val Trp Cys Pro Ser Val Gly Ala Lys Asn Asn Tyr Gly
                100                 105                 110

Tyr Ser Tyr His Phe Asp Ile Met Ala Gln Ser Glu Val Phe Gly Asp
            115                 120                 125

Asn Val Val Asn Phe Glu Pro Val Ala Cys Pro Gly Gln Ala Ala
130                 135                 140

Ser Asp Trp Glu Thr Cys Thr Cys Tyr Gly Gln Thr Asp Thr Asp Thr
145                 150                 155                 160

Thr Pro Ala Gly Met Thr Thr Ala Ala Gly Ser Ala Gly Thr Val Ala
                165                 170                 175

Thr Ser Ser Ala Ser Ser Ser Thr Ser Thr Ser Thr Thr Leu Leu
                180                 185                 190

Ala Val Ser Thr Ser Pro Val Lys Glu Val Ala Ser Ser Thr Ser Thr
            195                 200                 205

Ser Ser Thr Ser Thr Ser Thr Val Lys Pro Val Ser Thr Val Val Ala
    210                 215                 220

Glu Thr Ser Pro Ala Ala Val Val Glu Pro Thr Thr Ala Val Ser
225                 230                 235                 240

Asn Pro Gln Gly Ala Ala Thr Thr Thr Thr Tyr Val Thr Asp Tyr
                245                 250                 255

Thr Thr Val Thr Glu Thr Ser Thr Ile Trp Ala Thr Gln Thr Pro Ser
            260                 265                 270

Ser Thr Thr Gly Ser Ser Ser Ala Val Gln Thr Leu Tyr Gly Gln Cys
    275                 280                 285

Gly Gly Ile Asn Trp Thr Gly Ala Thr Thr Cys Thr Ser Gly Ala Thr
                290                 295                 300

Cys Lys Val Gln Asn Pro Tyr Tyr Tyr Gln Cys Val Ser Ser Ser
305                 310                 315
```

<210> SEQ ID NO 13
<211> LENGTH: 1348
<212> TYPE: DNA
<213> ORGANISM: Acremonium cellulolyticus
<220> FEATURE:
<221> NAME/KEY: sig_peptide
<222> LOCATION: (124)..(186)
<220> FEATURE:
<221> NAME/KEY: exon
<222> LOCATION: (124)..(224)
<220> FEATURE:
<221> NAME/KEY: CDS
<222> LOCATION: (124)..(224)
<220> FEATURE:
<221> NAME/KEY: mat_peptide
<222> LOCATION: join (187..224,276..1140)
<220> FEATURE:
<221> NAME/KEY: Intron
<222> LOCATION: (225)..(275)
<220> FEATURE:
<221> NAME/KEY: exon
<222> LOCATION: (276)..(1143)
<220> FEATURE:
<221> NAME/KEY: CDS
<222> LOCATION: (276)..(1143)

<400> SEQUENCE: 13

```
cgttgaccga aagccacttg actcttctct tctgtttctc aacatccacc aagctaccca      60
gctccttgcc tccttacctt ctttacctac aatttctacc tttaacaaga actcgttgac     120 gag atg cct tct act aaa gtc gct gcc ctt tct gct gtt cta gct ttg       168
    Met Pro Ser Thr Lys Val Ala Ala Leu Ser Ala Val Leu Ala Leu
        -20             -15                 -10 gcc tcc acg gtt gct ggc cat ggt ttt gtg caa aac atc gtt atc gac       216
Ala Ser Thr Val Ala Gly His Gly Phe Val Gln Asn Ile Val Ile Asp
 -5              -1  1               5                  10 ggt aaa tc   gtaagcagtg atgcatccat tattaaacta gacatgctta              264
Gly Lys Ser caaaaaatca g t tac tct gga tac ctt gtg aat cag ttc ccc tac gag        312
              Tyr Ser Gly Tyr Leu Val Asn Gln Phe Pro Tyr Glu
                  15                  20                  25 tcc aac cca cca gct gtt att ggg tgg gca aca act gca acc gac ctg       360
Ser Asn Pro Pro Ala Val Ile Gly Trp Ala Thr Thr Ala Thr Asp Leu
                30                  35                  40 gga ttc gtc gct ccc agt gag tac acc aat gca gac att atc tgc cac       408
Gly Phe Val Ala Pro Ser Glu Tyr Thr Asn Ala Asp Ile Ile Cys His
         45                  50                  55 aag aac gcc aca cct ggc gcg ctt tct gct cca gtt gct gca ggg ggc       456
Lys Asn Ala Thr Pro Gly Ala Leu Ser Ala Pro Val Ala Ala Gly Gly
     60                  65                  70 act gtc gag ctc cag tgg act aca tgg ccc gat agt cat cac ggt cct       504
Thr Val Glu Leu Gln Trp Thr Thr Trp Pro Asp Ser His His Gly Pro
 75                  80                  85 gtc atc agc tac ctc gcc aac tgc aat ggc aat tgt tct acc gtg gat       552
Val Ile Ser Tyr Leu Ala Asn Cys Asn Gly Asn Cys Ser Thr Val Asp
 90                  95                 100                 105 aag act aag cta aac ttt gtc aag att gac caa ggt ggt ttg atc gac       600
Lys Thr Lys Leu Asn Phe Val Lys Ile Asp Gln Gly Gly Leu Ile Asp
             110                 115                 120 gat act acc ccc ccg ggt aca tgg gct tcc gac aaa ctt atc gct gcc       648
Asp Thr Thr Pro Pro Gly Thr Trp Ala Ser Asp Lys Leu Ile Ala Ala
             125                 130                 135 aac aac agc tgg act gta act atc ccc tcc acc atc gcg cct gga aac       696
Asn Asn Ser Trp Thr Val Thr Ile Pro Ser Thr Ile Ala Pro Gly Asn
         140                 145                 150
```

-continued

| | |
|---|---|
| tac gtt ttg cgc cac gaa atc att gct ctt cat tcc gct gga aac gca<br>Tyr Val Leu Arg His Glu Ile Ile Ala Leu His Ser Ala Gly Asn Ala<br>155                        160                        165 | 744 |
| gac ggt gcc caa aac tac cct caa tgc atc aac ttg gag atc acc ggc<br>Asp Gly Ala Gln Asn Tyr Pro Gln Cys Ile Asn Leu Glu Ile Thr Gly<br>170                        175                    180                    185 | 792 |
| agc gga acc gcc gct ccc tct ggt acc gct ggc gaa aag ctc tac acc<br>Ser Gly Thr Ala Ala Pro Ser Gly Thr Ala Gly Glu Lys Leu Tyr Thr<br>                    190                    195                    200 | 840 |
| tct act gac ccc ggt atc ttg gtc aat atc tac caa tcc ttg tcg acc<br>Ser Thr Asp Pro Gly Ile Leu Val Asn Ile Tyr Gln Ser Leu Ser Thr<br>              205                    210                    215 | 888 |
| tac gtt att ccc gga cca act ctg tgg agc ggt gct gcc aat ggc gct<br>Tyr Val Ile Pro Gly Pro Thr Leu Trp Ser Gly Ala Ala Asn Gly Ala<br>220                        225                    230 | 936 |
| gtt gcc act ggt tct gct act gcg gtt gct acg act gcc gct gct tct<br>Val Ala Thr Gly Ser Ala Thr Ala Val Ala Thr Thr Ala Ala Ala Ser<br>235                        240                    245 | 984 |
| gcg acc gct act cct acc aca ctt gtt acc tct gtc gct cca gct tca<br>Ala Thr Ala Thr Pro Thr Thr Leu Val Thr Ser Val Ala Pro Ala Ser<br>250                        255                    260                    265 | 1032 |
| tct acc tct gcc act gct gtt gtg acc act gtc gct cct gca gta act<br>Ser Thr Ser Ala Thr Ala Val Val Thr Thr Val Ala Pro Ala Val Thr<br>                    270                    275                    280 | 1080 |
| gat gtc gtg act gtc acc gat gta gtt acc gtg acc acc gtc atc acc<br>Asp Val Val Thr Val Thr Asp Val Val Thr Val Thr Thr Val Ile Thr<br>                    285                    290                    295 | 1128 |
| act act gtc ctt taa aaccctggc aaagttcatt gcgtgatctg tcaaccctga<br>Thr Thr Val Leu<br>          300 | 1183 |
| cctgtttccc ccatttttcc ggatccaagt ctttgagaac atctgtttag ctgttcgagc | 1243 |
| aactttctac cattttctct tctttctctg aacctgcttt cggattgtac attttttcaac | 1303 |
| ttcatttttta tgtccatatt tgtgacatca tttagcttta ggcca | 1348 |

<210> SEQ ID NO 14
<211> LENGTH: 322
<212> TYPE: PRT
<213> ORGANISM: Acremonium cellulolyticus

<400> SEQUENCE: 14

Met Pro Ser Thr Lys Val Ala Ala Leu Ser Ala Val Leu Ala Leu Ala
       -20                         -15                          -10

Ser Thr Val Ala Gly His Gly Phe Val Gln Asn Ile Val Ile Asp Gly
-5              -1  1                  5                          10

Lys Ser Tyr Ser Gly Tyr Leu Val Asn Gln Phe Pro Tyr Glu Ser Asn
               15                    20                    25

Pro Pro Ala Val Ile Gly Trp Ala Thr Thr Ala Thr Asp Leu Gly Phe
          30                    35                    40

Val Ala Pro Ser Glu Tyr Thr Asn Ala Asp Ile Ile Cys His Lys Asn
45                        50                    55

Ala Thr Pro Gly Ala Leu Ser Ala Pro Val Ala Ala Gly Gly Thr Val
60                        65                    70                    75

Glu Leu Gln Trp Thr Thr Trp Pro Asp Ser His His Gly Pro Val Ile
               80                    85                    90

Ser Tyr Leu Ala Asn Cys Asn Gly Asn Cys Ser Thr Val Asp Lys Thr
               95                    100                    105

Lys Leu Asn Phe Val Lys Ile Asp Gln Gly Gly Leu Ile Asp Asp Thr

```
              110                 115                 120
Thr Pro Pro Gly Thr Trp Ala Ser Asp Lys Leu Ile Ala Ala Asn Asn
    125                 130                 135

Ser Trp Thr Val Thr Ile Pro Ser Thr Ile Ala Pro Gly Asn Tyr Val
140                 145                 150                 155

Leu Arg His Glu Ile Ile Ala Leu His Ser Ala Gly Asn Ala Asp Gly
                160                 165                 170

Ala Gln Asn Tyr Pro Gln Cys Ile Asn Leu Glu Ile Thr Gly Ser Gly
            175                 180                 185

Thr Ala Ala Pro Ser Gly Thr Ala Gly Glu Lys Leu Tyr Thr Ser Thr
        190                 195                 200

Asp Pro Gly Ile Leu Val Asn Ile Tyr Gln Ser Leu Ser Thr Tyr Val
    205                 210                 215

Ile Pro Gly Pro Thr Leu Trp Ser Gly Ala Ala Asn Gly Ala Val Ala
220                 225                 230                 235

Thr Gly Ser Ala Thr Ala Val Ala Thr Thr Ala Ala Ala Ser Ala Thr
                240                 245                 250

Ala Thr Pro Thr Thr Leu Val Thr Ser Val Ala Pro Ala Ser Ser Thr
            255                 260                 265

Ser Ala Thr Ala Val Val Thr Thr Val Ala Pro Ala Val Thr Asp Val
        270                 275                 280

Val Thr Val Thr Asp Val Val Thr Val Thr Thr Val Ile Thr Thr Thr
    285                 290                 295

Val Leu
300

<210> SEQ ID NO 15
<211> LENGTH: 2052
<212> TYPE: DNA
<213> ORGANISM: Acremonium cellulolyticus
<220> FEATURE:
<221> NAME/KEY: sig_peptide
<222> LOCATION: (238)..(321)
<220> FEATURE:
<221> NAME/KEY: exon
<222> LOCATION: (238)..(783)
<220> FEATURE:
<221> NAME/KEY: CDS
<222> LOCATION: (238)..(783)
<220> FEATURE:
<221> NAME/KEY: mat_peptide
<222> LOCATION: join (322..783,851..1137,1206..1702,1757..1884)
<220> FEATURE:
<221> NAME/KEY: Intron
<222> LOCATION: (784)..(850)
<220> FEATURE:
<221> NAME/KEY: exon
<222> LOCATION: (851)..(1137)
<220> FEATURE:
<221> NAME/KEY: CDS
<222> LOCATION: (851)..(1137)
<220> FEATURE:
<221> NAME/KEY: Intron
<222> LOCATION: (1138)..(1205)
<220> FEATURE:
<221> NAME/KEY: exon
<222> LOCATION: (1206)..(1702)
<220> FEATURE:
<221> NAME/KEY: CDS
<222> LOCATION: (1206)..(1702)
<220> FEATURE:
<221> NAME/KEY: Intron
<222> LOCATION: (1703)..(1756)
<220> FEATURE:
<221> NAME/KEY: exon
<222> LOCATION: (1757)..(1887)
```

<220> FEATURE:
<221> NAME/KEY: CDS
<222> LOCATION: (1757)..(1887)

<400> SEQUENCE: 15

```
ctccgtcaag tgcgaagtat attgtaactt cgagatctac tcaatatcca cttttgctaa      60
aacgccacga agccaccaaa gcctccaccg ctataaggaa gctcggagct tctgcgttcg     120
tcgcatgcgg gagaaaggtt cattttttct tgctagtcat aaacttcttt actttgattt     180 ccttttttg taaaaaaata tcttgctgtg aagaaaagca tcacagtctc agcaaaa        237
```

| | | | | | | | | | | | | | | | | |
|---|---|---|---|---|---|---|---|---|---|---|---|---|---|---|---|---|
| atg | ggc | tct | aca | tct | cct | gcc | caa | gcc | tca | ttg | cct | cgc | gac | ttc | gaa | 285 |
| Met | Gly | Ser | Thr | Ser | Pro | Ala | Gln | Ala | Ser | Leu | Pro | Arg | Asp | Phe | Glu | |
| | | | -25 | | | | -20 | | | | | -15 | | | | |
| tgg | ggg | ttt | gcg | aca | gca | tcc | tat | cag | atc | gaa | gga | gct | gtc | aat | gaa | 333 |
| Trp | Gly | Phe | Ala | Thr | Ala | Ser | Tyr | Gln | Ile | Glu | Gly | Ala | Val | Asn | Glu | |
| -10 | | | | -5 | | | | | -1 | 1 | | | | | | |
| gat | ggt | cgc | gga | aag | tca | atc | tgg | gat | acc | ttc | tgt | cac | ttg | gag | cca | 381 |
| Asp | Gly | Arg | Gly | Lys | Ser | Ile | Trp | Asp | Thr | Phe | Cys | His | Leu | Glu | Pro | |
| 5 | | | | 10 | | | | | 15 | | | | | 20 | | |
| aca | aga | aca | aag | ggc | gcc | agt | ggt | gat | gtt | gca | tgc | gac | cat | tac | cat | 429 |
| Thr | Arg | Thr | Lys | Gly | Ala | Ser | Gly | Asp | Val | Ala | Cys | Asp | His | Tyr | His | |
| | | | 25 | | | | | 30 | | | | | 35 | | | |
| cgc | tac | gag | gaa | gat | ttt | gat | ctc | tta | tcc | aaa | tac | ggc | gcc | aag | gca | 477 |
| Arg | Tyr | Glu | Glu | Asp | Phe | Asp | Leu | Leu | Ser | Lys | Tyr | Gly | Ala | Lys | Ala | |
| | 40 | | | | | 45 | | | | | 50 | | | | | |
| tat | cgt | ttc | tct | atc | tct | tgg | tcg | aga | att | att | cct | gac | ggt | gga | aga | 525 |
| Tyr | Arg | Phe | Ser | Ile | Ser | Trp | Ser | Arg | Ile | Ile | Pro | Asp | Gly | Gly | Arg | |
| | | 55 | | | | | 60 | | | | | 65 | | | | |
| gga | gat | gcc | gtg | aac | gag | cag | gga | atc | gcg | ttc | tat | aac | cgg | ctt | att | 573 |
| Gly | Asp | Ala | Val | Asn | Glu | Gln | Gly | Ile | Ala | Phe | Tyr | Asn | Arg | Leu | Ile | |
| | 70 | | | | | 75 | | | | | 80 | | | | | |
| gac | tct | ctg | ctt | tct | agg | ggt | att | gta | cct | tgg | gtg | act | tta | tac | cac | 621 |
| Asp | Ser | Leu | Leu | Ser | Arg | Gly | Ile | Val | Pro | Trp | Val | Thr | Leu | Tyr | His | |
| 85 | | | | | 90 | | | | | 95 | | | | | 100 | |
| tgg | gat | ctg | ccc | caa | agt | ctt | cac | gac | aga | tat | ggc | ggc | tgg | ctg | aat | 669 |
| Trp | Asp | Leu | Pro | Gln | Ser | Leu | His | Asp | Arg | Tyr | Gly | Gly | Trp | Leu | Asn | |
| | | | 105 | | | | | 110 | | | | | 115 | | | |
| gtg | gag | gag | tca | cag | tta | gat | ttt | gag | cga | tat | gcc | cgg | atc | tgc | tat | 717 |
| Val | Glu | Glu | Ser | Gln | Leu | Asp | Phe | Glu | Arg | Tyr | Ala | Arg | Ile | Cys | Tyr | |
| | | | 120 | | | | | 125 | | | | | 130 | | | |
| gag | cgc | ttt | gga | gat | cga | gtc | aag | aac | tgg | att | acc | ctg | aat | gag | ccg | 765 |
| Glu | Arg | Phe | Gly | Asp | Arg | Val | Lys | Asn | Trp | Ile | Thr | Leu | Asn | Glu | Pro | |
| | 135 | | | | | 140 | | | | | 145 | | | | | |
| tgg | att | gtt | tca | att | ttt | gtaagcattt tagttttctt cgctttcttg | | | | | | | | | 813 |
| Trp | Ile | Val | Ser | Ile | Phe | | | | | | | | | | | |
| | 150 | | | | | | | | | | | | | | | |

```
tcctatcgaa gtggaagttg gagctgacat tctatag
```
| | | | | | | | | | |
|---|---|---|---|---|---|---|---|---|---|
| | | | | | | gga | tat | tca | aca ggt gga | 868 |
| | | | | | | Gly | Tyr | Ser | Thr Gly Gly | |
| | | | | | | | 155 | | 160 | |
| aac | gcc | cca | gga | aga | agc | agc | gtc | aat | cct caa tct tct gag ggt aac | 916 |
| Asn | Ala | Pro | Gly | Arg | Ser | Ser | Val | Asn | Pro Gln Ser Ser Glu Gly Asn | |
| | | | | 165 | | | | | 170 175 | |
| tct | gcg | aca | gag | ccc | tgg | ata | gtc | gga | agg gct ctc atc cta agc cac | 964 |
| Ser | Ala | Thr | Glu | Pro | Trp | Ile | Val | Gly | Arg Ala Leu Ile Leu Ser His | |
| | | 180 | | | | | 185 | | 190 | |
| gcg | cgc | gcg | gtc | tca | ctt | tac | aac | aaa | gaa ttc cga tca aca caa aag | 1012 |
| Ala | Arg | Ala | Val | Ser | Leu | Tyr | Asn | Lys | Glu Phe Arg Ser Thr Gln Lys | |
| | 195 | | | | | 200 | | | 205 | |
| gga | aga | att | gga | ata | tct | ctg | aat | gga | gac ttt ttt gaa cct tgg gat | 1060 |

```
Gly Arg Ile Gly Ile Ser Leu Asn Gly Asp Phe Phe Glu Pro Trp Asp
        210                 215                 220 gcc caa gat gag cgt gat cgc gag gca gct gag aga aga atg gaa ttt      1108
Ala Gln Asp Glu Arg Asp Arg Glu Ala Ala Glu Arg Arg Met Glu Phe
225                 230                 235                 240 cat att gga tgg ttt gcc aat ccg gtg tg  gtacgtgtta ttttcatcta        1157
His Ile Gly Trp Phe Ala Asn Pro Val Cys
                245                 250 tgtgttatta tacacaaaag ctaactctta tcgcgtccac gaaaaaag c ctc gca       1212
                                                      Leu Ala cag gac tat cca aag tgt atg aga gag cag ctg aat gac cgt cta ccc      1260
Gln Asp Tyr Pro Lys Cys Met Arg Glu Gln Leu Asn Asp Arg Leu Pro
                255                 260                 265 aag ttc aca gac tcc gaa ttt acc ctg ctt cgc gaa gcc gat ata gac      1308
Lys Phe Thr Asp Ser Glu Phe Thr Leu Leu Arg Glu Ala Asp Ile Asp
270                 275                 280 ttc tac gga atg aat tat tac aca tct caa ttc gcc cgc cat cgc gac      1356
Phe Tyr Gly Met Asn Tyr Tyr Thr Ser Gln Phe Ala Arg His Arg Asp
285                 290                 295                 300 gaa act cct tcc aag aat gat tat ttg gga aat gta gaa gaa ctc cag      1404
Glu Thr Pro Ser Lys Asn Asp Tyr Leu Gly Asn Val Glu Glu Leu Gln
                305                 310                 315 gag aac aag gac ggc gtg tca gtc ggc gaa ccg tct ggg gtt cat tgg      1452
Glu Asn Lys Asp Gly Val Ser Val Gly Glu Pro Ser Gly Val His Trp
            320                 325                 330 ctt cgg tcg acc cca aag ctg ttt aga aag cat ttg act cga att tac      1500
Leu Arg Ser Thr Pro Lys Leu Phe Arg Lys His Leu Thr Arg Ile Tyr
                335                 340                 345 cgc aaa tat gga aaa ccc gtc tac gtt act gag aat ggc tgt ccc tgt      1548
Arg Lys Tyr Gly Lys Pro Val Tyr Val Thr Glu Asn Gly Cys Pro Cys
350                 355                 360 cca gga gag gag aag atg acc gtg act gag gca gtg aac gat aca tat      1596
Pro Gly Glu Glu Lys Met Thr Val Thr Glu Ala Val Asn Asp Thr Tyr
365                 370                 375                 380 cga atc cgg tat ttc gaa gac cat atc gag gct ctt gcg ctg gca cgc      1644
Arg Ile Arg Tyr Phe Glu Asp His Ile Glu Ala Leu Ala Leu Ala Arg
                385                 390                 395 agc gaa gat ggc tct gac att aag gga tac ttt gcc tgg tca ctg atg      1692
Ser Glu Asp Gly Ser Asp Ile Lys Gly Tyr Phe Ala Trp Ser Leu Met
                400                 405                 410 gat aat tta g gtatgtttcc gggactcgct attctgactc aagcaacaac            1742
Asp Asn Leu
        415 tgacatcttc ttag aa tgg tct gat ggg tac gga gtt cgg ttt ggt gcc       1791
                Glu Trp Ser Asp Gly Tyr Gly Val Arg Phe Gly Ala
                                420                 425 act ttc act gac tat aat acc ctt gaa agg acc ccg aaa cag tct gca      1839
Thr Phe Thr Asp Tyr Asn Thr Leu Glu Arg Thr Pro Lys Gln Ser Ala
            430                 435                 440 ttg ctc ttg aaa ggg att ttc gag aaa tac ata gag ccg agg aac tag      1887
Leu Leu Leu Lys Gly Ile Phe Glu Lys Tyr Ile Glu Pro Arg Asn
                445                 450                 455 tacctaggaa caatattata gagtcaaatg tcacgaggct atatacctgt agaatgggaa    1947
ctagctccag cctcgtagat cttagaatac acgaaaaatg tcaaaatgtc actagctact   2007
ccgtaaagtc ggggaacatg agtaagcagt tagtattagc gagcc                   2052

<210> SEQ ID NO 16
<211> LENGTH: 486
```

<212> TYPE: PRT
<213> ORGANISM: Acremonium cellulolyticus

<400> SEQUENCE: 16

```
Met Gly Ser Thr Ser Pro Ala Gln Ala Ser Leu Pro Arg Asp Phe Glu
            -25                 -20                 -15
Trp Gly Phe Ala Thr Ala Ser Tyr Gln Ile Glu Gly Ala Val Asn Glu
            -10                  -5                  -1   1
Asp Gly Arg Gly Lys Ser Ile Trp Asp Thr Phe Cys His Leu Glu Pro
 5               10                  15                  20
Thr Arg Thr Lys Gly Ala Ser Gly Asp Val Ala Cys Asp His Tyr His
                 25                  30                  35
Arg Tyr Glu Glu Asp Phe Asp Leu Leu Ser Lys Tyr Gly Ala Lys Ala
                 40                  45                  50
Tyr Arg Phe Ser Ile Ser Trp Ser Arg Ile Ile Pro Asp Gly Gly Arg
                 55                  60                  65
Gly Asp Ala Val Asn Glu Gln Gly Ile Ala Phe Tyr Asn Arg Leu Ile
 70                  75                  80
Asp Ser Leu Leu Ser Arg Gly Ile Val Pro Trp Val Thr Leu Tyr His
 85                  90                  95                 100
Trp Asp Leu Pro Gln Ser Leu His Asp Arg Tyr Gly Gly Trp Leu Asn
                105                 110                 115
Val Glu Glu Ser Gln Leu Asp Phe Glu Arg Tyr Ala Arg Ile Cys Tyr
                120                 125                 130
Glu Arg Phe Gly Asp Arg Val Lys Asn Trp Ile Thr Leu Asn Glu Pro
                135                 140                 145
Trp Ile Val Ser Ile Phe Gly Tyr Ser Thr Gly Gly Asn Ala Pro Gly
                150                 155                 160
Arg Ser Ser Val Asn Pro Gln Ser Ser Glu Gly Asn Ser Ala Thr Glu
165                 170                 175                 180
Pro Trp Ile Val Gly Arg Ala Leu Ile Leu Ser His Ala Arg Ala Val
                185                 190                 195
Ser Leu Tyr Asn Lys Glu Phe Arg Ser Thr Gln Lys Gly Arg Ile Gly
                200                 205                 210
Ile Ser Leu Asn Gly Asp Phe Phe Glu Pro Trp Asp Ala Gln Asp Glu
                215                 220                 225
Arg Asp Arg Glu Ala Ala Glu Arg Met Glu Phe His Ile Gly Trp
                230                 235                 240
Phe Ala Asn Pro Val Cys Leu Ala Gln Asp Tyr Pro Lys Cys Met Arg
245                 250                 255                 260
Glu Gln Leu Asn Asp Arg Leu Pro Lys Phe Thr Asp Ser Glu Phe Thr
                265                 270                 275
Leu Leu Arg Glu Ala Asp Ile Asp Phe Tyr Gly Met Asn Tyr Tyr Thr
                280                 285                 290
Ser Gln Phe Ala Arg His Arg Asp Glu Thr Pro Ser Lys Asn Asp Tyr
                295                 300                 305
Leu Gly Asn Val Glu Glu Leu Gln Glu Asn Lys Asp Gly Val Ser Val
                310                 315                 320
Gly Glu Pro Ser Gly Val His Trp Leu Arg Ser Thr Pro Lys Leu Phe
325                 330                 335                 340
Arg Lys His Leu Thr Arg Ile Tyr Arg Lys Tyr Gly Lys Pro Val Tyr
                345                 350                 355
Val Thr Glu Asn Gly Cys Pro Cys Pro Gly Glu Glu Lys Met Thr Val
                360                 365                 370
```

```
Thr Glu Ala Val Asn Asp Thr Tyr Arg Ile Arg Tyr Phe Glu Asp His
    375                 380                 385

Ile Glu Ala Leu Ala Leu Ala Arg Ser Glu Asp Gly Ser Asp Ile Lys
    390                 395                 400

Gly Tyr Phe Ala Trp Ser Leu Met Asp Asn Leu Glu Trp Ser Asp Gly
405                 410                 415                 420

Tyr Gly Val Arg Phe Gly Ala Thr Phe Thr Asp Tyr Asn Thr Leu Glu
                425                 430                 435

Arg Thr Pro Lys Gln Ser Ala Leu Leu Leu Lys Gly Ile Phe Glu Lys
            440                 445                 450

Tyr Ile Glu Pro Arg Asn
            455

<210> SEQ ID NO 17
<211> LENGTH: 1931
<212> TYPE: DNA
<213> ORGANISM: Acremonium cellulolyticus
<220> FEATURE:
<221> NAME/KEY: sig_peptide
<222> LOCATION: (66)..(227)
<220> FEATURE:
<221> NAME/KEY: exon
<222> LOCATION: (66)..(148)
<220> FEATURE:
<221> NAME/KEY: CDS
<222> LOCATION: (66)..(148)
<220> FEATURE:
<221> NAME/KEY: Intron
<222> LOCATION: (149)..(211)
<220> FEATURE:
<221> NAME/KEY: exon
<222> LOCATION: (212)..(403)
<220> FEATURE:
<221> NAME/KEY: CDS
<222> LOCATION: (212)..(403)
<220> FEATURE:
<221> NAME/KEY: mat_peptide
<222> LOCATION: join (228..403,461..933,989..1574,1627..1762)
<220> FEATURE:
<221> NAME/KEY: Intron
<222> LOCATION: (404)..(460)
<220> FEATURE:
<221> NAME/KEY: exon
<222> LOCATION: (461)..(933)
<220> FEATURE:
<221> NAME/KEY: CDS
<222> LOCATION: (461)..(933)
<220> FEATURE:
<221> NAME/KEY: Intron
<222> LOCATION: (934)..(988)
<220> FEATURE:
<221> NAME/KEY: exon
<222> LOCATION: (989)..(1574)
<220> FEATURE:
<221> NAME/KEY: CDS
<222> LOCATION: (989)..(1574)
<220> FEATURE:
<221> NAME/KEY: Intron
<222> LOCATION: (1575)..(1626)
<220> FEATURE:
<221> NAME/KEY: exon
<222> LOCATION: (1627)..(1765)
<220> FEATURE:
<221> NAME/KEY: CDS
<222> LOCATION: (1627)..(1765)

<400> SEQUENCE: 17
ttctctcact ttcccttcc atccgcttac cgagtcgcag aatcacatcc aacacatctc      60 cgagt atg ggt agc gta act agt acc aac ggc gag act ccc cag tcc aaa    110
      Met Gly Ser Val Thr Ser Thr Asn Gly Glu Thr Pro Gln Ser Lys
```

|  | -30 |  |  |  | -25 |  |  |  | -20 |  |  |  |
|---|---|---|---|---|---|---|---|---|---|---|---|---|
| ctg | ccg | gca | gac | ttt | gtc | tgg | gga | tac | gca | acg | gcc | ag | gtgagattac | 158 |
| Leu | Pro | Ala | Asp | Phe | Val | Trp | Gly | Tyr | Ala | Thr | Ala | Ser |  |
|  |  | -15 |  |  |  |  | -10 |  |  |  |  |  |  | tcgctattca tgtgtgtaga agaaacctat ttaccgtctt gttttggttc tag c tac 215
                                                                                Tyr
                                                                                -5

| cag | atc | gaa | gga | gcg | tat | gac | gaa | gac | ggc | cga | gga | cct | tcc | atc | tgg | 263 |
|---|---|---|---|---|---|---|---|---|---|---|---|---|---|---|---|---|
| Gln | Ile | Glu | Gly | Ala | Tyr | Asp | Glu | Asp | Gly | Arg | Gly | Pro | Ser | Ile | Trp |  |
|  | -1 | 1 |  |  |  | 5 |  |  |  |  | 10 |  |  |  |  |  |

| gat | aca | ttc | agc | aag | aca | cct | gga | aaa | gta | gag | gat | ggc | acc | aat | ggc | 311 |
|---|---|---|---|---|---|---|---|---|---|---|---|---|---|---|---|---|
| Asp | Thr | Phe | Ser | Lys | Thr | Pro | Gly | Lys | Val | Glu | Asp | Gly | Thr | Asn | Gly |  |
|  |  | 15 |  |  |  | 20 |  |  |  |  | 25 |  |  |  |  |  |

| gac | gtg | gcc | tgc | gac | tcc | tac | cac | cgt | aca | cat | gag | gat | att | gcg | att | 359 |
|---|---|---|---|---|---|---|---|---|---|---|---|---|---|---|---|---|
| Asp | Val | Ala | Cys | Asp | Ser | Tyr | His | Arg | Thr | His | Glu | Asp | Ile | Ala | Ile |  |
|  | 30 |  |  |  |  | 35 |  |  |  |  | 40 |  |  |  |  |  |

| ctg | aag | caa | tat | ggt | gcc | aag | ctg | tac | cgc | ttt | tct | ctg | tcc | tg |  | 403 |
|---|---|---|---|---|---|---|---|---|---|---|---|---|---|---|---|---|
| Leu | Lys | Gln | Tyr | Gly | Ala | Lys | Leu | Tyr | Arg | Phe | Ser | Leu | Ser | Trp |  |  |
| 45 |  |  |  |  | 50 |  |  |  |  | 55 |  |  |  |  |  |  | gtatagctcc cttcggcttc ttgcgccaga atataactga cagtattgat aatcaag g 461

| ccc | cga | atc | att | cct | cta | ggt | ggc | cga | aac | gac | ccc | atc | aac | caa | aag | 509 |
|---|---|---|---|---|---|---|---|---|---|---|---|---|---|---|---|---|
| Pro | Arg | Ile | Ile | Pro | Leu | Gly | Gly | Arg | Asn | Asp | Pro | Ile | Asn | Gln | Lys |  |
| 60 |  |  |  |  | 65 |  |  |  |  | 70 |  |  |  |  | 75 |  |

| gga | ata | gac | ttt | tac | tcc | aaa | ttc | atc | gac | gat | ctc | cac | gcc | gct | gga | 557 |
|---|---|---|---|---|---|---|---|---|---|---|---|---|---|---|---|---|
| Gly | Ile | Asp | Phe | Tyr | Ser | Lys | Phe | Ile | Asp | Asp | Leu | His | Ala | Ala | Gly |  |
|  |  |  |  | 80 |  |  |  |  | 85 |  |  |  |  | 90 |  |  |

| atc | gag | ccc | ttc | gtc | acc | ttg | tac | cac | tgg | gat | ctt | ccc | gac | gag | ctg | 605 |
|---|---|---|---|---|---|---|---|---|---|---|---|---|---|---|---|---|
| Ile | Glu | Pro | Phe | Val | Thr | Leu | Tyr | His | Trp | Asp | Leu | Pro | Asp | Glu | Leu |  |
|  |  |  | 95 |  |  |  |  | 100 |  |  |  |  | 105 |  |  |  |

| ttc | aag | aga | tac | ggc | ggc | ccc | ctc | aac | aag | gac | gaa | ttc | gtg | gct | gac | 653 |
|---|---|---|---|---|---|---|---|---|---|---|---|---|---|---|---|---|
| Phe | Lys | Arg | Tyr | Gly | Gly | Pro | Leu | Asn | Lys | Asp | Glu | Phe | Val | Ala | Asp |  |
|  |  | 110 |  |  |  |  | 115 |  |  |  |  | 120 |  |  |  |  |

| tat | gcg | aac | ttc | gcc | cgc | atc | gca | ttc | cag | agc | ttt | gga | cac | aaa | gtc | 701 |
|---|---|---|---|---|---|---|---|---|---|---|---|---|---|---|---|---|
| Tyr | Ala | Asn | Phe | Ala | Arg | Ile | Ala | Phe | Gln | Ser | Phe | Gly | His | Lys | Val |  |
|  | 125 |  |  |  |  | 130 |  |  |  |  | 135 |  |  |  |  |  |

| aag | cat | tgg | gtt | acc | ttc | aat | gaa | cca | tgg | tgt | agc | tcc | gtg | ctc | ggt | 749 |
|---|---|---|---|---|---|---|---|---|---|---|---|---|---|---|---|---|
| Lys | His | Trp | Val | Thr | Phe | Asn | Glu | Pro | Trp | Cys | Ser | Ser | Val | Leu | Gly |  |
| 140 |  |  |  |  | 145 |  |  |  |  | 150 |  |  |  |  | 155 |  |

| ttc | aat | atc | ggt | aag | cat | gcg | cca | gga | cgg | acg | agc | gat | cgc | aag | aag | 797 |
|---|---|---|---|---|---|---|---|---|---|---|---|---|---|---|---|---|
| Phe | Asn | Ile | Gly | Lys | His | Ala | Pro | Gly | Arg | Thr | Ser | Asp | Arg | Lys | Lys |  |
|  |  |  | 160 |  |  |  |  | 165 |  |  |  |  | 170 |  |  |  |

| aac | ccg | gtt | ggt | gat | ggt | gtg | cgt | gag | cca | tgg | att | gct | ggt | cat | tcc | 845 |
|---|---|---|---|---|---|---|---|---|---|---|---|---|---|---|---|---|
| Asn | Pro | Val | Gly | Asp | Gly | Val | Arg | Glu | Pro | Trp | Ile | Ala | Gly | His | Ser |  |
|  | 175 |  |  |  |  | 180 |  |  |  |  | 185 |  |  |  |  |  |

| ctt | ttg | gtg | gct | cac | ggc | acg | gct | gtt | gat | atc | tac | cgg | aag | gaa | ttt | 893 |
|---|---|---|---|---|---|---|---|---|---|---|---|---|---|---|---|---|
| Leu | Leu | Val | Ala | His | Gly | Thr | Ala | Val | Asp | Ile | Tyr | Arg | Lys | Glu | Phe |  |
|  | 190 |  |  |  |  | 195 |  |  |  |  | 200 |  |  |  |  |  |

| aag | cct | aca | cag | ggc | gga | gaa | att | ggc | att | aca | ctc | aat | g | gttagatcga | 943 |
|---|---|---|---|---|---|---|---|---|---|---|---|---|---|---|---|
| Lys | Pro | Thr | Gln | Gly | Gly | Glu | Ile | Gly | Ile | Thr | Leu | Asn |  |  |
| 205 |  |  |  |  | 210 |  |  |  |  | 215 |  |  |  |  | aatattcccc aacgcatgac aatcatgcgc taatatgaat tcaag gt    gac tgg gcc 999
                                                                                                      Gly Asp Trp Ala
                                                                                                      220

| gaa | ccc | tgg | gac | ccc | gaa | gac | cca | gaa | gac | att | gaa | gcc | ccc | acc | cgc | 1047 |
|---|---|---|---|---|---|---|---|---|---|---|---|---|---|---|---|---|
| Glu | Pro | Trp | Asp | Pro | Glu | Asp | Pro | Glu | Asp | Ile | Glu | Ala | Pro | Thr | Arg |  |
|  |  |  | 225 |  |  |  |  | 230 |  |  |  |  | 235 |  |  |  |

| aaa | ctc | gaa | ttc | gcc | atc | tcc | tgg | ttt | gca | gac | ccc | atc | tac | ctt | ggc | 1095 |
|---|---|---|---|---|---|---|---|---|---|---|---|---|---|---|---|---|
| Lys | Leu | Glu | Phe | Ala | Ile | Ser | Trp | Phe | Ala | Asp | Pro | Ile | Tyr | Leu | Gly |  |
|  |  | 240 |  |  |  |  | 245 |  |  |  |  | 250 |  |  |  |  |

```
aaa tac ccc gac agc gtc gtg aaa caa atc ggc gac cgt ctc cca ccc      1143
Lys Tyr Pro Asp Ser Val Val Lys Gln Ile Gly Asp Arg Leu Pro Pro
        255                 260                 265 ttg aca ccc gat gaa gta gcc ttg atc aag gga agc aac gac ttt tac      1191
Leu Thr Pro Asp Glu Val Ala Leu Ile Lys Gly Ser Asn Asp Phe Tyr
    270                 275                 280 ggc atg aac cac tac tgc gca aac tac atc cgt cac cga gaa ggt gaa      1239
Gly Met Asn His Tyr Cys Ala Asn Tyr Ile Arg His Arg Glu Gly Glu
285                 290                 295                 300 gcg gat cca gac gac aca gcc gga aac ttg gac cat ttg ttt gag gat      1287
Ala Asp Pro Asp Asp Thr Ala Gly Asn Leu Asp His Leu Phe Glu Asp
                305                 310                 315 aaa ttc gga aac tcg att gga ccc gag acg aat tgt gaa tgg ctt cgc      1335
Lys Phe Gly Asn Ser Ile Gly Pro Glu Thr Asn Cys Glu Trp Leu Arg
            320                 325                 330 cct cat ccc ttg gga ttc agg aag ttg ttg aaa tgg ctt tcg gat cgt      1383
Pro His Pro Leu Gly Phe Arg Lys Leu Leu Lys Trp Leu Ser Asp Arg
        335                 340                 345 tat ggt tat ccc aaa atc tat gtt acg gag aac ggg acg agt atc aag      1431
Tyr Gly Tyr Pro Lys Ile Tyr Val Thr Glu Asn Gly Thr Ser Ile Lys
    350                 355                 360 ggc gag aac gac ttg cca cta gag gaa ctc ctc aat gat gag ttt agg      1479
Gly Glu Asn Asp Leu Pro Leu Glu Glu Leu Leu Asn Asp Glu Phe Arg
365                 370                 375                 380 gtg cag tat tac cgg gat tat gtc ggt gcc atg gct gat gct gct act      1527
Val Gln Tyr Tyr Arg Asp Tyr Val Gly Ala Met Ala Asp Ala Ala Thr
                385                 390                 395 ttt gac gga gtc aat gtt aag aaa tat atg gcc tgg agt ttg atg ga       1574
Phe Asp Gly Val Asn Val Lys Lys Tyr Met Ala Trp Ser Leu Met Asp
            400                 405                 410 gtaagtcaaa acatcaccta ttcggaaaga cttctgctaa tcgctctatt ag t aac      1630
                                                            Asn ttc gag tgg tcc gaa ggt tac caa tcc aga ttt ggt gtc aca tac gtc      1678
Phe Glu Trp Ser Glu Gly Tyr Gln Ser Arg Phe Gly Val Thr Tyr Val
        415                 420                 425 gac tac aag gac aac cag aaa cgt atc ccc aag aag agt gcc ctc gtc      1726
Asp Tyr Lys Asp Asn Gln Lys Arg Ile Pro Lys Lys Ser Ala Leu Val
430                 435                 440                 445 att gga gaa ttg ttc aac aaa tac atc tcg aaa gag tag acaatttcct       1775
Ile Gly Glu Leu Phe Asn Lys Tyr Ile Ser Lys Glu
                450                 455 cgaattttat gtttatatc ctatacacta tgtaaatagt gatccatcat ttttgtactt     1835
gttgagtttt tgtcttgata ttctcctttg gtgtgtagat tttaacaaac tgcaatcata    1895
tcacgctcgc tttggcccgc atcaggagca tcaatt                              1931

<210> SEQ ID NO 18
<211> LENGTH: 490
<212> TYPE: PRT
<213> ORGANISM: Acremonium cellulolyticus

<400> SEQUENCE: 18

Met Gly Ser Val Thr Ser Thr Asn Gly Glu Thr Pro Gln Ser Lys Leu
            -30                 -25                 -20

Pro Ala Asp Phe Val Trp Gly Tyr Ala Thr Ala Ser Tyr Gln Ile Glu
        -15                 -10                 -5

Gly Ala Tyr Asp Glu Asp Gly Arg Gly Pro Ser Ile Trp Asp Thr Phe
-1  1               5                   10                  15
```

Ser Lys Thr Pro Gly Lys Val Glu Asp Gly Thr Asn Gly Asp Val Ala
            20                  25                  30

Cys Asp Ser Tyr His Arg Thr His Glu Asp Ile Ala Ile Leu Lys Gln
            35                  40                  45

Tyr Gly Ala Lys Leu Tyr Arg Phe Ser Leu Ser Trp Pro Arg Ile Ile
            50                  55                  60

Pro Leu Gly Gly Arg Asn Asp Pro Ile Asn Gln Lys Gly Ile Asp Phe
65                  70                  75

Tyr Ser Lys Phe Ile Asp Asp Leu His Ala Ala Gly Ile Glu Pro Phe
80                  85                  90                  95

Val Thr Leu Tyr His Trp Asp Leu Pro Asp Glu Leu Phe Lys Arg Tyr
                    100                 105                 110

Gly Gly Pro Leu Asn Lys Asp Glu Phe Val Ala Asp Tyr Ala Asn Phe
                115                 120                 125

Ala Arg Ile Ala Phe Gln Ser Phe Gly His Lys Val Lys His Trp Val
                130                 135                 140

Thr Phe Asn Glu Pro Trp Cys Ser Ser Val Leu Gly Phe Asn Ile Gly
            145                 150                 155

Lys His Ala Pro Gly Arg Thr Ser Asp Arg Lys Lys Asn Pro Val Gly
160                 165                 170                 175

Asp Gly Val Arg Glu Pro Trp Ile Ala Gly His Ser Leu Leu Val Ala
                    180                 185                 190

His Gly Thr Ala Val Asp Ile Tyr Arg Lys Glu Phe Lys Pro Thr Gln
                195                 200                 205

Gly Gly Glu Ile Gly Ile Thr Leu Asn Gly Asp Trp Ala Glu Pro Trp
            210                 215                 220

Asp Pro Glu Asp Pro Glu Asp Ile Glu Ala Pro Thr Arg Lys Leu Glu
            225                 230                 235

Phe Ala Ile Ser Trp Phe Ala Asp Pro Ile Tyr Leu Gly Lys Tyr Pro
240                 245                 250                 255

Asp Ser Val Val Lys Gln Ile Gly Asp Arg Leu Pro Pro Leu Thr Pro
                    260                 265                 270

Asp Glu Val Ala Leu Ile Lys Gly Ser Asn Asp Phe Tyr Gly Met Asn
                275                 280                 285

His Tyr Cys Ala Asn Tyr Ile Arg His Arg Glu Gly Glu Ala Asp Pro
            290                 295                 300

Asp Asp Thr Ala Gly Asn Leu Asp His Leu Phe Glu Asp Lys Phe Gly
            305                 310                 315

Asn Ser Ile Gly Pro Glu Thr Asn Cys Glu Trp Leu Arg Pro His Pro
320                 325                 330                 335

Leu Gly Phe Arg Lys Leu Leu Lys Trp Leu Ser Asp Arg Tyr Gly Tyr
                    340                 345                 350

Pro Lys Ile Tyr Val Thr Glu Asn Gly Thr Ser Ile Lys Gly Glu Asn
                355                 360                 365

Asp Leu Pro Leu Glu Glu Leu Leu Asn Asp Gly Phe Arg Val Gln Tyr
            370                 375                 380

Tyr Arg Asp Tyr Val Gly Ala Met Ala Asp Ala Ala Thr Phe Asp Gly
            385                 390                 395

Val Asn Val Lys Lys Tyr Met Ala Trp Ser Leu Met Asp Asn Phe Glu
400                 405                 410                 415

Trp Ser Glu Gly Tyr Gln Ser Arg Phe Gly Val Thr Tyr Val Asp Tyr
                    420                 425                 430

Lys Asp Asn Gln Lys Arg Ile Pro Lys Lys Ser Ala Leu Val Ile Gly

Glu Leu Phe Asn Lys Tyr Ile Ser Lys Glu
    450                 455

<210> SEQ ID NO 19
<211> LENGTH: 20
<212> TYPE: DNA
<213> ORGANISM: Artificial Sequence
<220> FEATURE:
<223> OTHER INFORMATION: primer : ACC3-F

<400> SEQUENCE: 19
gggcgtctgt rttygartgt                                        20

<210> SEQ ID NO 20
<211> LENGTH: 20
<212> TYPE: DNA
<213> ORGANISM: Artificial Sequence
<220> FEATURE:
<223> OTHER INFORMATION: primer : ACC3-R

<400> SEQUENCE: 20
aaaatgtagt ctccccacca                                        20

<210> SEQ ID NO 21
<211> LENGTH: 20
<212> TYPE: DNA
<213> ORGANISM: Artificial Sequence
<220> FEATURE:
<223> OTHER INFORMATION: primer : ACC3-inv-F

<400> SEQUENCE: 21
acttccagac tttctggtcc                                        20

<210> SEQ ID NO 22
<211> LENGTH: 20
<212> TYPE: DNA
<213> ORGANISM: Artificial Sequence
<220> FEATURE:
<223> OTHER INFORMATION: primer : ACC3-inv-R

<400> SEQUENCE: 22
aggccgagag taagtatctc                                        20

<210> SEQ ID NO 23
<211> LENGTH: 20
<212> TYPE: DNA
<213> ORGANISM: Artificial Sequence
<220> FEATURE:
<223> OTHER INFORMATION: primer : pACC3-F

<400> SEQUENCE: 23
gaaggatggt agattgtccg                                        20

<210> SEQ ID NO 24
<211> LENGTH: 20
<212> TYPE: DNA
<213> ORGANISM: Artificial Sequence
<220> FEATURE:
<223> OTHER INFORMATION: primer : pACC3-R

<400> SEQUENCE: 24
accgagaagg atttctcgca                                        20

<210> SEQ ID NO 25

-continued

```
<211> LENGTH: 24
<212> TYPE: DNA
<213> ORGANISM: Artificial Sequence
<220> FEATURE:
<223> OTHER INFORMATION: primer : ACC3-N

<400> SEQUENCE: 25
atgaagacca gcatcatttc tatc                                          24

<210> SEQ ID NO 26
<211> LENGTH: 24
<212> TYPE: DNA
<213> ORGANISM: Artificial Sequence
<220> FEATURE:
<223> OTHER INFORMATION: primer : ACC3-C

<400> SEQUENCE: 26
tcatgggaaa taactctcca gaat                                          24

<210> SEQ ID NO 27
<211> LENGTH: 29
<212> TYPE: DNA
<213> ORGANISM: Artificial Sequence
<220> FEATURE:
<223> OTHER INFORMATION: primer : ACC5-F
<220> FEATURE:
<221> NAME/KEY: misc_feature
<222> LOCATION: (18)..(18)
<223> OTHER INFORMATION: "n" stands for any base
<220> FEATURE:
<221> NAME/KEY: misc_feature
<222> LOCATION: (27)..(27)
<223> OTHER INFORMATION: "n" stands for any base

<400> SEQUENCE: 27
cagcaggccc ccacccnga yaayytngc                                      29

<210> SEQ ID NO 28
<211> LENGTH: 23
<212> TYPE: DNA
<213> ORGANISM: Artificial Sequence
<220> FEATURE:
<223> OTHER INFORMATION: primer : ACC5-R

<400> SEQUENCE: 28
aattcgcggc cgctaaaaaa aaa                                           23

<210> SEQ ID NO 29
<211> LENGTH: 20
<212> TYPE: DNA
<213> ORGANISM: Artificial Sequence
<220> FEATURE:
<223> OTHER INFORMATION: primer : ACC5-inv-F

<400> SEQUENCE: 29
atctcacctg caacctacga                                               20

<210> SEQ ID NO 30
<211> LENGTH: 20
<212> TYPE: DNA
<213> ORGANISM: Artificial Sequence
<220> FEATURE:
<223> OTHER INFORMATION: primer : ACC5-inv-R

<400> SEQUENCE: 30
cctcttccgt tccacataaa                                               20
```

```
<210> SEQ ID NO 31
<211> LENGTH: 20
<212> TYPE: DNA
<213> ORGANISM: Artificial Sequence
<220> FEATURE:
<223> OTHER INFORMATION: primer : pACC5-F

<400> SEQUENCE: 31
attgctccgc ataggttcaa                                              20

<210> SEQ ID NO 32
<211> LENGTH: 20
<212> TYPE: DNA
<213> ORGANISM: Artificial Sequence
<220> FEATURE:
<223> OTHER INFORMATION: primer : pACC5-R

<400> SEQUENCE: 32
ttcagagtta gtgcctccag                                              20

<210> SEQ ID NO 33
<211> LENGTH: 25
<212> TYPE: DNA
<213> ORGANISM: Artificial Sequence
<220> FEATURE:
<223> OTHER INFORMATION: primer : ACC5-N

<400> SEQUENCE: 33
atggcgacta gaccattggc ttttg                                        25

<210> SEQ ID NO 34
<211> LENGTH: 25
<212> TYPE: DNA
<213> ORGANISM: Artificial Sequence
<220> FEATURE:
<223> OTHER INFORMATION: primer : ACC5-C

<400> SEQUENCE: 34
ctaaaggcac tgtgaatagt acgga                                        25

<210> SEQ ID NO 35
<211> LENGTH: 26
<212> TYPE: DNA
<213> ORGANISM: Artificial Sequence
<220> FEATURE:
<223> OTHER INFORMATION: primer : ACC6-F

<400> SEQUENCE: 35
gtgaacatcg ccggcttyga yttygg                                       26

<210> SEQ ID NO 36
<211> LENGTH: 23
<212> TYPE: DNA
<213> ORGANISM: Artificial Sequence
<220> FEATURE:
<223> OTHER INFORMATION: primer : ACC6-R

<400> SEQUENCE: 36
ccgttccacc gggcrtartt rtg                                          23

<210> SEQ ID NO 37
<211> LENGTH: 20
<212> TYPE: DNA
<213> ORGANISM: Artificial Sequence
<220> FEATURE:
<223> OTHER INFORMATION: primer : pACC6-F
```

<400> SEQUENCE: 37
ctctgcattg aatcccgaga                                                    20

<210> SEQ ID NO 38
<211> LENGTH: 20
<212> TYPE: DNA
<213> ORGANISM: Artificial Sequence
<220> FEATURE:
<223> OTHER INFORMATION: primer : pACC6-R

<400> SEQUENCE: 38
gcaacgctaa agtgctcatc                                                    20

<210> SEQ ID NO 39
<211> LENGTH: 24
<212> TYPE: DNA
<213> ORGANISM: Artificial Sequence
<220> FEATURE:
<223> OTHER INFORMATION: primer : ACC6-N

<400> SEQUENCE: 39
atgacaatca tctcaaaatt cggt                                               24

<210> SEQ ID NO 40
<211> LENGTH: 24
<212> TYPE: DNA
<213> ORGANISM: Artificial Sequence
<220> FEATURE:
<223> OTHER INFORMATION: primer : ACC6-C

<400> SEQUENCE: 40
tcaggatttc cactttggaa cgaa                                               24

<210> SEQ ID NO 41
<211> LENGTH: 28
<212> TYPE: DNA
<213> ORGANISM: Artificial Sequence
<220> FEATURE:
<223> OTHER INFORMATION: primer : ACC7-F
<220> FEATURE:
<221> NAME/KEY: misc_feature
<222> LOCATION: (18)..(18)
<223> OTHER INFORMATION: "n" stands for any base

<400> SEQUENCE: 41
cacgccatga tcgacccnca yaaytayg                                           28

<210> SEQ ID NO 42
<211> LENGTH: 22
<212> TYPE: DNA
<213> ORGANISM: Artificial Sequence
<220> FEATURE:
<223> OTHER INFORMATION: primer : ACC7-R
<220> FEATURE:
<221> NAME/KEY: misc_feature
<222> LOCATION: (14)..(14)
<223> OTHER INFORMATION: "n" stands for any base

<400> SEQUENCE: 42
accaggggcc ggcngyccac ca                                                 22

<210> SEQ ID NO 43
<211> LENGTH: 20
<212> TYPE: DNA
<213> ORGANISM: Artificial
<220> FEATURE:
<223> OTHER INFORMATION: primer : pACC7-F

```
<400> SEQUENCE: 43
cagtcagttg tgtagacacg                                              20

<210> SEQ ID NO 44
<211> LENGTH: 20
<212> TYPE: DNA
<213> ORGANISM: Artificial
<220> FEATURE:
<223> OTHER INFORMATION: primer : pACC7-R

<400> SEQUENCE: 44
actcagctgg gtcttcatag                                              20

<210> SEQ ID NO 45
<211> LENGTH: 24
<212> TYPE: DNA
<213> ORGANISM: Artificial Sequence
<220> FEATURE:
<223> OTHER INFORMATION: primer : ACC7-N

<400> SEQUENCE: 45
atgaggtcta catcaacatt tgta                                         24

<210> SEQ ID NO 46
<211> LENGTH: 24
<212> TYPE: DNA
<213> ORGANISM: Artificial Sequence
<220> FEATURE:
<223> OTHER INFORMATION: primer : ACC7-C

<400> SEQUENCE: 46
ctaaggggtg taggcctgca ggat                                         24

<210> SEQ ID NO 47
<211> LENGTH: 39
<212> TYPE: DNA
<213> ORGANISM: Artificial Sequence
<220> FEATURE:
<223> OTHER INFORMATION: primer : MSW-N

<400> SEQUENCE: 47
caacagagtc tatgcgctca atactcgagc tacaccagt                         39

<210> SEQ ID NO 48
<211> LENGTH: 22
<212> TYPE: DNA
<213> ORGANISM: Artificial Sequence
<220> FEATURE:
<223> OTHER INFORMATION: primer : MSW-C

<400> SEQUENCE: 48
ctaattgaca gctgcagacc aa                                           22

<210> SEQ ID NO 49
<211> LENGTH: 20
<212> TYPE: DNA
<213> ORGANISM: Artificial Sequence
<220> FEATURE:
<223> OTHER INFORMATION: primer : pACC8-F

<400> SEQUENCE: 49
aaagaccgcg tgttaggatc                                              20

<210> SEQ ID NO 50
```

<211> LENGTH: 20
<212> TYPE: DNA
<213> ORGANISM: Artificial Sequence
<220> FEATURE:
<223> OTHER INFORMATION: primer : pACC8-R

<400> SEQUENCE: 50
cgcgtaggaa ataagacacc                                          20

<210> SEQ ID NO 51
<211> LENGTH: 24
<212> TYPE: DNA
<213> ORGANISM: Artificial Sequence
<220> FEATURE:
<223> OTHER INFORMATION: primer : ACC8-N

<400> SEQUENCE: 51
atgaagctaa cttttctcct gaac                                     24

<210> SEQ ID NO 52
<211> LENGTH: 24
<212> TYPE: DNA
<213> ORGANISM: Artificial Sequence
<220> FEATURE:
<223> OTHER INFORMATION: primer : ACC8-C

<400> SEQUENCE: 52
ctaattgaca gatgcagacc aatg                                     24

<210> SEQ ID NO 53
<211> LENGTH: 22
<212> TYPE: DNA
<213> ORGANISM: Artificial Sequence
<220> FEATURE:
<223> OTHER INFORMATION: primer : ACC9-F

<400> SEQUENCE: 53
ccggctgcgg caartgytay ma                                       22

<210> SEQ ID NO 54
<211> LENGTH: 31
<212> TYPE: DNA
<213> ORGANISM: Artificial Sequence
<220> FEATURE:
<223> OTHER INFORMATION: primer : ACC9-R
<220> FEATURE:
<221> NAME/KEY: misc_feature
<222> LOCATION: (26)..(26)
<223> OTHER INFORMATION: "n" stands for any base
<220> FEATURE:
<221> NAME/KEY: misc_feature
<222> LOCATION: (29)..(29)
<223> OTHER INFORMATION: "n" stands for any base

<400> SEQUENCE: 54
agtaccactg gttctgcacc ttrcangtns c                             31

<210> SEQ ID NO 55
<211> LENGTH: 20
<212> TYPE: DNA
<213> ORGANISM: Artificial Sequence
<220> FEATURE:
<223> OTHER INFORMATION: primer : ACC9-inv-F

<400> SEQUENCE: 55
cgaagtgttt ggtgacaacg                                          20

```
<210> SEQ ID NO 56
<211> LENGTH: 20
<212> TYPE: DNA
<213> ORGANISM: Artificial Sequence
<220> FEATURE:
<223> OTHER INFORMATION: primer : ACC9-inv-R

<400> SEQUENCE: 56
gtggtagctg tatccgtagt                                           20

<210> SEQ ID NO 57
<211> LENGTH: 20
<212> TYPE: DNA
<213> ORGANISM: Artificial Sequence
<220> FEATURE:
<223> OTHER INFORMATION: primer : pACC9-F

<400> SEQUENCE: 57
tacattccga aggcacagtt                                           20

<210> SEQ ID NO 58
<211> LENGTH: 20
<212> TYPE: DNA
<213> ORGANISM: Artificial Sequence
<220> FEATURE:
<223> OTHER INFORMATION: primer : pACC9-R

<400> SEQUENCE: 58
ctgagctgat tatcctgacc                                           20

<210> SEQ ID NO 59
<211> LENGTH: 24
<212> TYPE: DNA
<213> ORGANISM: Artificial Sequence
<220> FEATURE:
<223> OTHER INFORMATION: primer : ACC9-N

<400> SEQUENCE: 59
atgaaggctt tctatctttc tctc                                      24

<210> SEQ ID NO 60
<211> LENGTH: 24
<212> TYPE: DNA
<213> ORGANISM: Artificial Sequence
<220> FEATURE:
<223> OTHER INFORMATION: primer : ACC9-C

<400> SEQUENCE: 60
ttaggacgag ctgacgcact ggta                                      24

<210> SEQ ID NO 61
<211> LENGTH: 27
<212> TYPE: DNA
<213> ORGANISM: Artificial Sequence
<220> FEATURE:
<223> OTHER INFORMATION: primer : ACC10-F
<220> FEATURE:
<221> NAME/KEY: misc_feature
<222> LOCATION: (22)..(22)
<223> OTHER INFORMATION: "n" stands for any base
<220> FEATURE:
<221> NAME/KEY: misc_feature
<222> LOCATION: (25)..(25)
<223> OTHER INFORMATION: "n" stands for any base

<400> SEQUENCE: 61
ggtgtacgtg ggcaccaayg gnmgngg                                   27
```

<210> SEQ ID NO 62
<211> LENGTH: 23
<212> TYPE: DNA
<213> ORGANISM: Artificial Sequence
<220> FEATURE:
<223> OTHER INFORMATION: primer : ACC10-R

<400> SEQUENCE: 62
aattcgcggc cgctaaaaaa aaa        23

<210> SEQ ID NO 63
<211> LENGTH: 20
<212> TYPE: DNA
<213> ORGANISM: Artificial Sequence
<220> FEATURE:
<223> OTHER INFORMATION: primer : ACC10-inv-F

<400> SEQUENCE: 63
ttctgctact gcggttgcta        20

<210> SEQ ID NO 64
<211> LENGTH: 20
<212> TYPE: DNA
<213> ORGANISM: Artificial Sequence
<220> FEATURE:
<223> OTHER INFORMATION: primer : ACC10-inv-R

<400> SEQUENCE: 64
gaataacgta ggtcgacaag        20

<210> SEQ ID NO 65
<211> LENGTH: 19
<212> TYPE: DNA
<213> ORGANISM: Artificial Sequence
<220> FEATURE:
<223> OTHER INFORMATION: primer : pACC10-F

<400> SEQUENCE: 65
cgttgaccga aagccactt        19

<210> SEQ ID NO 66
<211> LENGTH: 20
<212> TYPE: DNA
<213> ORGANISM: Artificial Sequence
<220> FEATURE:
<223> OTHER INFORMATION: primer : pACC10-R

<400> SEQUENCE: 66
tggcctaaag ctaaatgatg        20

<210> SEQ ID NO 67
<211> LENGTH: 25
<212> TYPE: DNA
<213> ORGANISM: Artificial Sequence
<220> FEATURE:
<223> OTHER INFORMATION: primer : ACC10-N

<400> SEQUENCE: 67
atgccttcta ctaaagtcgc tgccc        25

<210> SEQ ID NO 68
<211> LENGTH: 25
<212> TYPE: DNA
<213> ORGANISM: Artificial Sequence
<220> FEATURE:
<223> OTHER INFORMATION: primer : ACC10-C

```
<400> SEQUENCE: 68
ttaaaggaca gtagtggtga tgacg                                     25

<210> SEQ ID NO 69
<211> LENGTH: 28
<212> TYPE: DNA
<213> ORGANISM: Artificial Sequence
<220> FEATURE:
<223> OTHER INFORMATION: primer : BGLC-F

<400> SEQUENCE: 69
cctgggtgac cctgtaccay tgggayyt                                  28

<210> SEQ ID NO 70
<211> LENGTH: 24
<212> TYPE: DNA
<213> ORGANISM: Artificial Sequence
<220> FEATURE:
<223> OTHER INFORMATION: primer : BGLC-R
<220> FEATURE:
<221> NAME/KEY: misc_feature
<222> LOCATION: (22)..(22)
<223> OTHER INFORMATION: "n" stands for any base

<400> SEQUENCE: 70
tgggcaggag cagccrwwyt cngt                                      24

<210> SEQ ID NO 71
<211> LENGTH: 20
<212> TYPE: DNA
<213> ORGANISM: Artificial Sequence
<220> FEATURE:
<223> OTHER INFORMATION: primer : BGLC-inv-F

<400> SEQUENCE: 71
ggagttcttc tacatttccc                                           20

<210> SEQ ID NO 72
<211> LENGTH: 20
<212> TYPE: DNA
<213> ORGANISM: Artificial Sequence
<220> FEATURE:
<223> OTHER INFORMATION: primer : BGLC-inv-R

<400> SEQUENCE: 72
aacaaggacg gcgtgtcagt                                           20

<210> SEQ ID NO 73
<211> LENGTH: 20
<212> TYPE: DNA
<213> ORGANISM: Artificial Sequence
<220> FEATURE:
<223> OTHER INFORMATION: primer : pBGLC-F

<400> SEQUENCE: 73
ctccgtcaag tgcgaagtat                                           20

<210> SEQ ID NO 74
<211> LENGTH: 20
<212> TYPE: DNA
<213> ORGANISM: Artificial Sequence
<220> FEATURE:
<223> OTHER INFORMATION: primer : pBGLC-R

<400> SEQUENCE: 74
```
ggctcgctaa tactaactgc                                                    20

<210> SEQ ID NO 75
<211> LENGTH: 24
<212> TYPE: DNA
<213> ORGANISM: Artificial Sequence
<220> FEATURE:
<223> OTHER INFORMATION: primer : BGLC-N

<400> SEQUENCE: 75
atgggctcta catctcctgc ccaa                                               24

<210> SEQ ID NO 76
<211> LENGTH: 24
<212> TYPE: DNA
<213> ORGANISM: Artificial Sequence
<220> FEATURE:
<223> OTHER INFORMATION: primer : BGLC-C

<400> SEQUENCE: 76
ctagttcctc ggctctatgt attt                                               24

<210> SEQ ID NO 77
<211> LENGTH: 24
<212> TYPE: DNA
<213> ORGANISM: Artificial Sequence
<220> FEATURE:
<223> OTHER INFORMATION: primer : BGLD-F
<220> FEATURE:
<221> NAME/KEY: misc_feature
<222> LOCATION: (19)..(19)
<223> OTHER INFORMATION: "n" stands for any base

<400> SEQUENCE: 77
caccgccgcc taccarrtng argg                                               24

<210> SEQ ID NO 78
<211> LENGTH: 31
<212> TYPE: DNA
<213> ORGANISM: Artificial Sequence
<220> FEATURE:
<223> OTHER INFORMATION: primer : BGLD-R

<400> SEQUENCE: 78
tggcggtgta gtggttcatg scrwarwart c                                       31

<210> SEQ ID NO 79
<211> LENGTH: 20
<212> TYPE: DNA
<213> ORGANISM: Artificial Sequence
<220> FEATURE:
<223> OTHER INFORMATION: primer : BGLD-inv-F

<400> SEQUENCE: 79
cggtttcaat atcggtaagc                                                    20

<210> SEQ ID NO 80
<211> LENGTH: 20
<212> TYPE: DNA
<213> ORGANISM: Artificial Sequence
<220> FEATURE:
<223> OTHER INFORMATION: primer : BGLD-inv-R

<400> SEQUENCE: 80
gtgtccaaag ctctggaatg                                                    20

```
<210> SEQ ID NO 81
<211> LENGTH: 20
<212> TYPE: DNA
<213> ORGANISM: Artificial Sequence
<220> FEATURE:
<223> OTHER INFORMATION: primer : pBGLD-F

<400> SEQUENCE: 81
ttctctcact ttccctttcc                                                   20

<210> SEQ ID NO 82
<211> LENGTH: 20
<212> TYPE: DNA
<213> ORGANISM: Artificial Sequence
<220> FEATURE:
<223> OTHER INFORMATION: primer : pBGLD-R

<400> SEQUENCE: 82
aattgatgct cctgatgcgg                                                   20

<210> SEQ ID NO 83
<211> LENGTH: 24
<212> TYPE: DNA
<213> ORGANISM: Artificial Sequence
<220> FEATURE:
<223> OTHER INFORMATION: primer : BGLD-N

<400> SEQUENCE: 83
atgggtagcg taactagtac caac                                              24

<210> SEQ ID NO 84
<211> LENGTH: 24
<212> TYPE: DNA
<213> ORGANISM: Artificial Sequence
<220> FEATURE:
<223> OTHER INFORMATION: primer : BGLD-C

<400> SEQUENCE: 84
ctactctttc gagatgtatt tgtt                                              24
```